(12) United States Patent
Lee et al.

(10) Patent No.: US 8,383,092 B2
(45) Date of Patent: Feb. 26, 2013

(54) BIOADHESIVE CONSTRUCTS

(75) Inventors: Bruce P. Lee, Madison, WI (US); Laura Vollenweider, Middleton, WI (US); John L. Murphy, Madison, WI (US); Fangmin Xu, Middleton, WI (US); Jeffrey L. Dalsin, Madison, WI (US); Jeanne Virosco, Madison, WI (US); William Lew, Mendota Heights, MN (US); Jed White, Madison, WI (US)

(73) Assignee: KNC NER Acquisition Sub, Inc., Wilmington, DE (US)

( * ) Notice: Subject to any disclaimer, the term of this patent is extended or adjusted under 35 U.S.C. 154(b) by 320 days.

(21) Appl. No.: 12/568,527

(22) Filed: Sep. 28, 2009

(65) Prior Publication Data

US 2010/0137902 A1 Jun. 3, 2010

Related U.S. Application Data

(63) Continuation-in-part of application No. 12/099,254, filed on Apr. 8, 2008, which is a continuation-in-part of application No. 11/676,099, filed on Feb. 16, 2007, now Pat. No. 7,732,539, and a continuation-in-part of application No. 11/834,651, filed on Aug. 6, 2007, now Pat. No. 7,622,533.

(60) Provisional application No. 61/100,560, filed on Sep. 26, 2008, provisional application No. 61/100,738, filed on Sep. 28, 2008, provisional application No. 60/910,683, filed on Apr. 9, 2007.

(51) Int. Cl.
*A61K 31/74* (2006.01)
(52) U.S. Cl. .................. 424/78.27; 606/213; 424/78.08
(58) Field of Classification Search ................ 424/78.27
See application file for complete search history.

(56) References Cited

U.S. PATENT DOCUMENTS

| | | |
|---|---|---|
| 4,339,561 A | 7/1982 | Jacquet et al. |
| 4,496,397 A | 1/1985 | Waite |
| 4,585,585 A | 4/1986 | Waite |
| 4,615,697 A | 10/1986 | Robinson |
| 4,687,740 A | 8/1987 | Waite |
| 4,795,436 A | 1/1989 | Robinson |
| 4,808,702 A | 2/1989 | Waite |
| 4,908,404 A | 3/1990 | Benedict et al. |
| 4,978,336 A | 12/1990 | Capozzi et al. |
| 4,983,392 A | 1/1991 | Robinson |
| 5,015,677 A | 5/1991 | Benedict et al. |
| 5,024,933 A | 6/1991 | Yang et al. |
| 5,030,230 A | 7/1991 | White |
| 5,049,504 A | 9/1991 | Maugh et al. |
| 5,098,999 A | 3/1992 | Yamamoto et al. |
| 5,108,923 A | 4/1992 | Benedict et al. |
| 5,116,315 A | 5/1992 | Capozzi et al. |
| 5,156,956 A | 10/1992 | Motoki et al. |
| 5,192,316 A | 3/1993 | Ting |
| 5,197,973 A | 3/1993 | Pang et al. |
| 5,202,236 A | 4/1993 | Maugh et al. |
| 5,202,256 A | 4/1993 | Maugh et al. |
| 5,225,196 A | 7/1993 | Robinson |
| 5,242,808 A | 9/1993 | Maugh et al. |
| 5,260,194 A | 11/1993 | Olson |
| 5,374,431 A | 12/1994 | Pang et al. |
| 5,410,023 A | 4/1995 | Burzio |
| 5,428,014 A | 6/1995 | Labroo et al. |
| 5,487,739 A | 1/1996 | Aebischer et al. |
| 5,490,980 A | 2/1996 | Richardson et al. |
| 5,520,727 A | 5/1996 | Vreeland et al. |
| 5,525,336 A | 6/1996 | Green et al. |
| 5,549,904 A | 8/1996 | Juergensen et al. |
| 5,563,047 A | 10/1996 | Petersen |
| 5,574,134 A | 11/1996 | Waite |
| 5,580,697 A | 12/1996 | Keana et al. |
| 5,582,955 A | 12/1996 | Keana et al. |
| 5,605,938 A | 2/1997 | Roufa et al. |
| 5,618,551 A | 4/1997 | Tardy et al. |
| 5,628,793 A | 5/1997 | Zirm |
| 5,705,177 A | 1/1998 | Roufa et al. |
| 5,705,178 A | 1/1998 | Roufa et al. |
| 5,736,132 A | 4/1998 | Juergensen et al. |
| 5,776,747 A | 7/1998 | Schinstine et al. |
| 5,800,828 A | 9/1998 | Dionne et al. |
| 5,817,470 A | 10/1998 | Burzio et al. |
| 5,830,539 A | 11/1998 | Yan et al. |
| 5,834,232 A | 11/1998 | Bishop et al. |
| 5,858,747 A | 1/1999 | Schinstine et al. |
| 5,935,849 A | 8/1999 | Schinstine et al. |
| 5,939,385 A | 8/1999 | Labroo et al. |
| 5,955,096 A | 9/1999 | Santos et al. |
| 5,968,568 A | 10/1999 | Kuraishi et al. |
| 5,985,312 A | 11/1999 | Jacob et al. |
| 5,994,325 A | 11/1999 | Roufa et al. |
| 6,010,871 A | 1/2000 | Takahara et al. |

(Continued)

FOREIGN PATENT DOCUMENTS

| | | |
|---|---|---|
| JP | 03-294292 | 12/1991 |
| JP | 2000-281699 | 10/2000 |

(Continued)

OTHER PUBLICATIONS

Lee et al. Biological Adhesives, 2006,257-277.*

(Continued)

*Primary Examiner* — Michael G Hartley
*Assistant Examiner* — Sean R Donohue
(74) *Attorney, Agent, or Firm* — Casimir Jones S.C.

(57) ABSTRACT

The invention describes substrates, such as prosthetics, films, nonwovens, meshes, etc. that are treated with a bioadhesive. The bioadhesive includes polymeric substances that have phenyl moieties with at least two hydroxyl groups. The bioadhesive constructs can be used to treat and repair, for example, hernias and damaged tendons.

8 Claims, 13 Drawing Sheets

U.S. PATENT DOCUMENTS

| | | | |
|---|---|---|---|
| 6,020,326 A | 2/2000 | Roufa et al. | |
| 6,022,597 A | 2/2000 | Yan et al. | |
| 6,083,930 A | 7/2000 | Roufa et al. | |
| 6,093,686 A | 7/2000 | Nakada et al. | |
| 6,129,761 A | 10/2000 | Hubbell | |
| 6,150,461 A | 11/2000 | Takei et al. | |
| 6,156,348 A | 12/2000 | Santos et al. | |
| 6,162,903 A | 12/2000 | Trowern et al. | |
| 6,235,313 B1 | 5/2001 | Mathiowitz et al. | |
| 6,267,957 B1 | 7/2001 | Green et al. | |
| 6,284,267 B1 | 9/2001 | Aneja | |
| 6,294,187 B1 | 9/2001 | Boyce et al. | |
| 6,306,993 B1 | 10/2001 | Rothbard et al. | |
| 6,309,669 B1 | 10/2001 | Setterstrom et al. | |
| 6,322,996 B1 | 11/2001 | Sato et al. | |
| 6,325,951 B1 | 12/2001 | Soper et al. | |
| 6,331,422 B1 | 12/2001 | Hubbell et al. | |
| 6,335,430 B1 | 1/2002 | Qvist | |
| 6,365,187 B2 | 4/2002 | Mathiowitz et al. | |
| 6,368,586 B1 | 4/2002 | Jacob et al. | |
| 6,417,173 B1 | 7/2002 | Roufa et al. | |
| 6,486,213 B1 | 11/2002 | Chen et al. | |
| 6,491,903 B1 | 12/2002 | Forster et al. | |
| 6,497,729 B1 | 12/2002 | Moussy et al. | |
| 6,506,577 B1 | 1/2003 | Deming et al. | |
| 6,555,103 B2 | 4/2003 | Leukel et al. | |
| 6,565,960 B2 | 5/2003 | Koob et al. | |
| 6,566,074 B1 | 5/2003 | Goetinck | |
| 6,566,406 B1 | 5/2003 | Pathak et al. | |
| 6,635,274 B1 | 10/2003 | Masiz et al. | |
| 6,663,883 B1 | 12/2003 | Akiyama et al. | |
| 6,821,530 B2 * | 11/2004 | Koob et al. | 424/458 |
| 6,887,845 B2 | 5/2005 | Barron et al. | |
| 7,009,034 B2 | 3/2006 | Pathak et al. | |
| 7,208,171 B2 | 4/2007 | Messersmith et al. | |
| 7,300,991 B2 | 11/2007 | Nishimura et al. | |
| 7,622,533 B2 | 11/2009 | Lee et al. | |
| 7,732,539 B2 | 6/2010 | Shull et al. | |
| 2001/0043940 A1 | 11/2001 | Boyce et al. | |
| 2001/0049400 A1 | 12/2001 | Alli et al. | |
| 2002/0022013 A1 | 2/2002 | Leukel et al. | |
| 2002/0049290 A1 | 4/2002 | Vanderbilt | |
| 2002/0182633 A1 | 12/2002 | Chen et al. | |
| 2003/0009235 A1 | 1/2003 | Manrique et al. | |
| 2003/0012734 A1 | 1/2003 | Pathak et al. | |
| 2003/0039676 A1 | 2/2003 | Boyce et al. | |
| 2003/0065060 A1 | 4/2003 | Qvist et al. | |
| 2003/0069205 A1 | 4/2003 | Roufa et al. | |
| 2003/0087338 A1 | 5/2003 | Messersmith et al. | |
| 2003/0099682 A1 | 5/2003 | Moussy et al. | |
| 2003/0109587 A1 | 6/2003 | Mori | |
| 2003/0119985 A1 * | 6/2003 | Sehl et al. | 525/54.1 |
| 2003/0194610 A1 | 10/2003 | Nishimura et al. | |
| 2003/0208888 A1 | 11/2003 | Fearing et al. | |
| 2004/0005421 A1 | 1/2004 | Gervase et al. | |
| 2004/0028646 A1 | 2/2004 | Gross et al. | |
| 2004/0049187 A1 * | 3/2004 | Burnett et al. | 606/52 |
| 2005/0032929 A1 | 2/2005 | Greener | |
| 2005/0155937 A1 | 7/2005 | Zawada et al. | |
| 2005/0208091 A1 * | 9/2005 | Pacetti | 424/423 |
| 2005/0288398 A1 | 12/2005 | Messersmith et al. | |
| 2006/0009550 A1 | 1/2006 | Messersmith et al. | |
| 2007/0031498 A1 * | 2/2007 | Zong et al. | 424/486 |
| 2007/0208141 A1 | 9/2007 | Shull et al. | |
| 2008/0171836 A1 | 7/2008 | Lee et al. | |
| 2008/0247984 A1 | 10/2008 | Messersmith | |
| 2008/0286326 A1 | 11/2008 | Benco | |

FOREIGN PATENT DOCUMENTS

| | | |
|---|---|---|
| WO | 2005/056708 | 6/2005 |
| WO | 2010/091300 | 8/2010 |

OTHER PUBLICATIONS

Oxlund et al, Collagen deposition and mechanical strength of colon anastomoses and skin incisional wounds of rats, J Surg Res. Nov. 1996;66(1):25-30.

Jorgensen et al., Dose-response study of the effect of growth hormone on mechanical properties of skin graft wounds, J Surg Res. Mar. 1995;58(3):295-301.

da Silva, L.F.M., T.N.S.S. Rodrigues, M.A.V. Figueiredo, M.F.S.F. de Moura, and J.A.G. Chousal, Effect of Adhesive Type and Thickness on the Lap Shear Strength J. Adh., 2006. 82: p. 1091-1115.

Santillan-Doherty, P., R. Jasso-Victoria, A. Sotres-Vega, R. Olmos, J.L. Arreola, D. Garcia, B. Vanda, M. Gaxiola, A. Santibanez, S. Martin, and R. Cabello, Thoracoabdominal wall repair with glutaraldehyde-preserved bovine pericardium. Journal of investigative surgery : the official journal of the Academy of Surgical Research, 1996. 9(1): p. 45-55.

Burger, J.W.A., J.A. Halm, A.R. Wijsmuller, S. ten Raa, and J. Jeekel, Evaluation of new prosthetic meshes for ventral hernia repair. Surgical endoscopy, 2006. 20(8): p. 1320-5.

Lo Menzo, E., J.M. Martinez, S.A. Spector, A. Iglesias, V. Degennaro, and A. Cappellani, Use of biologic mesh for a complicated paracolostomy hernia. American journal of surgery, 2008. 196(5): p. 715-9.

* cited by examiner

General structure of Medhesive.

*In vitro* degradation of cured Medhesive hydrogels as followed by the percent dry weight remaining in the adhesive.

Figure 5

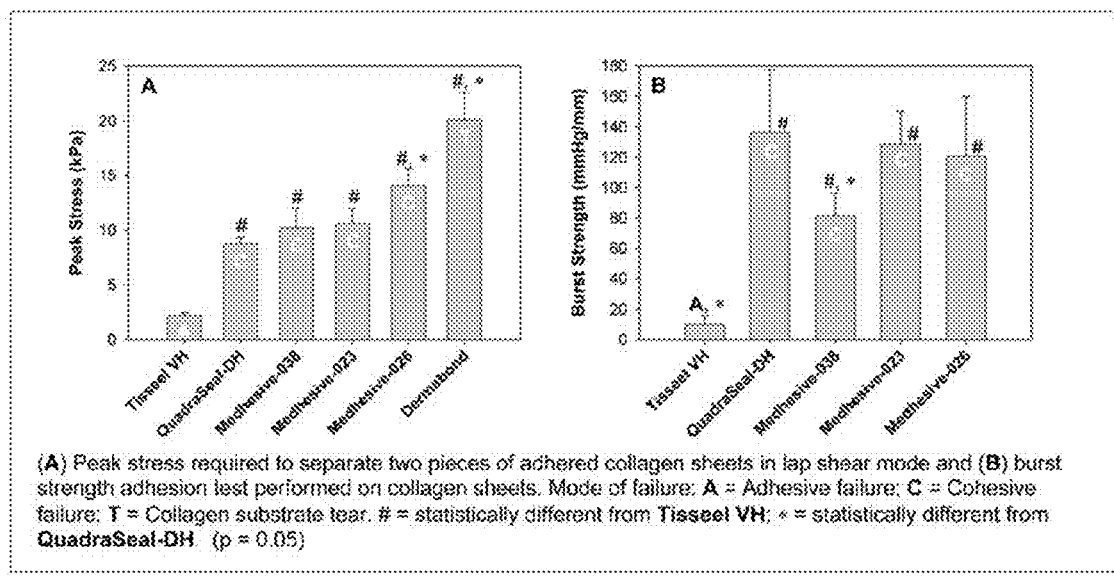

(A) Peak stress required to separate two pieces of adhered collagen sheets in lap shear mode and (B) burst strength adhesion test performed on collagen sheets. Mode of failure: A = Adhesive failure; C = Cohesive failure; T = Collagen substrate tear. # = statistically different from Tisseel VH; * = statistically different from QuadraSeal-DH. ($p = 0.05$)

Figure 6

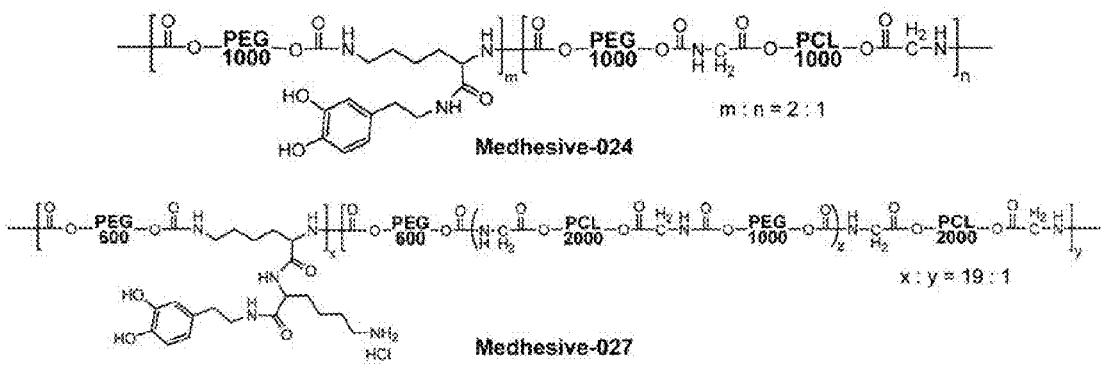

Chemical structures of adhesive polymers to be tested as adhesive coatings applied to biologic mesh.

Figure 7

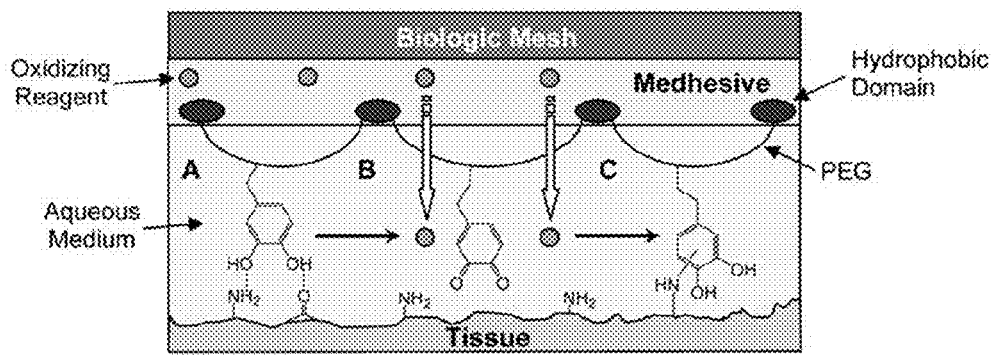

(A) Schematic of the proposed bioadhesive biologic prosthetic embedded with oxidizing reagent. As the adhesive is rehydrated, (B) the solubilized oxidizing reagent is released and oxidizes the catechol, (C) resulting in covalent crosslink formation between the catechol and functional groups present on the tissue surface.

Figure 8

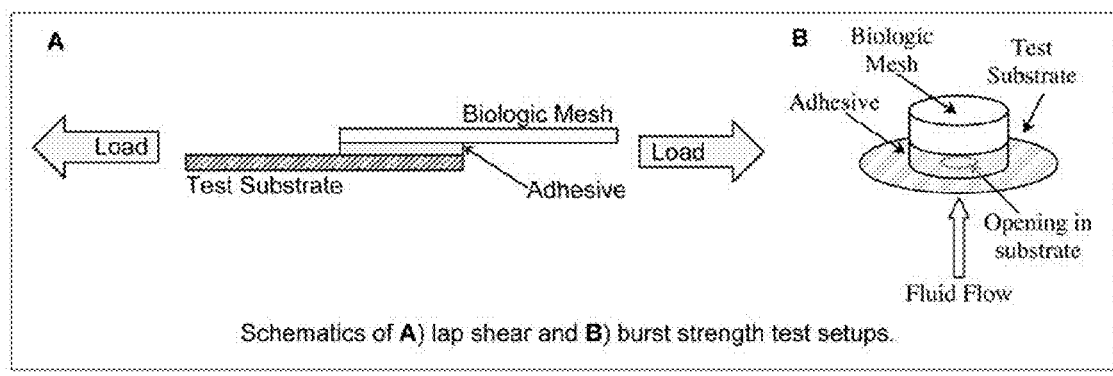

Schematics of A) lap shear and B) burst strength test setups.

Left blank intentionally

Adhesion tests results from a) lap shear adhesion test, b) T-peel test, and c) burst strength test. Mode of failure: M, mixture of adhesive and cohesive failure; A, adhesive failure; C, cohesive failure; T, substrate tear.

Figure 12
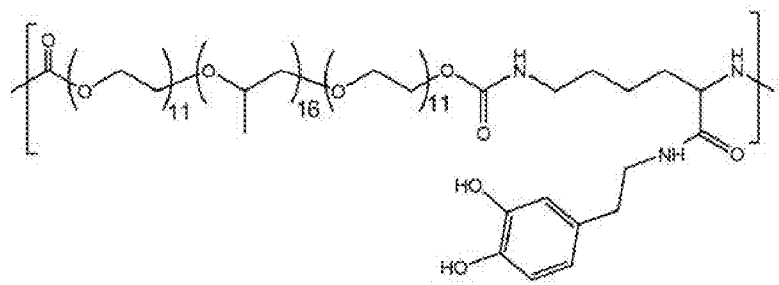
Nerites-4
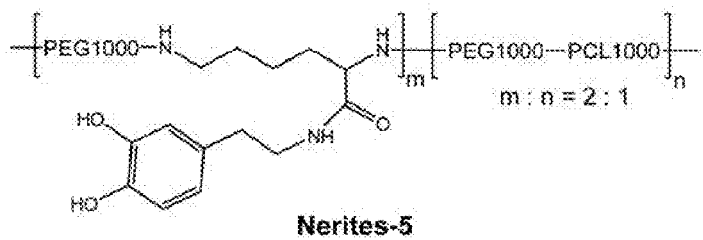
Nerites-5
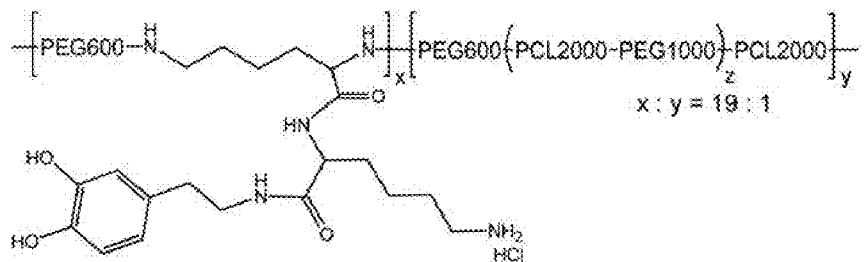
Nerites-6
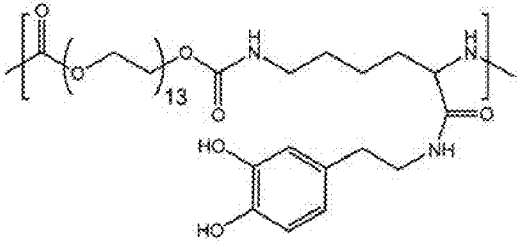
Nerites-7
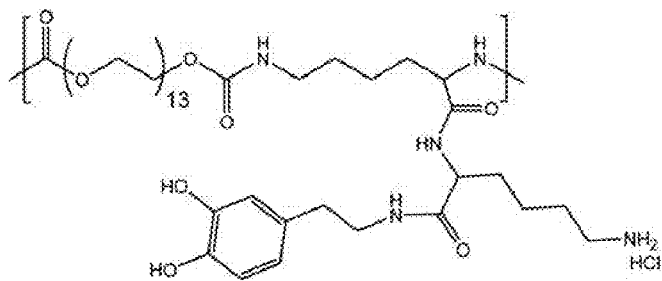
Nerites-8
Chemical structures of adhesive polymers to be tested as an adhesive coating on collagen membranes.

Figure 13 (cont.)
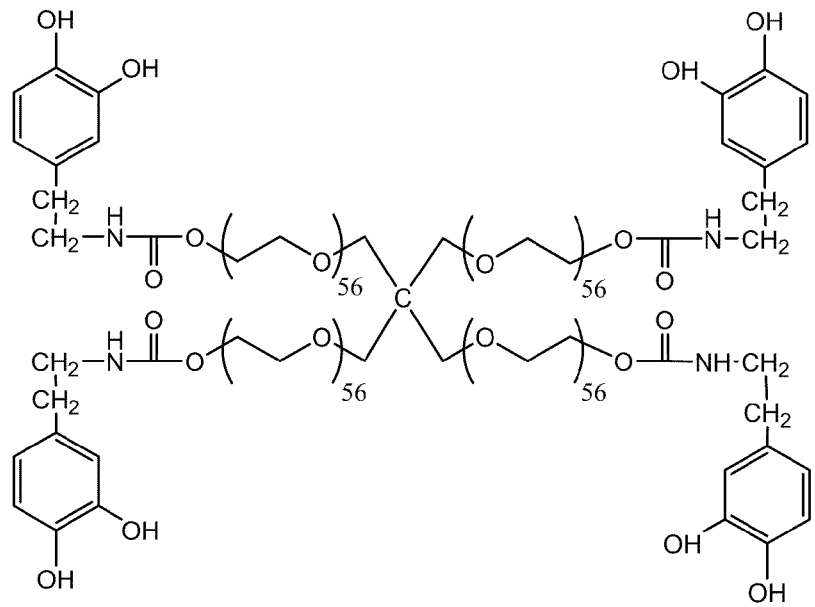
C-(PEG-DMu)$_4$
PEG 10K – (DMu)$_4$
(e)
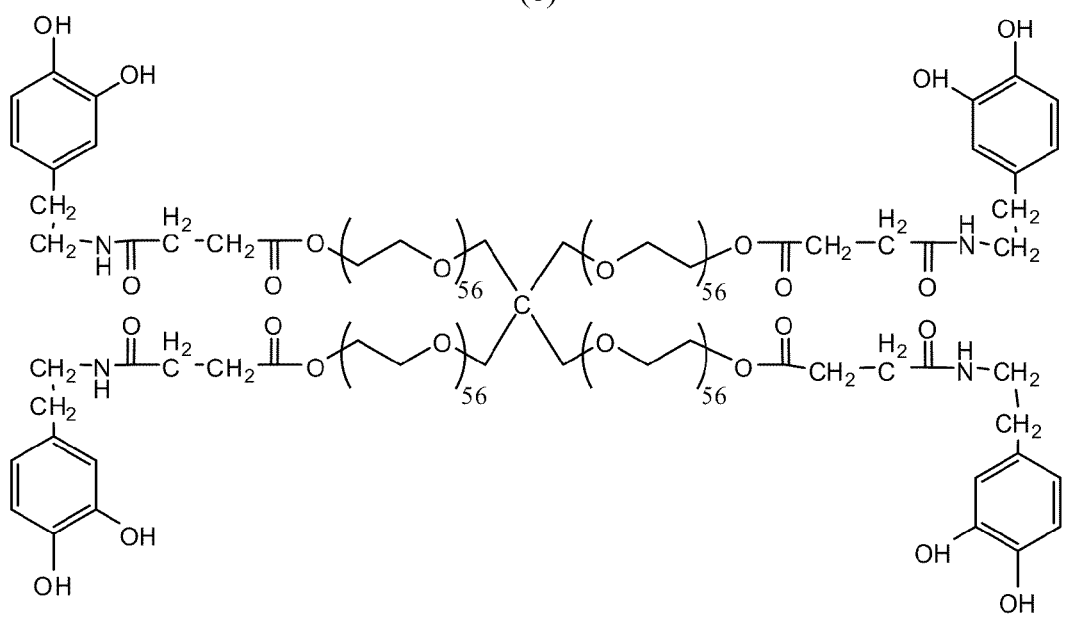
C-(PEG-DMe)$_4$
PEG 10K – (DMe)$_4$
(f)

Lap shear adhesion tests performed on collagen backing coated with Medhesive-024 and compared to adhesive joints adhered with commercially available tissue adhesives.

Burst strength tests performed on collagen backing coated with Medhesive-024.

Figure 8: Photographs of A) uncoated and B) QS-DH-coated Marlex surgical meshes.

BIOADHESIVE CONSTRUCTS

CROSS REFERENCE TO RELATED APPLICATIONS

The present application claims the benefit of U.S. provisional application Ser. No. 61/100,560 filed Sep. 26, 2008, and U.S. provisional application Ser. No. 61/100,738 filed Sep. 28, 2008, the contents of which are incorporated in their entirety herein by reference. The present application also claims the benefit of U.S. application Ser. No. 12/099,254, filed Apr. 8, 2008, which claims the benefit of U.S. provisional application Ser. No. 60/910,683 filed on Apr. 9, 2007, U.S. application Ser. No. 11/676,099, filed Feb. 16, 2007, and U.S. application Ser. No. 11/834,651, filed Aug. 6, 2007, the contents of which are incorporated in their entirety herein by reference including any provisional applications referred to therein for a priority date(s).

REFERENCE TO FEDERAL FUNDING

The project was funded in part by NIH (1R43AR056519-01A1, 1R43DK083199-01, and 2R44DK083199-02), and NSF (IIP-0912221) grants. NMR characterization was performed at NMRFAM, which is supported by NIH (P41RR02301, P41GM66326, P41GM66326, P41RR02301, RR02781, RR08438) and NSF (DMB-8415048, OIA-9977486, BIR-9214394) grants. The government has certain rights in the invention.

FIELD OF THE INVENTION

The invention relates generally various substrates, such as prosthetics, films, nonwovens, meshes, etc. that are treated with a bioadhesive. The bioadhesive includes polymeric substances that have phenyl moieties with at least two hydroxyl groups. The bioadhesive constructs can be used to treat and repair, for example, hernias and damaged tendons.

BACKGROUND OF THE INVENTION

Surgical prostheses, meshes, and grafts are commonly used in surgical procedures that include tendon and ligament repair, hernia repair, cardiovascular surgery, as well as certain dental surgical procedures. These prosthetic materials are fixated through the use of sutures, staples, or tacks. While such fixation methods have demonstrated success in immobilizing surgical prostheses, they are also a source of existing problems associated with each surgical procedure. In some instances, sutures may not be practical in certain situations where there is limited space or light source needed for suturing.

Hernia repair is one of the most commonly performed surgeries in the US. Although the use of prosthetic mesh as a reinforcement has significantly improved surgical outcomes, the rate of hernia recurrence remains as high as 30-50%. Moreover, current prosthetic materials are associated with numerous complications, including increased risk of infection, prosthetic shrinkage and host foreign body reactions. Such reactions often lead to changes in prosthetic mesh textile properties and result in a diminished postoperative patient quality of life. Recent advances in tissue engineering have seen the introduction of various biologic prosthetic meshes. These biologic meshes are derived from human or animal tissue modified both to preserve the structural framework of the original tissue and to eliminate cells potentially capable of instigating a foreign body reaction. Following implantation, these biologic implants become a site for remodeling via fibroblast migration, followed by subsequent native collagen deposition.

In addition to mesh type, effective immobilization of the mesh against the abdominal wall is also critical to the success of the hernia repair. Currently, both synthetic and biologic meshes are held in place with sutures and staples. While these fixation methods demonstrate variable success, their usage is believed to be a source of nerve damage and chronic discomfort. Thus, finding an effective alternative to sutures and metal staples would dramatically enhance the long-term biocompatibility of these meshes.

Tendon and ligament injuries have been occurring with increasing frequency over the last several decades. While methods for the fixation of torn tendons and ligaments have improved, none has proven ideal. The existing methods of using sutures alone or sutures with a variety of graft materials can create weak points at the sutures and require immobilization for a period of time after repair, before rehabilitation can begin. The evidence generated by the medical community is that earlier rehabilitation increases the likelihood that the repair of such injuries will be successful. A new method for repairing tendon and ligament injuries that would allow earlier rehabilitation and fewer incidences of post-operative pain, surgical complications, and rerupture of the repaired tissues is clearly needed.

Therefore, a need exists for improved materials and methods that overcome one or more of the current disadvantages.

BRIEF SUMMARY OF THE INVENTION

The present invention surprisingly provides unique bioadhesive constructs that are suitable to repair or reinforce damaged tissue.

The constructs include a suitable support that can be formed from a natural material, such as collagen or man made materials such as polypropylene and the like. The support can be a film, a membrane, a mesh, a non-woven and the like. The support need only help provide a surface for the bioadhesive to adhere. The support should also help facilitate physiological reformation of the tissue at the damaged site. Thus the constructs of the invention provide a site for remodeling via fibroblast migration, followed by subsequent native collagen deposition.

The bioadhesive is any polymer that includes multihydroxy phenyl groups, referred to herein a DHPD's. The polymer backbone can be virtually any material as long as the polymer contains DHPD's that are tethered to the polymer via a linking group or a linker. Generally, the DHPD comprises at least about 1 to 100 weight percent of the polymer (DHPp), more particularly at least about 2 to about 65 weight percent of the DHPp and even more particularly, at least about 3 to about 55 weight percent of the DHPp. Suitable materials are discussed throughout the specification.

In certain embodiments an oxidant is included with the bioadhesive film layer. The oxidant can be incorporated into the polymer film or it can be contacted to the film at a later time. A solution could be sprayed or brushed onto either the adhesive surface or the tissue substrate surface. Alternatively, the construct can be dipped or submerged in a solution of oxidant prior to contacting the tissue substrate. In any situation, the oxidant upon activation, can help promote crosslinking of the multihydroxy phenyl groups with each other and/or tissue. Suitable oxidants include periodates and the like.

The invention further provides crosslinked bioadhesive constructs or hydrogels derived from the compositions described herein. For example, two DHDP moieties from two separate polymer chains can be reacted to form a bond between the two DHDP moieties. Typically, this is an oxidative/radical initiated crosslinking reaction wherein oxidants/initiators such as $NaIO_3$, $NaIO_4$, Fe III salts, ($FeCl_3$), Mn III salts ($MnCl_3$), $H_2O_2$, oxygen, an inorganic base, an organic base or an enzymatic oxidase can be used. Typically, a ratio of oxidant/initiator to DHDP containing material is between about 0.2 to about 1.0 (on a molar basis) (oxidant:DHDP). In one particular embodiment, the ratio is between about 0.25 to about 0.75 and more particularly between about 0.4 to about 0.6 (e.g., 0.5). It has been found that periodate is very effective in the preparation of crosslinked hydrogels of the invention. Additionally, it is possible that oxidation "activates" the DHPD(s) which allow it to form interfacial crosslinking with appropriate surfaces with functional group (i.e. biological tissues with —NH2, —SH, etc.)

Typically, when the DHDP containing construct is treated with an oxidant/initiator as described herein, the coating gels (crosslinks) within 1 minute, more particularly within 30 seconds, most particularly under 5 seconds and in particular within 2 seconds or less. For example, QuadraSeal-D4 (PEG10k-($D_4$)$_4$) (FIG. 13b) gelled with in 2 seconds or less at a $IO_4$:DOPA mole ratio of 0.25 or higher.

The use of the bioadhesive constructs eliminates or reduces the need to use staples, sutures, tacks and the like to secure or repair damaged tissue, for example, such as herniated tissue or torn ligaments or tendons.

The bioadhesive constructs of the invention combine the unique adhesive properties of multihydroxy (dihydroxyphenyl)-containing polymers with the biomechanical properties, bioinductive ability, and biodegradability of biologic meshes to develop a novel medical device for hernia repair. A thin film of biodegradable, water-resistant adhesive will be coated onto a commercially available, biologic mesh to create an adhesive bioprosthesis. These bioadhesive prosthetics can be affixed over a hernia site without sutures or staples, thereby potentially preventing tissue and nerve damage at the site of the repair. Both the synthetic glue and the biologic meshes are biodegradable, and will be reabsorbed when the mechanical support of the material is no longer needed; these compounds prevent potential long-term infection and chronic patient discomfort typically associated with permanent prosthetic materials. Additionally, minimal preparation is required for the proposed bioadhesive prosthesis, which can potentially simplify surgical procedures. The adhesive coating will be characterized, and both adhesion tests and mechanical tests will be performed on the bioadhesive biologic mesh to determine the feasibility of using such a material for hernia repair.

Additionally, the unique adhesive properties of dihydroxyphenyl-containing polymers can be combined with the biomechanical properties, bioinductive ability, and biodegradability of a collagen membrane to develop a novel augmentation device for tendon and ligament repair. These bioadhesive tapes can be wrapped around or placed over a torn tendon or ligament to create a repair stronger than sutures alone. This new method of augmentation supports the entire graft surface by adhering to the tissue being repaired, as opposed to conventional repair methods, which use sutures to attach the graft at only a few points. Securing the repaired tissue more effectively means that patients can potentially begin post-operative rehabilitation much sooner, a critical development, as early mobilization has been found to be crucial for regenerating well organized and functional collagen fibers in tendons and ligaments. The collagen membranes will be coated with biomimetic synthetic adhesive polymers (described herein) to create a bioadhesive collagen tape. The adhesive coating will be characterized, and both adhesion and mechanical tests will be performed on the bioadhesive collagen tape to determine the feasibility of using such a material to augment tendon and ligament repair.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 5 provides physical data on several of the constructs of the invention and commercially available materials.

FIG. 6 provides the chemical structure of two of the bioadhesives used in the constructs of the invention.

FIG. 7 provides a schematic of how the bioadhesive construct can function.

FIG. 8 is a diagram of lap shear and burst test setups.

FIG. 12 provides chemical structures of several of the bioadhesive coatings.

DETAILED DESCRIPTION

Figure 1:
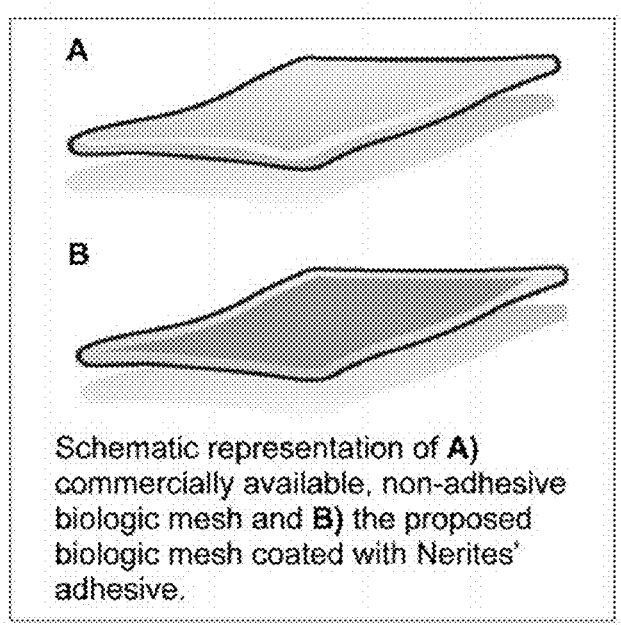
FIG. 1 provides a schematic representation of a bioadhesive construct of the invention.

In the specification and in the claims, the terms "including" and "comprising" are open-ended terms and should be interpreted to mean "including, but not limited to . . . ." These terms encompass the more restrictive terms "consisting essentially of" and "consisting of"

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

General Applications

In one embodiment, adhesive compounds of the present invention provide a method of adhering a first surface to a second surface in a subject. In some embodiments, the first and second surfaces are tissue surfaces, for example, a natural tissue, a transplant tissue, or an engineered tissue. In further embodiments, at least one of the first and second surfaces is an artificial surface. In some embodiments, the artificial surface is an artificial tissue. In other embodiments, the artificial surface is a device or an instrument. In some embodiments, adhesive compounds of the present invention seal a defect between a first and second surface in a subject. In other embodiments, adhesive compounds of the present invention provide a barrier to, for example, microbial contamination, infection, chemical or drug exposure, inflammation, or metastasis. In further embodiments, adhesive compounds of the present invention stabilize the physical orientation of a first surface with respect to a second surface. In still further embodiments, adhesive compounds of the present invention reinforce the integrity of a first and second surface achieved by, for example, sutures, staples, mechanical fixators, or mesh. In some embodiments, adhesive compounds of the present invention provide control of bleeding. In other embodiments, adhesive compounds of the present invention provide delivery of drugs including, for example, drugs to control bleeding, treat infection or malignancy, or promote tissue regeneration.

The bioadhesive constructs described herein can be used to repair torn, herniated, or otherwise damaged tissue. The tissue can vary in nature but includes cardiovascular, vascular, epithelial, ligament, tendon, muscle, bone and the like. The constructs can be utilized with general surgical techniques or with more advanced laparoscopic or arthroscopic surgery techniques. Once the constructs are applied to the damaged/injured site, they can be directly adhered to the tissue. Alternatively and in addition to the adherence of the adhesive to the tissue, staples, sutures or tacks and the like can also be used to help secure the construct.

In addition to tendon and ligament repair and hernia repair, the bioadhesive construct could potentially be utilized in cardiovascular surgery. Over 600,000 vascular grafts are implanted annually to replace damaged blood vessels. Coronary artery bypass grafting (CABG) is the most common method of replacing diseased blood vessels. When no suitable autologous vessels are available, there are several synthetic materials used for prosthetic vascular grafts such as PTFE, polyurethane and Dacron. Such materials have been used in cardiovascular repair since the early 1950's. In addition to synthetic grafts, collagen has been investigated with some success for use as a cardiovascular graft material, especially in large diameter vessels. Regardless of the graft material used, sutures are almost always used to secure the graft to the existing tissue. Disadvantages of using sutures are that it takes the surgeon a considerable amount of time and that there is the potential of the sutures tearing through the graft material.

Another potential application for the current invention is dental implants. Collagen membranes (Biomend®) have also been utilized in guided bone regeneration (GBR) to promote implant wound healing in clinical periodontics. Materials used in GBR are either placed over the defect followed by wound closure, or can be sutured in place prior to wound closure. Adhesive collagen membranes could reduce surgery time and simplify the process of securing the membrane.

In addition to using the biomimetic glue as a method of prosthesis fixation, the adhesive can be applied as a sealant to prevent leakage of blood in cardiovascular repair. Furthermore, the present adhesives are constructed with predominately PEG-based polymers, which are widely known for their antifouling properties. Once the catechol undergoes oxidative crosslinking with the tissue substrate or during curing of the adhesive, the biomimetic adhesive loses its adhesive properties and becomes a barrier for bacterial adhesion or tissue adhesion.

The bioadhesive constructs of the invention can be used to repair the entrance portal in annulus fibrosis used for insertion of nucleus fibrosis replacement; prevent extrusion of implant by patch fixation. The constructs can also be used for the repair of annulus fibrosis in herniated disc or after discectomy by patch fixation.

The bioadhesive constructs can be used as a barrier for bone graft containment in posterior fusion procedures. This provides containment around bone graft material either by patching in place, or by pre-coating a containment patch with the bioadhesive ("containment adhesive bandage") and then applying.

The bioadhesive constructs of the invention can be used to treat stress fractures.

The bioadhesive constructs of the invention can be used to repair lesions in avascular portion of knee meniscus. A construct can be used to stabilize a meniscal tear and connect the avascular region with vascular periphery to encourage ingrowth of vascularity and recruitment of meniscal progenitor cells. Current techniques lead to repair with weak non-meniscal fibrous scar tissue. The bioadhesive patch may also serve as vehicle for delivery of growth factors and progenitor cells to enhance meniscus repair.

In certain embodiments the bioadhesive constructs of the invention can be referred to as a "patch". In other embodiments, the bioadhesive constructs can be referred to as a "tape". In any event, the bioadhesive constructs include a bioadhesive layer and a support material.

The following sections will exemplify the utility of the bioadhesive constructs in specific uses.

Hernia Repair

According to the National Institute of Diabetes and Digestive and Kidney Diseases (NIDDK), a hernia occurs when part of an internal organ bulges through a weak area of muscle.[2] There are several different types of hernias including inguinal hernia, femoral hernia, incisional (ventral) hernia, hiatal hernia, diaphragmatic hernia and umbilical hernia, but most hernias occur in the abdomen. As many as 800,000 surgical hernia repairs are performed annually in the United States,[2] which account for 10-24% of all surgical procedures performed each year.[3,4] Incisional hernias are of significant concern as up to 20% of laparotomies result in a primary incisional hernia.[5-7] In the United States alone, laparotomies result in nearly 500,000 new hernia cases each year.[7] Given such staggering statistics, it is imperative to find a safe and reliable treatment for incisional hernias. Recurrence is the customary measure of hernia repair failure. Hernia recurrence is a significant problem, with reported recurrence rates from 0.2% to 55% of all repairs, regardless of repair method.[3-5,8-15] Evidence also shows an increased rate of failure in the repair of recurrent hernias.[6,9] Besides recurrence, chronic pain and discomfort is another indicator of failure in hernia repair. Studies have found that 18-63% of procedures result in chronic pain, with the pain affecting daily activity in 4-12% of patients.[10, 16]

Current Repair Methods

Three main types of hernia repair are commonly performed: tissue approximation, tension-free open repair with prosthetic mesh, and laparoscopic repair. What constitutes the best method of hernia repair elicits much controversy within the medical community, and each new method developed to improve current approaches of hernia repair is closely scrutinized.

Tissue Approximation

Tissue approximation involves the use of permanent sutures to approximate the fascia surrounding the abdominal tissues.[9] One reported advantage of tissue approximation is that the repairs can be performed under local anesthetic; some tension-free mesh repairs and all laparoscopic repairs are performed only under general anesthesia. Local anesthesia offers two advantages: 1) the patient can still cough and strain, allowing the surgeon to test the repair at the end of the procedure, and 2) the patient can begin to mobilize the muscles surrounding the repair immediately following surgery.[17] Early mobilization can reduce post-operative pain, because it prevents muscle cramps.[18] In 1887, treatment of inguinal hernias was revolutionized with the introduction of the Bassini repair. Bassini was the first surgeon to experience any measureable success in the surgical repair of a hernia.[17] In the 1950s, the Shouldice procedure was introduced as an alternative to the Bassini method and an approach to reduce high recurrence rates.[8] However, the Shouldice was also criticized for being for too technically challenging.[10] Due to high recurrence rates associated with tissue approximation methods, most general surgeons have moved away from pure tissue repairs to tension-free techniques with prosthetic materials to achieve better results.[19]

Tension-Free Open Repair Using a Prosthetic Mesh

The next major advancement in hernia repair was the use of a polyethylene mesh to reinforce the repair, a technique first introduced in 1959 by Francis Usher. Since then, polypropylene and an assorted other synthetic materials have replaced polyethylene.[8, 20] Tension-free repairs are achieved by placing a prosthetic, non-absorbable mesh over the defect and either securing the mesh with sutures[5, 6, 16] or using intraperitoneal pressure to hold the mesh in place.[11, 19] The Lichtenstein technique of hernia repair is considered the gold standard method by the American College of Surgeons and is reportedly the most widely performed method of hernia repair in the United States.[2, 4, 8] The major advantage of tension-free repairs is reduced post-operative pain due to lack of the tension that conventional open repairs induce by suturing the transversalis fascia. While tension-free techniques have been associated with lower rates of recurrence, improved post-operative patient comfort, and less difficulty in surgical training,[2, 10, 16, 21] there is much concern over the long-term safety of implanted meshes and their associated post-operative complications. Such complications include chronic inflammatory response, mesh dislocation, fistula formation, spermatic granuloma, infection, erosion of mesh material, paraesthesia and failure of the repair due to mesh shrinkage.[9, 13, 16, 18, 20]

Laparoscopic Repair

When laparoscopic repair was initially introduced, it was widely popular due to the minimally invasive nature of the surgery, which results in reduced pain and earlier return to normal activities.[2, 9, 14, 21] Laparoscopic hernia repair almost always involves placement of a mesh to reinforce the repair.[11] The method of mesh fixation includes the use of staples,[10, 14] titanium clips or tacks,[16, 22] or interperitoneal pressure to hold the mesh in place.[11, 15] While it has been shown that there is less postoperative pain following laparoscopic hernia repair than following either Shouldice and Lichtenstein repairs, the laparoscopic technique is technically much more complex than other methods, and therefore has a very long learning curve.[16] Other disadvantages of the laparoscopic approach include higher cost, use of general anesthesia as opposed to local anesthesia, occurrence of more serious intraoperative complications than with open procedures, and the lack of long-term data regarding these types of repair.[2, 9, 21]

Mesh Materials

The choice of mesh material is often one of the most important factors that dictates the success rate of a repair. While the desired characteristics of an ideal mesh are well known, no single material fulfills all the requirements.[7] The mesh should allow host tissue incorporation for permanent fixation, without promoting scarring, mesh encapsulation, or a foreign body response. The mesh should also be easy to handle, easy to sterilize, and chemically inert.[23-26] Many factors influence mesh safety, including the material the mesh is composed of, pore size, filament structure, and mesh position (onlay, inlay, sublay, intraperitoneal).[5] Synthetic non-absorbable mesh is most often used clinically. However, due to various problems associated with permanently implanted materials, bioprostheses have recently gained popularity among surgeons and these biologic meshes may supplant meshes of synthetic origin in the future.

Conventional Mesh

Currently, macroporous polypropylene meshes are the most commonly used material for hernia repair.[7, 27-29] Examples include Marlex (C. R. Bard, Cranston, N.J.), Prolene (Ethicon, Inc., Somerville, N. J.), Surgipro (US Surgical, Norwalk, Conn.) and Prolite (Atrium Medical, Hudson, N.H.). The large pore size of these materials allows fibroblasts, collagen fibers, blood vessels, and macrophages, which are essential for a strong hernia repair, to pass through.[30] Additionally, polypropylene resists biological degradation, so it can provide lasting protection of the repair site.[7] However, there is growing concern with polypropylene meshes as they can shrink and migrate to neighboring organs, as well as form dense adhesions with the intestines.[30] Expanded polytetrafluoroethylene (ePTFE) was introduced as a biomaterial for hernia repair in the early 1980s.[7] Meshes made from this material are flexible and soft, and the material does not induce a severe foreign body response. The most commonly used ePTFE mesh is DualMesh (W. L. Gore and Associates, Flagstaff, Ariz.) and is designed for intra-abdominal use. One side of DualMesh is corrugated and rough, supporting tissue ingrowth from the abdominal wall, while the other side is composed of a microporous material so that DualMesh can safely be placed in contact with the intestines.[7, 30] The microporous aspect of these materials can harbor bacteria and promote infection since the small pore size does not permit passage of large antimicrobial agents. Such infections often result in mesh removal.[8, 30] One of the newest advances in mesh materials has been the introduction of 'lightweight' meshes. These are composed of non-absorbable materials with thin filaments and larger pore sizes than traditional materials, resulting in a >50% reduction in prosthetic weight.[7] It is hypothesized that decreasing the amount of implanted material by using reduced-weight meshes may also decrease the inflammatory reaction and thereby improve clinical outcomes.[23, 27, 31, 32]

Bioprostheses

The persistent array of complications associated with synthetic meshes has spurred the development of biologic materials derived from porcine small intestinal submucosa (SIS; Surgisis®, Cook Biotech Inc.), cross-linked porcine dermal tissue (Permacol, Tissue Science Laboratories, and Colla-Mend, C. R. Bard, Inc.), and acellular cadaver dermis (Allo-Derm, Life Cell Corporation) for hernia repair.[8, 30] These biologic materials provide a scaffold that promotes tissue ingrowth. Several studies using SIS have shown rapid tissue ingrowth and remodeling, resulting in an organized collagenous tissue which is as strong as a defect repaired with non-absorbable mesh and native tissue.[24-26, 33-37] In addition, a reduced level of inflammatory response, fewer infections, and fewer abdominal adhesions were reported when compared to the conventional non-absorbable materials. Because of their decreased rate of infections, biologic mesh materials are ideal for use in contaminated hernia repairs, including incarcerated bowels and removal of infected polypropylene mesh from a previous repair. In such instances, placement of a permanent mesh should be avoided because it results in unacceptably high infection rates (50-90%).[25, 29, 35] The reduced rate of infection associated with bioprostheses is thought to result from the absence of a permanent foreign material to which bacteria can adhere.

Another biologic material which has been successfully employed in hernia repair is porcine dermis (Permacol). Like SIS, porcine dermis is acellular, which results in low antigenicity, limited inflammatory response, and few adhesion formations. Porcine dermis also supports host cell infiltration and revascularization, making it a permanent repair with fully integrated tissue.[29, 38-40] Permacol was approved for use in abdominal wall reconstruction by the Food and Drug Administration in 2000, and has been used in the United Kingdom since 1998.[38] Porcine dermis most closely resembles human dermis, making it an attractive option for soft tissue repair. An advantage of Permacol over SIS is that the porcine dermal graft requires minimal rehydration before implantation,[38] a contrast to the 8- to 10-minute rehydration required for SIS grafts.[26, 35, 36] Permacol is cross-linked with diisocyanate which renders it more resistant to enzymatic degradation. This is an important attribute because one drawback of SIS and other biologic materials is that they are often resorbed too quickly by the body since they are more susceptible to enzymatic attack.[29]

Fixation Methods

Recent advancements in surgical techniques and mesh materials have resulted in reduced recurrence in hernia repair.[2, 10] However, it is suspected that the use of sutures, staples, or tacks for mesh fixation may be responsible for neural irritation and persistent pain.[8, 41] Although the use of intraperitoneal pressure to hold the mesh over the defect may be used to solve this problem,[11, 19] there is an increased risk of mesh dislocation, leading to inadequate overlap and a greater likelihood of recurrence. A new technique of using a fibrin sealant to secure a non-absorbable synthetic mesh in hernia repair has been recently reported.[42-44] While some level of success was demonstrated, it was noted that fibrin sealant could not adequately prevent mesh migration in some occasions,[42] which is likely due to the weak adhesive strength of the sealant. Additionally, the use of fibrin sealant requires mixing of its ingredients, which could complicate preparation and intra-operative workflow. Fortelny and colleagues reported the use of a cyanoacrylate adhesive (Glubran-II, Dahlhausen, Cologne, Germany) in mesh fixation.[45] While cyanoacrylate adhesives have significantly higher adhesive strength than fibrin-based adhesives, these investigators observed inhibition of tissue integration of the implant material combined with pronounced inflammatory response. Additionally, cyanoacrylate adhesive significantly reduced the elasticity of the mesh and abdominal wall, and impaired the biomechanical performance of the repair. Due to the release of toxic degradation products (formaldehyde), cyanoacrylates are not approved for general subcutaneous applications in the US.[46, 47] Thus, there continues to be a need for an improved and effective fixation device that not only secures the mesh to the abdominal wall, but also enhances the long-term biocompatibility of the repair.

Bioadhesive Construct

A thin adhesive film could be coated onto commercially available acellular porcine dermis, such as CollaMend or Permacol, to create an adhesive bioprosthesis (FIG. 1) for hernia repair. By combining the water-resistant adhesive properties of MAP-mimetic (mussel adhesive proteins) synthetic polymers with the biomechanical properties, bioinductive ability, and biodegradability of biological meshes, these bioadhesive prostheses can potentially replace existing non-adhesive synthetic or biologic meshes that are widely used for soft tissue repair. The adhesive coating can be tailored to degrade at a desired rate so that the whole adhesive bioprosthesis can be absorbed when its function is replaced by native tissue, while minimizing the long-term infection risk and patient discomfort commonly associated with currently available fixation methods. Additionally, it is envisioned that the bioadhesive construct can be used right out of the package with minimal preparation and thus potentially simplify surgical procedures.

A new series of biodegradable, biomimetic adhesive polymers will be synthesized and coated onto commercially available biologic mesh to create a bioadhesive bioprosthesis (also referred to herein as a bioadhesive construct). The adhesive films will be characterized and optimized for adhesion, and the adhesive properties of the bioadhesive prosthetic will be determined using lap shear adhesion tests and burst strength tests performed on a biological test substrate.

Performance of DOPA-Containing Adhesive Underwater

Figure 2:
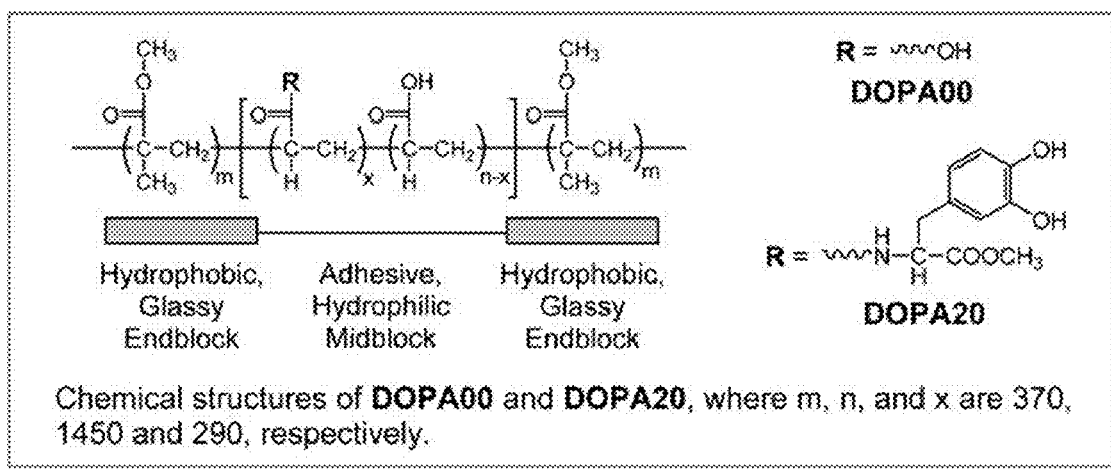
FIG. 2 provides suitable bioadhesive materials for a construct.

To mimic the water resistant adhesive properties of MAPs, DOPA was incorporated into poly(methyl methacrylate)-poly(methacrylic acid)-poly(methyl methacrylate) (PMMA-PMAA-PMMA) ABA triblock copolymers (A=PMMA and B=PMAA) and tested for adhesion. FIG. 2 shows the chemical structures of the base triblock copolymer (DOPA00) and the DOPA-containing adhesive polymer (DOPA20), where 20 mol % of methyl methacrylate units are modified with the catechol. These block copolymers consist of hydrophobic end-blocks and a hydrophilic midblock so that they rapidly self-assemble into water-swollen films in the presence of water. (See U.S. Ser. No. 11/676,099, filed Feb. 16, 2007 for exemplary preparation.)

New Biodegradable Medhesive Polymers

Figure 3:
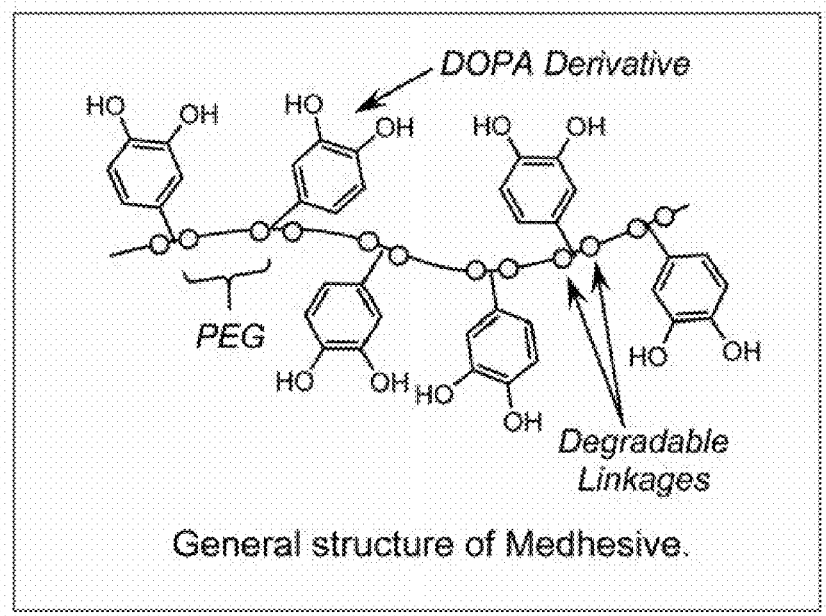
FIG. 3 is a general structure for one type of bioadhesive of the invention.

Although DOPA20 demonstrated strong water-resistant adhesion to biological tissue surfaces, this acrylate-based polymer is not easily biodegradable. The present invention provides a new series of adhesive polymers, Medhesive; their general chemical structure is shown in FIG. 3. These adhesive polymers were constructed from biocompatible PEG, which accounts for 42-92 wt %, and they were modified with DOPA derivatives such as dopamine and 3,4-dihydroxyhydrocinnamic acid (DOHA), both of which function as the cross-linking precursor as well as water-resistant adhesive moieties. Catechols account for 5-8 wt % in these adhesive polymers. Additionally, Medhesive polymers were prepared with degradable linkages (ester or urethane linkages) so that they could degrade into biocompatible degradation products (PEG, cross-linked catechol, etc.).

The primary degradation pathway of Medhesive is through hydrolysis. In vitro degradation of Medhesive was performed by incubating the cured Medhesive hydrogels in PBS (pH 7.4) at 37° C. and their percent dry weight loss was followed over time. As shown in FIG. 3, Medhesive-001, (PEE-4) which contains ester linkages throughout its polymer backbone, lost nearly 30 wt % of its dry mass after just one day of incubation and was completely degraded within five days. On the other hand, urethane-based Medhesives such as Medhesive-022 and Medhesive-026 lost only 10 and 23 wt % of their dry mass, respectively, after 77 days of incubation. (See FIG. 4.) By further engineering the polymer backbone of Medhesive polymers, it is expected to generate polymers that will degrade predictably over a span of weeks or months.

Figure 13:
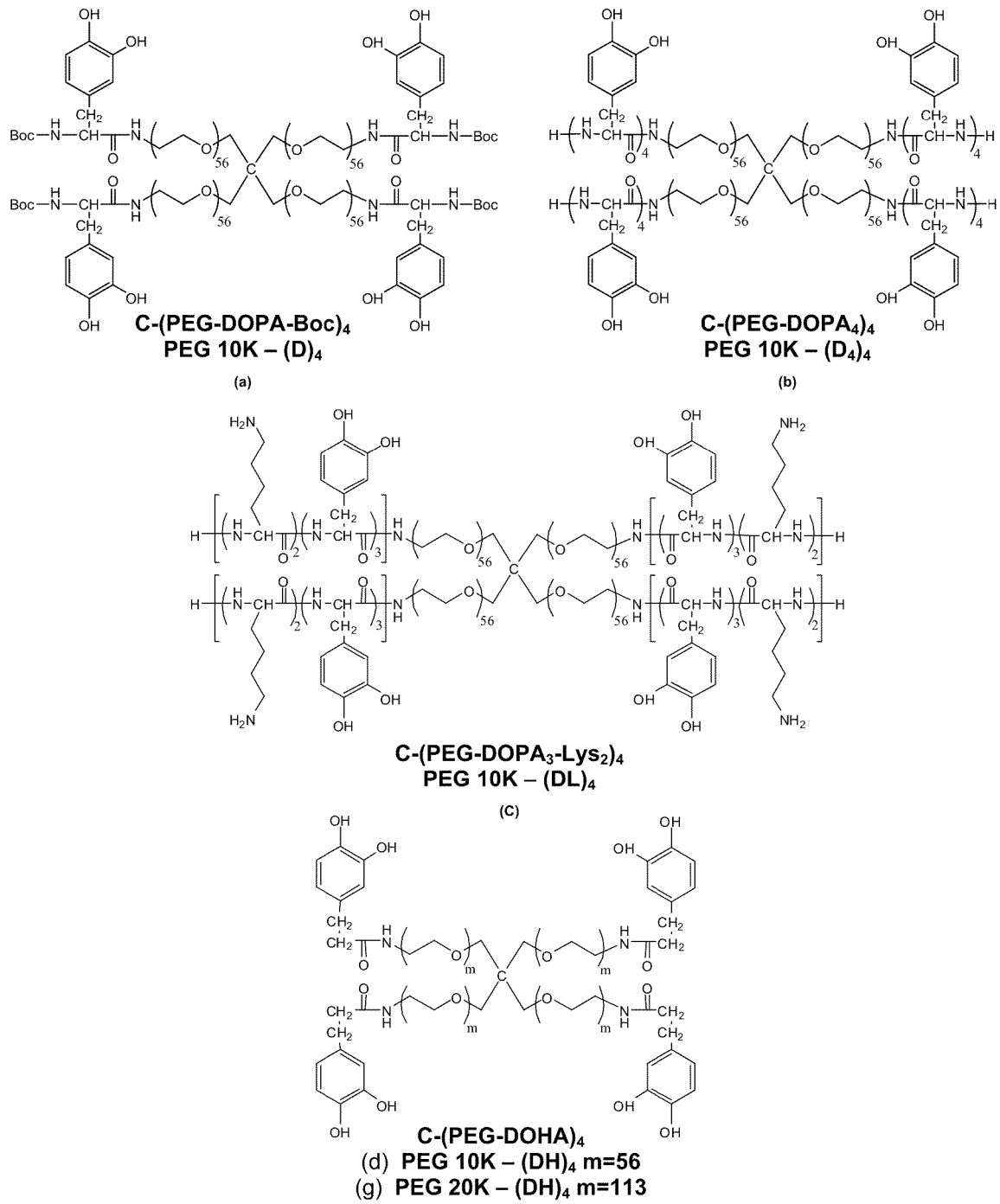
FIG. 13 provides chemical structure of several of the bioadhesive coatings.

These Medhesive polymers were tested to determine if they could function as a bioadhesive and tissue sealant, and compared their performance to a leading commercially available fibrin-based sealant (Tisseel V H, Baxter International, Inc.), a topical cyanoacrylate-based adhesive (Dermabond, Ethicon, Inc.), and QuadraSeal-DH (FIG. 13d), a PEG-based sealant developed by Nerites. Following procedures outlined in American Society for Testing and Materials (ASTM), lap shear (ASTM F2255)[81] and burst strength (ASTM F2392)[82] adhesion tests were performed using rehydrated collagen sheets (Nippi, Inc.) as the test substrate. All tests were performed within one hour of mixing with cross-linking reagent (NaIO$_4$) at a final polymer concentration of 15 wt %. As shown in FIG. 5, Medhesive demonstrated more than seven times the adhesion strength as compared to that of Tisseel. Only Dermabond demonstrated stronger adhesive strength compared to Medhesive. However, cyanoacrylate-based adhesives, like Dermabond, are approved only for topical usage due to cytotoxicity issues and poor mechanical compatibility with soft tissues.[83] On the other hand, preliminary biocompatibility tests and histological data performed on present adhesives revealed that they are relatively benign. Medhesive generally exhibited cohesive failure, indicating these adhesive formulations form relatively strong interfacial bonds with wetted collagen substrates while exhibiting relatively weak bulk mechanical properties. These hydrogel-based adhesives have very high water content (75-95 wt % water when fully swollen), which likely contributes to the observed cohesive failure. Further engineering may be needed to increase the mechanical properties of these adhesives to improve their bulk cohesive properties.

Proposed Adhesive Polymers to be Tested

The hydrophilic Medhesive polymers described above were designed to function as in situ curable tissue adhesives or sealants. Apart from their ability to form strong adhesive bonds to wetted, biological tissues, these adhesives were screened for easy preparation (i.e., fast solubilization) and rapid curing under biological conditions (i.e., humid environment, body temperature, etc.). However, these hydrogel-based adhesives have high water content and relatively weak bulk mechanical strength, which contributed to the observed cohesive failure in the adhesion tests. Therefore, for hernia repair the adhesive properties of DOPA-derivatives with a supporting substrate will be combined to have stronger mechanical properties, so that these repaired tissues can withstand the stresses associated with normal function and movement.

Table 1 and FIG. 6 show the composition and chemical structure, respectively, of the adhesive polymers to be used in conjunction with commercially available biologic meshes in the proposed research. These Medhesive polymers were constructed with a polymeric backbone consisting of amphiphilic multiblock copolymers of PEG and polycaprolactone (PCL). The presence of PEG allows the subsequent adhesive film to remain relatively hydrophilic to achieve good "wetting" or adhesive contact with the soft tissue substrate while the hydrophobic PCL segments increase cohesive strength and both prevent rapid dissolution of the film in the presence of water and reduce the rate of degradation. As these Medhesive polymers degrade, they will generate biocompatible degradation products (PEG, 6-hydroxyhexanoic acid, lysine, and cross-linked dopamine). Additionally, Medhesive-027 was prepared with a free lysyl amine group adjacent to dopamine. Lysine residues can potentially participate in intermolecular cross-linking with dopamine as well as promote interfacial binding of the adhesive film. The presence of the lysyl —NH$_2$ group renders the adjacent dihydroxyphenyl ring more hydrophilic, thus making it more accessible for adhesive contact. In addition to these two polymers, we will synthesize several other polymers to further optimize the adhesive properties of the proposed bioadhesive construct (Experiment 1).

TABLE 1

Composition of adhesive polymers

| Adhesive Polymer | PEG Content (wt %)[a] | PCL Content (wt %)[a] | Dopamine Content (wt %)[b] | Molecular Weight (Mw)[c] | Poly-dispersity[c] | Comments |
|---|---|---|---|---|---|---|
| Medhesive-024 | 62 | 25 | 8.0 | 17,000 | 1.1 | — |
| Medhesive-027[d] | 60 | 18 | 12 | 11,000 | 6.6 | Lysyl free —NH$_2$ |

[a] Determined from $^1$H NMR spectroscopy
[b] Determined from UV-vis spectroscopy[57]
[c] Determined from gel permeation chromatography in concert with laser light scattering (GPC-LS)
[d] May require further purification Experiment 1

Synthesize New Polymers with Improved Adhesive and Mechanical Properties

New dopamine-modified adhesive polymers similar to those shown in FIG. 6 will be synthesized. These new polymers will vary in their dopamine content, hydrophilicity or hydrophobicity, and branching, all of which strongly influence both the interfacial adhesive and bulk mechanical properties of the polymer film. For example, although the presence of catechol is important for water-resistant adhesive properties, polymeric films having a catechol content of 33 wt % have exhibited poor adhesion underwater. This is likely due to the hydrophobic nature of the dihydroxyphenyl ring, which becomes inaccessible when the hydrophobic polymeric film collapses in the presence of water. Therefore, the dopamine content of the new polymers will be kept between 10 and 20 wt %. Additionally, lysine residues with free —$NH_2$ groups will be incorporated adjacent to dopamine (similar to Medhesive-027, FIG. 6), which may render the adhesive moiety more hydrophilic and thus more accessible for adhesive contact. The hydrophilic or hydrophobic nature of the polymeric film will be further controlled by the PEG and PCL content, both of which will be kept between 40 and 60 wt %. While hydrophilicity is desirable for adhesive interaction, polymer films with high PEG content can swell excessively and have relatively lower mechanical strength. Additionally, hydrophilic films have a faster degradation rate compared to more hydrophobic films. Finally, 1-2 mol % of the linear PEG starting material will be replaced with a 4-armed PEG to introduce a branching point into an otherwise linear polymer, and thus to increase the molecular weight (MW) of the Medhesive polymer. Merely incorporating 1 mol % of branching can increase the MW by a factor of two [unpublished data]. The increased MW will foster polymer chain entanglement, which may enhance the cohesive properties of the polymer film. Each factor will be varied to obtain polymers that exhibit a good balance of adhesive and mechanical properties and to control the rate of degradation.

Protocol

The approach used to synthesize Medhesive-024 and Medhesive-027 will be modified slightly to prepare new Medhesive polymers.[90] These polymers are created by linking low MW polymers (PEG and PCL) with the two —$NH_2$ groups of lysine. Lysine also contains a carboxyl group for functionalization with dopamine. The MW of PEG and PCL used in the synthesis will influence the overall MW of the Medhesive polymers; starting polymers with relatively high MW will yield Medhesive polymers with a proportionally higher MW. The MW of both PEG and PCL will be varied between 400 and 2,000 Da. The hydrophilic and hydrophobic nature of Medhesive will be controlled by the ratio between PEG and PCL, so that each polymer accounts for 40-60 wt % in the resulting polymer. Finally, 1-2 mol % of the starting PEG polymer will be substituted with a 4-armed, 10,000 Da PEG to add branching points into Medhesive. These new Medhesive polymers will be characterized by nuclear magnetic resonance, UV-vis spectroscopy, and gel permeation chromatography to determine their composition and MW.

Anticipated Results/Alternative Approaches

It is anticipated that new Medhesive polymers with the desired composition (dopamine, PEG, and PCL content, branching) can be synthesized by modifying the protocols previously developed.[90] It is expected to synthesize Medhesive with a dopamine content of 10-20 wt %. It is expected that the MW of the starting polymer used will be inversely proportional to the dopamine content. For example, if 400-Da PEG and PCL were used in the reaction, the resulting Medhesive compound would have a theoretical dopamine content of 20 wt %. If 2,000-Da starting polymers were used, the theoretical dopamine content would be 7 wt %. Both the MW of the starting polymer and the extent of branching will be used to influence the MW of Medhesive, which can be expected to range from 10,000 to 100,000 Da.

Experiment 2

Coat a Thin Layer of Adhesive onto Biologic Mesh

Rationale

In this experiment, a method will be developed to spread a thin and even layer of adhesive film onto the biologic mesh. These adhesive coatings will consist of existing polymers shown in FIG. 6 as well as the new polymers to be synthesized in Experiment 1. The thickness of the coating will be optimized, since the overall thickness of the adhesive coating will significantly affect the cohesive properties of the film.[91] Typically, commercially available medical adhesive membranes are coated with 25-70 $g/m^2$ of adhesive depending on the targeted application,[92-96] which translates to approximately 25-70 μm of dry film thickness, assuming a polymer density of 1 $g/cm^3$. This thickness will be used as a range to guide in optimizing the thickness of the adhesive film. Commercially available cross-linked acellular porcine dermal tissues, such as CollaMend (C. R. Bard Inc., Cranston, R.I.) or Permacol (Tissue Science Laboratories, Andover, Mass.), will be used as the backing material. These meshes are chosen over other types of biologic materials, such as Surgisis (Cook Biotech, Inc., West Lafayette, Ind.), because the cross-linked dermis can provide a longer support to the wound due to a relatively slower degradation rate.[29]

In addition to coating the polymer onto a prosthetic or a patch, an oxidizing reagent (e.g., $NaIO_4$) can be embedded into the polymeric film as a way to introduce chemical cross-linking between the adhesive film and the tissue substrate. As the bioadhesive construct comes into contact with moist tissue substrate, the adhesive film will swell due to water uptake (FIG. 7A). This will in turn solubilize the oxidizing reagent, so that it oxidizes the catechol to quinone (FIG. 7B), which can participate in interfacial cross-linking reactions with the functional groups present on the tissue surface (FIG. 7C). Essentially, the bioadhesives of the invention can be activated when they come into contact with the moisture in soft tissue. For example, DOPA can be oxidized to form highly reactive quinone, which can undergo cross-linking reactions with different functional groups such as thiol (cysteine) or amine (lysine and histidine) groups, among others. While these oxidants are potential irritants, after undergoing the red-ox reaction with catechol, they transition to their reduced, benign form.

Protocol

Using procedures from ASTM standard D823,[97] an automated, motor-driven blade film applicator will be used to spread a even polymeric film onto the biologic mesh to create the adhesive bioprosthesis. The polymer is first dissolved in a relatively volatile solvent (such as methanol) to form a viscous solution that can be coated onto the biologic mesh. After the solvent evaporates, the dry adhesive film will remain on the bioprosthesis. Dry film thickness charts will be used as guidelines to determine how much material to use to obtain the desired dry film thickness.[98] For example, to create a dry film that is 2.5 mils (63.5 μm) thick from a 55 wt % polymeric solution, according to this chart, we would need to apply the coating at 353 square feet per gallon (87 $cm^2/mL$) to form a wet film thickness of 4.5 mils (114 μm). Standard procedures will be used to determine the thickness (ASTM D1005)[99] and the mass (ASTM F2217)[100] of deposited dried film using a micrometer and a balance, respectively. To coat a polymeric film with an oxidizing reagent embedded in the film, an oxidizing reagent such as $NaIO_4$ will be dissolved in a polar organic solvent and added to the polymer solution before the coating process.

Anticipated Results/Alternative Approaches

It is anticipated that dry films of the desired thickness can be evenly coated onto biologic mesh using ASTM procedures. The blade applicator was chosen over other methods described in ASTM D823 because this approach uses less material. If an even coating cannot be achieved using the blade applicator, spray or the dip coating methods as described in ASTM standard D823[97] can be used. Commercially available biologic meshes (cross-linked porcine dermal tissue) will be used as the backing materials for the bioadhesive mesh. Alternatively, cross-linked porcine skin or multi-layered laminates of collagen sheets will be constructed using published methods for use as the backing material.[101-103] The mechanical properties of these modified tissues will be characterized and compared to published results. Although these soft tissues may not have the exact mechanical properties as commercially available biologic meshes, they have similar surface properties, which allow us to develop coating and testing methods. It is anticipated that NaIO$_4$ can be added to the adhesive film without prematurely oxidizing the catechol during the coating step. DOPA-modified polymers and NaIO$_4$ can be dissolved together in a polar organic solvent (i.e., DMSO or DMF) and the catechol will remain in the reduced state until water replaces the organic solvent [unpublished data]. However, both DMF and DMSO have very high boiling points, so they might not be completely removed through evaporation. If this method is not successful in embedding NaIO$_4$, the oxidizing reagent can be introduced separately during subsequent experiments.

Experiment 3

Characterization of Polymeric Adhesive Film

Rationale

In this experiment, the adhesive films will be characterized by determining the extent to which they swell in an aqueous buffer, the contact angle of the film surface to evaluate its hydrophilicity, the in vitro rate of degradation, and their tensile mechanical properties. All of these properties are interrelated and will affect the overall performance of the adhesive film. For example, the more hydrophilic the film, the more water it can take up, causing it to swell more.[86] This in turn increases the rate of degradation through hydrolysis.[88, 89] Large amounts of swelling are less desirable if the goal is to make a more cohesive film.[87, 88] However, the surface of the adhesive film needs to maintain a certain level of hydrophilicity to support formation of good interfacial binding with a wetted tissue surface. Fully swollen, as opposed to dried, films will be used for the mechanical testing, because these films should be tested under conditions that closely resemble its behavior under physiological conditions. The effect of polymer composition, molecular weight, and amount of branching on the tensile properties of the films will be determined. Additionally, the effect of degradation on the mechanical properties will also be studied. While it is important to know when all of the materials are reabsorbed by the body, it is equally important to evaluate the mechanical stability of the adhesive joint over time. Finally, the effect of the oxidation on the adhesive film will also be examined.

Protocol

Four different tests will be performed to characterize the adhesive film. The polymer films will be created by drying the polymeric solutions in a mold. Swelling experiments will be performed using published procedures with some modifications.[86, 89] The pre-weighed dried film ($W_d$) will be submerged in phosphate buffered saline (PBS, pH 7.4) at 37° C. and its swollen mass ($W_s$) will be recorded after 24 h. The extent of the swelling will be defined by the equation: ($W_s-W_d$)/$W_s$. To determine the hydrophilicity of the film surface, advancing contact angle of a drop of water on the dried film will be measured using a goniometer. In vitro degradation of the adhesive film will be followed using published procedures.[89] The adhesive film will be submerged in PBS at 37° C.

At predetermined time points, one of the films will be removed, dried and weighed. The percent weight loss over time will be determined by $100 \times (W_o - W_t)/W_o$, where $W_o$ and $W_t$ are the measured dry mass before and after degradation, respectively. Uniaxial tensile properties of the adhesive film will be performed using procedures outlined in the literature with minor modifications.[87-89] The polymer film will be cast in a dog-bone shaped mold and swollen in PBS at 37° C. for 24 h. Using an Instron, the ultimate tensile strength (TS), Young's modulus (E), and elongation at break ($\epsilon_b$) will be measured. To further examine the effects of degradation on the mechanical properties of the film, tensile tests will be performed on films that have been incubated in PBS (37° C.) for several months. Finally, the effects of oxidative crosslinking on the film will also be determined. The oxidizing reagent-embedded film will be rehydrated in PBS at 37° C. for 24 h and the effect of oxidizing reagent on the extent of swelling, contact angle, and tensile properties will be measured.

Anticipated Results/Alternative Approaches

It is anticipated that the extent of swelling, contact angle measurements, rate of degradation, and mechanical properties of the adhesive film will be significantly affected by the composition of polymer film. For example, films consisting of multiblock copolymers of PEG and PCL have exhibited swelling of 1.3-fold to more than 5-fold depending on the PEG:PCL ratio.[86, 88, 89] The advancing contact angles of these films are 80° and 34° for PEG:PCL weight ratios of 10:90 and 60:40, respectively,[88] and it is expected that the measurements for the polymers will fit within this range. These PEG/PCL films have been reported to require at least 7 months (well beyond the 6-month grant period) to completely degrade in saline solutions.[88] Although it is expected that the adhesive film of the invention will behave similarly, the effect of the polymer composition on the rate of degradation can be studied. It is expected that the films of the invention will degrade through the hydrolysis of ester or urethane linkages in Medhesive polymer backbones. Although these polymers will also undergo enzyme-mediated degradation in vivo, in vitro studies will still provide useful information with regard to how the physical and mechanical properties of these adhesive films change with degradation.

While the tensile properties of dried films composed of multiblock copolymers of PEG and PCL have been reported (TS=6-50 MPa, $\epsilon_b$=100-1,000%, and E=7-160 MPa), obtaining similar data for fully hydrated films is often difficult. However, since one study reported that water uptake reduced the moduli of polymer films by 60-70%,[89] it is anticipated that the Young's modulus of the films will be in the range of $10^6$-$10^7$ Pa; this value is two to three orders of magnitude higher than that of the hydrogel-based adhesives.[57, 58] It is also expected that our adhesive films will be highly flexible and extensible from the reported high $\epsilon_b$ values of the dry films.[88, 89] While it is difficult to predict the effect of swelling on $\epsilon_b$, the adhesive polymers that consist of hydrophobic PCL blocks can form physical crosslinks in an aqueous environment. The reversible nature of these bonds will allow for dissipation of fracture energy which is required for the formation of a tough film. Toughness will be critical for these adhesives to be able to withstand the constant motions and forces experienced during daily activities of the patient. Finally, it is anticipated that introducing chemical crosslinking in the films, either through oxidative crosslinking or by increasing the extent of branching, may create a stiffer film with lower extensibility. Thus, there is a need to balance the bulk cohesive property and flexibility of the adhesive film.

Experiment 4

Adhesion Test with the Adhesive Bioprosthesis

Rationale

In the body, the bioadhesive prosthetic may be stretched and the adhesive film will experience shear forces. Therefore, lap shear adhesion tests will be performed to determine the adhesive properties of the biologic mesh coated with the new adhesives (FIG. 8A). Additionally, the bioprosthesis will need to withstand intra-abdominal pressures, which have been measured to be in the range of 64-252 mmHg during normal activity[104] and a burst strength test will also be performed (FIG. 8B). Either porcine skin or collagen membrane will be used as the test substrate to simulate attachment to soft tissue. The effects of various factors (i.e., dopamine content, hydrophilicity/hydrophobicity, branching, film mechanical properties, and oxidizing reagent) on the overall adhesive strength of the biologic prosthetic will be determined. The information obtained here will allow further optimization of the adhesive formulation for subsequent experiments.

Protocol

Procedures from ASTM standards will be used to perform lap shear (ASTM F2255)[81] and burst strength (ASTM F2392)[82] tests. Both the bioadhesive biologic mesh and the test substrate will be rehydrated before testing and then brought together to form an adhesive joint. The mesh and the substrate forming the adhesive joint will be kept in contact by placing a 1-kg weight over the joint while it is submerged in water (for hours to a day), so that the effect of contact time can be measured on adhesive strength. After the adhesive experiment, the detached adhesive joints will be visually inspected to determine the mode of failure. The performance of the proposed bioadhesive prosthetic will be compared to that of biologic meshes glued using a fibrin-based sealant (Tisseel V H, Baxter International, Inc.), a topical cyanoacrylate-based adhesive (Dermabond, Ethicon, Inc.), and PEG-based sealant (QuadraSeal-DH) (FIG. 13d) for evaluation purposes.

Anticipated Results/Alternative Approaches

It is anticipated that the adhesive strength of these adhesive biologic meshes will be significantly greater than that of the hydrogel-based adhesives (FIG. 5). Less than 25 wt % of the hydrogel-based adhesives is polymer, and their low polymeric content is one reason why hydrogels generally have weak cohesive strength. Similar PEG-based hydrogels have a modulus of $10^4$ Pa,[57, 58] whereas swollen polymeric films have demonstrated moduli that are two to three orders of magnitude higher.[89] Thus, if the catechols are properly oriented for interfacial binding, film-based adhesives will demonstrate significantly stronger adhesive strength than hydrogel-based adhesives. Additionally, it is expected that the introduction of the oxidizing reagent will strengthen the adhesive properties of the adhesive films. Although DOPA was the primary factor for strong binding with biological substrates under water, the formation of interfacial chemical bonds can further enhance the adhesive properties of the polymers. Presently, it is not known what kind of lap shear adhesive strength is needed to fixate a prosthesis for soft tissue repair, as this concept is quite new. However, fibrin-based sealants with relatively weak adhesive strength have demonstrate some level of success in fixating a synthetic mesh,[42-44] and it is expected that the adhesive strength of the bioadhesive bioprosthetics of the invention will range somewhere between that of fibrin sealants ($10^3$-$10^4$ Pa) and cyanoacrylate adhesives ($10^6$-$10^7$ Pa). If such adhesive strength can be achieved that is in the same order of magnitude or slightly lower ($10^5$-$10^6$ Pa) as that of cyanoacrylate adhesives, then the bioprosthetics of the invention have great potential in hernia repair. Maximum intra-abdominal pressures measured in normal activities in healthy individuals have been reported (64-252 mmHg);[104] these values will serve as the target value for the burst strength test. The bioadhesive prosthetics can potentially achieve and even exceed these values as the hydrogel-based adhesives have already demonstrated burst strengths in the same order of magnitude (80-140 mmHg, FIG. 5B).

BIBLIOGRAPHY

1. National Institute of Diabetes and Digestive and Kidney Diseases (NIDDK).
2. Arregui, M. E., Young, S. B., *Groin Hernia Repair by Laparoscopic Techniques: Current Status and Controversies*. World J. Surg., 2005. 29: p. 1052-1057.
3. Hay, J.-M., et al, *Shouldice Inguinal Hernia Repair in the Male Adult: The Gold Standard?* Annals of Surgery, 1995. 222(6): p. 719-727.
4. Neumayer, L., et. al., *Tension-Free Inguinal Hernia Repair: The Design of a Trial to Compare Open and Laparoscopic Surgical Techniques*. J Am Coll Surg, 2003. 196(5): p. 743-752.
5. Korenkov, M., Sauerland, S., Arndt, M., Bograd, L., Neugebauer, E. A. M., Troidl, H., *Randomized clinical trial of suture repair, polypropylene mesh or autodermal hernioplasty for incisional hernia*. British Journal of Surgery, 2002. 89: p. 50-56.
6. Luijendijk, R. W., et al, *A comparison of suture repair with mesh repair for incisional hernia*. The New England Journal of Medicine, 2000. 343(6): p. 392-398.
7. Novitsky, Y., Harrell A. G., Hope, W. W., Kercher, K. W., Heniford, B. T., *Meshes in Hernia Repair*. Surgical Technology International, 2007(16): p. 123-127.
8. Amid, P. K., *Groin Hernia Repair: Open Techniques*. World J. Surg., 2005. 29: p. 1046-1051.
9. Bax, T., Sheppard, B. C., Crass, R. A., *Surgical Options in the Management of Groin Hernias*. American Family Physician, 1999. 59(1).
10. Berndsen, F. H., et al, *Discomfort five years after laparoscopic and Shouldice inguinal hernia repair: a randomised trial with 867 patients*. Hernia, 2007.
11. Champault, G., Rizk, N., Catheline, J.-M., Barrat, C., Turner, R., Boutelier, P., *Inguinal Hernia Repair: Totally pre-peritoneal laparoscopic approach versus Stoppa operation*. Hernia, 1997. 1: p. 31-36.
12. Forte, A., D'Urso, A., Palumbo, P., Lo Storto, G., Gallinaro, M. S., Bezzi, M., Beltrami, V., *Inguinal hernioplasty: the gold standard of hernia repair*. Hernia, 2003. 7: p. 35-38.
13. Junge, K., Peiper, C., Rosch, R., Lynen, P., Schumpelick, V., *Effect of tension induced by Shouldice repair on postoperative course and long-term outcome*. Eur. J. Surg., 2002. 168: p. 329-333.
14. Juul, P., Christensen, K., *Randomized clinical trial of laparoscopic versus open inguinal hernia repair*. British Journal of Surgery, 1999. 86: p. 316-319.
15. Liem, M. S. L., et al, *Comparison of conventional anterior surgery and laparoscopic surgery for inguinal hernia repair*. The New England Journal of Medicine, 1997. 336 (22): p. 1541-1547.

16. Koniger, J., Redecke, J., Butters, M., *Chronic pain after hernia repair: a randomized trial comparing Shouldice, Lichtenstein and TAPP*. Langenbecks Arch. Surg., 2004. 389: p. 361-365.
17. Gilbert, A. I., Graham, M. F., Voigt, W. J., Inguinal Hernia: Anatomy and Management. 2000.
18. Peiper, C., Junge, K., Futing, A., Bassalay, P., Conze, J., Schumpelick, V., *Inguinal Tensile Strength and Pain Level after Shouldice Repair. Hernia,* 2001. 5: p. 129-134.
19. Gilbert, A. I., Graham, M. F., Voigt, W. J., *A bilayer patch device for inguinal hernia repair*. Hernia, 1999. 3: p. 161-166.
20. Amid, P. K., *Classification of biomaterials and their related complications in abdominal wall hernia surgery*. Hernia, 1997. 1: p. 15-21.
21. Neumayer, L., et. al., *Open mesh versus Laparoscopic mesh repair of inguinal hernia*. The New England Journal of Medicine, 2004. 350(18): p. 1819-1827.
22. Schwab, R., Eissele, S., Bruckner, U. B., Gebhard, F., Becker, H. P., *Systemic inflammatory response after endoscopic (TEP) versus Shouldice groin hernia repair*. Hernia, 2004. 8: p. 226-232.
23. Harrell, A. G., Novitsky, Yuri W., et al, *Prospective histologic evaluation of intra-abdominal prosthetics four months after implantation in a rabbit model*. Surg. Endosc., 2007. 21: p. 1170-1174.
24. Konstantinovic, M. L., Lagae, P., Zheng, F., Verbeken, E. K., De Ridder, D., Deprest, J. A., *Comparison of host response to polypropylene and non-cross-linked porcine small intestine serosal-derived collagen implants in a rat model*. BJOG: an International Journal of Obstetrics and Gynecology, 2005. 112: p. 1554-1560.
25. Franklin, M. E. J., Gonzalez, J. J. Jr., Glass, J. L., *Use of porcine small intestinal submucosa as a prosthetic device for laparoscopic repair of hernias in contaminated fields: 2 year follow-up*. Hernia, 2004. 8: p. 186-189.
26. Ko, R., et al, *Tensile strength comparison of small intestinal submucosa body wall repair*. Journal of Surgical Research, 2006. 135(1): p. 9-17.
27. Kiudelis, M., et al, *Effects of different kinds of meshes on postoperative adhesion formation in New Zealand White rabbit*. Hernia, 2007. 11: p. 19-23.
28. Sikkink, C. J. J. M., et al, *Adhesion formation and reherniation differ between meshes used for abdominal wall reconstruction*. Hernia, 2006. 10: p. 218-222.
29. Catena, F., Ansaloni, L., Gazzotti, F., Gagliardi, S., Di Saverio, S., D'Alessandro, L., Pinna, A. D., *Use of porcine dermal collagen graft (Permacol) for hernia repair in contaminated fields*. Hernia, 2007. 11: p. 57-60.
30. Engelsman, A. F., van der Mei, H. C., Ploeg, R. J., Busscher, H. J., *The phenomenon of infection with abdominal wall reconstruction*. Biomaterials, 2007. 28: p. 2314-2327.
31. Novitsky, Y. W., Harrell, Andrew G., et al, *Comparative evaluation of adhesion formation, strength of ingrowth, and textile properties of prosthetic meshes after long-term intra-abdominal implantation in a rabbit*. Journal of Surgical Research, 2007. 140(1): p. 6-11.
32. Novitsky, Y. W., Cristiano, J. A., Harrell, Andrew G., et al, *Immunohistochemical analysis of host reaction to heavyweight-, reduced-weight-, and expanded polytetrafluoroethylene (ePTFE)-based meshes after short-and long-term intraabdominal implantations*. Surg. Endosc., 2008.
33. Rauth, T. P., Poulose, B. K., Nanney, L. B., Holzman, M. D., *A Comparative Analysis of Expanded Polytetrafluoroethylene and Small Intestinal Submucosa—Implications for Patch Repair in Ventral Herniorrhaphy*. Journal of Surgical Research, 2007. 143(1): p. 43-49.
34. Oelschlager, B. K., Barreca, M., Chang, L., Pellegrini, C. A., *The use of small intestine submucosa in the repair of paraesophageal hernias: Initial observations of a new technique*. The American Journal of Surgery, 2003. 186: p. 4-8.
35. Ueno, T., Pickett, L. C., de la Fuente, S. G., Lawson, D. C., Pappas, T. N., *Clinical application of porcine small intestinal submucosa in the management of infected or potentially contaminated abdominal defects*. Journal of Gastrointestinal Surgery, 2004. 8(1): p. 109-112.
36. Ansaloni, L., Catena, F., Gagliardi, S., Gazzotti, F., D'Alessandro, L., Pinna, A. D., *Hernia repair with porcine small-intestinal submucosa*. Hernia, 2007. 11(4): p. 321-326.
37. Lantis, J. C. J., Gallivan, E. K., Hekier, R., Connolly, R., Schwaitzberg, S. D., *A comparison of collagen and PTFE patch repair in a rabbit model of congenital diaphragmatic hernia*. Journal of Investigative Surgery, 2000. 13: p. 319-325.
38. Parker, D. M., Armstrong, P. J., Frizzi, J. D., North, J. H. Jr, *Porcine Dermal Collagen (Permacol) for Abdominal Wall Reconstruction*. Current Surgery, 2006. 63(4): p. 255-258.
39. Shaikh, F. M., Giri, S. K., Durrani, S., Waldron, D., Grace, P. A., *Experience with porcine acellular dermal collagen implant in one-stage tension-free reconstruction of acute and chronic abdominal wall defects*. World J. Surg., 2007. 31: p. 1966-1972.
40. Smart, N., Immanuel, A., Mercer-Jones, M., *Laparoscopic repair of a Littre's hernia with porcine dermal collagen implant (Permacol)*. Hernia, 2007. 11: p. 373-376.
41. Stark, E., et al., *Nerve irritation after laparoscopic hernia repair*. Surg. Endosc., 1999 13(9): p. 878-81.
42. Olivier ten Hallers, E. J., Jansen, J. A., Manes, H. A. M., Rakhorst, G., Verkerke, G. J., *Histological assessment of titanium and polypropylene fiber mesh implantation with and without fibrin tissue glue*. Journal of Biomedical Materials Research Part A, 2006: p. 372-380.
43. Schwab, R., Willms, A., Kroger, A., Becker, H. P., *Less chronic pain following mesh fixation using fibrin sealant in TEP inguinal hernia repair*. Hernia, 2006. 10: p. 272-277.
44. Topart, P., Vandenbroucke, F., Lozac'h, P., *Tisseel vs tack staples as mesh fixation in totally extraperitoneal laparoscopic repair of groin hernias*. Surg. Endosc., 2005. 19: p. 724-727.
45. Fortelny, R. H., et al., *Cyanoacrylate tissue sealant impairs tissue integration of macroporous mesh in experimental hernia repair* Surgical Endoscopy, 2007. 21(10): p. 1781-1785.
46. Sierra, D. and R. Saltz, *Surgical Adhesives and Sealants: Current Technology and Applications*. 1996, Lancaster, Pa.: Technomic Publishing Company, Inc.
47. Ikada, Y., *Tissue adhesives*, in *Wound Closure Biomaterials and Devices*, C. C. Chu, J. A. von Fraunhofer, and H. P. Greisler, Editors. 1997, CRC Press, Inc.: Boca Raton, Fla. p. 317-346.
48. Waite, J. H., *Nature's underwater adhesive specialist*. Int. J. Adhes. Adhes., 1987. 7(1): p. 9-14.
49. Yamamoto, H., *Marine adhesive proteins and some biotechnological applications*. Biotechnol. Genet. Eng. Rev., 1996. 13: p. 133-65.
50. Kramer, K. J., et al., *Insect cuticle tanning: Enzymes and cross-link structure*, in *Natural Occurring Pest Bioregulators*. 1991. p. 87-105.

51. Yu, M., J. Hwang, and T. J. Deming, *Role of L-3,4-dihydroxyphenylanine in mussel adhesive proteins*. JACS, 1999. 121(24): p. 5825-5826.
52. Deming, T. J., M. Yu, and J. Hwang, *Mechanical studies of adhesion and crosslinkning in marine adhesive protein analogs*. Polym. Mater. Sci. Eng., 1999. 80: p. 471-472.
53. Waite, J. H., *Mussel beards: A coming of Age*. Chem. Ind., 1991. 2 September: p. 607-611.
54. Papov, V. V., et al., *Hydroxyarginine-containing polyphenolic proteins in the adhesive plaques of the marine mussel Mytilus edulis*. J. Biol. Chem., 1995. 270(34): p. 20183-92.
55. Waite, J. H. and X. Qin, *Polyphosphoprotein from the Adhesive Pads of Mytilus edulis. Biochem.*, 2001. 40(9): p. 2887-93.
56. Yu, M. and T. J. Deming, *Synthetic polypeptide mimics of marine adhesives*. Macromol., 1998. 31(15): p. 4739-45.
57. Lee, B. P., et al., *Rapid Photocurable of Amphiphilic Block Copolymers Hydrogels with High DOPA Contents*. Maclomolecules, 2006. 39: p. 1740-48.
58. Lee, B. P., J. L. Dalsin, and P. B. Messersmith, *Synthesis and Gelation of DOPA-Modified Poly(ethylene glycol) Hydrogels*. Biomacromol., 2002. 3(5): p. 1038-47.
59. Sagert, J., C. Sun, and J. H. Waite, *Chemical Subtleties of Mussel and Polychaete Holdfasts*, in *Biological Adheisves*, A. M. Smith and J. A. Callow, Editors. 2006, Springer-Verlag. p. 125-143.
60. Waite, J. H., *The phylogeny and chemical diversity of quinone-tanned glues and varnishes*. Comp. Biochem. Physiol. B., 1990. 97(1): p. 19-29.
61. Waite, J. H., *Reverse engineering of bioadhesion in marine mussels*. Ann. N.Y. Acad. Sci., 1999. 875: p. 301-9.
62. Deacon, M. P., et al., *Structure and Mucoadhesion of Mussel Glue Protein in Dilute Solution*. Biochem., 1998. 37(40): p. 14108-14112.
63. Huang, K., et al., *Synthesis and Characterization of Self-Assembling Block Copolymers Containing Bioadhesive End Groups*. Biomacromol., 2002. 3(2): p. 397-406.
64. Schnurrer, J. and C.-M. Lehr, *Mucoadhesive properties of the mussel adhesive protein*. Int. J. Pharm., 1996. 141(1,2): p. 251-256.
65. Chirdon, W. M., W. J. O'Brien, and R. E. Robertson, *Adsorption of catechol and comparative solutes on hydroxyapatite*. J. Biomed. Mat. Res. B, 2003. 66B(2): p. 532-538.
66. Dalsin, J. L., et al., *Mussel Adhesive Protein Mimetic Polymers for the Preparation of Nonfouling Surfaces*. JACS, 2003. 125: p. 4253-4258.
67. Dalsin, J. L., L. Lin, and P. B. Messersmith, *Antifouling performance of poly(ethylene glycol) anchored onto surfaces by mussel adhesive protein mimetic peptides*. Polym. Mater. Sci. Eng., 2004. 90: p. 247-248.
68. Dalsin, J. L., et al., *Protein Resistance of Titanium Oxide Surfaces Modified by Biologically Inspired mPEG-DOPA*. Langmuir, 2005. 21(2): p. 640-646.
69. Sugumaran, M., H. Dali, and V. Semensi, *Chemical-and cuticular phenoloxidase-mediated synthesis of cysteinyl-catechol adducts*. Arch. Insect Biochem. Physiol., 1989. 11(2): p. 127-37.
70. Lee, H., N. F. Scherer, and P. B. Messersmith, *Single Molecule Mechanics of Mussel Adhesion*. Proc. Natl. Acad. Sci., 2006. 103: p. 12999-13003.
71. Waite, J. H. and S. O. Andersen, *3,4-Dihydroxyphenylalanine in an insoluble shell protein of Mytilus edulis*. Biochim. Biophys. Acta, 1978. 541(1): p. 107-14.
72. Pardo, J., et al., *Purification of adhesive proteins from mussels*. Protein Expr. Purif., 1990. 1(2): p. 147-50.
73. Maugh, K. J., et al., *Recombinant bioadhesive proteins of marine animals and their use in adhesive compositions*, in Genex Corp. 1988: USA. p. 124.
74. Strausberg, R. L., et al., *Development of a microbial system for production of mussel adhesive protein*, in *Adhesives from Renewable Resources*. 1989. p. 453-464.
75. Filpula, D. R., et al., *Structural and functional repetition in a marine mussel adhesive protein*. Biotechnol. Prog., 1990. 6(3): p. 171-7.
76. Yamamoto, H., *Adhesive studies of synthetic polypeptides: a model for marine adhesive proteins*. J. Adhes. Sci. Technol., 1987. 1(2): p. 177-83.
77. Yamamoto, H., S. Yamauchi, and S. Ohara, *Synthesis and adhesive studies of marine adhesive proteins of the Chilean Mussel Aulacomya ater*. Biomimetics, 1992. 1(3): p. 219-38.
78. Yamamoto, H. and K. Ohkawa, *Synthesis of adhesive protein from the vitellaria of the liver fluke Fasciola hepatica*. Amino Acids, 1993. 5(1): p. 71-5.
79. Lee, B. P., et al., *Synthesis of 3,4-Dihydroxyphenylalanine (DOPA) Containing Monomers and Their Copolymerization with PEG-Diacrylate to from Hydrogels*. J. Biomater. Sci., Polym. Ed., 2004. 15: p. 449-464.
80. Burke, S. A., et al., *Thermal gelation and tissue adhesion of biomimetic hydrogels*. Biomed. Mater., 2007. 2: p. 203-210.
81. ASTM-F2255, *Standard Test Method for Strength Properties of Tissue Adhesives in Lap-Shear by Tension Loading*. 2003.
82. ASTM-F2392, Standard Test Method for Burst Strength of Surgical Sealants 2004.
83. Refojo, M. F., C. H. Dohlman, and J. Koliopoulos, *Adhesives in opthalmology: a review*. Surv. Ophthamol., 1971. 15(4): p. 217-36.
84. Guvendiren, M., P. B. Messersmith, and K. R. Shull. *Adhesion of DOPA-Functional Methacrylic Membranes in 31st Annual Meeting of the Adhesion Society*. 2008. Austin, Tex.
85. Guvendiren, M., P. B. Messersmith, and K. R. Shull, *Self-Assembly and Adhesion of DOPA-Modified Methacrylic Triblock Hydrogels*. Biomacromol., 2008. 9(1): p. 122-128.
86. Cohn, D., et al., *Biodegradable poly(ethylene oxide)/poly(e-caprolactone) multiblock copolymers*. J. Biomed. Mat. Res., 2002. 59(2): p. 273-281.
87. Bae, Y. H., et al., *Biodegradable amphiphilic multiblock copolymers and their implications for biomedical applications*. J. Controlled Release 2000. 64(1-3): p. 3-13.
88. Gorna, K. and S. Gogolewski, *Biodegradable polyurethanes for implants. II. In vitro degradation and calcification of materials from poly(e-caprolactone)-poly(ethylene oxide) diols and various chain extenders*. J. Biomed. Mat. Res., 2002. 60(4): p. 592-606.
89. Nagata, M. and I. Kitazima, *Photocurable biodegradable poly(epsilon-caprolactone)/poly(ethylene glycol) multiblock copolymers showing shape-memory properties* Colloid & Polymer Science, 2006. 284: p. 380-386.
90. Lee, B. P., *Biomimetic Compounds and Synthetic Methods Therefor.* 2008: WO 2008019352.
91. Minghetti, P., F. Cilurzo, and A. Casiraghi, *Measuring adhesive performance in transdermal delivery systems*. American Journal of Drug Delivery, 2004. 2(3): p. 193-206.
92. *MED 5030 Product Information Bulletin.* Avery-Dennison.
93. Nho, K., et al., *PEG-modified hemoglobin as an oxygen carrier*, in *Poly(ethylene glycol) chemistry: biotechnical* and *biomedical applications*, J. M. Harris, Editor. 1992, Plenum Press: New York. p. 171-182.
94. *ARcare® 90446 Product Data Sheet*. Adhesive Research Inc., 2004.
95. *ARcare® 90339 Product Data Sheet*. Adhesive Research Inc., 2004.
96. Jaschke, A., *Oligonucleotide-poly(ethylene glycol) conjugates: synthesis, properties, and applications*, in *Poly (ethylene glycol): chemistry and biological applications*, J. M. Harris and S. Zalipsky, Editors. 1997, American Chemical Society: Washington, D. C. p. 265-283.
97. ASTM-D823, *Standard Practicese for Producing Films of Uniform Thickness of Paint, Varnish, and Related Products on Test Panels*. 2001.
98. Schacht, E. H. and K. Hoste, *Poly(ethylene glycol)-grafted polymers as drug carriers*, in *Poly(ethylene glycol): chemistry and biological applications*, J. M. Harris and S. Zalipsky, Editors. 1997, American Chemical Society: Washington, D. C. p. 297-315.
99. ASTM-D 1005, *Standard Test Method for Measurement of Dry-Film Thickness of Organic Coatings Using Micrometers*. 2001.
100. ASTM-F2217, *Standard Practice for Coating/Adhesive Weight Determination*. 2007.
101. Khor, E., *Methods for the treatment of collagenous tissues for bioprostheses*. Biomaterials, 1997 18(2): p. 95-105.
102. Gloeckner, D. C., Sacks, M. S., Billiar, K. L., Bachrach, N., *Mechanical evaluation and design of a multilayered collagenous repair biomaterial*. J. Biomed. Mater. Res., 2000. 52: p. 365-373.
103. Billiar, K., Murray, J., Laude, D., Abraham, G., Bachrach, N., *Effects of carbodiimide crosslinking conditions on the physical properties of laminated intestinal submucosa*. J. Biomed. Mater. Res., 2001. 56: p. 101-108.
104. Cobb, W. S., et al., *Normal intraabdominal pressure in healthy adults*. The Journal of Surgical Research, 2005. 129(2): p. 231-5.

Tendon and Ligament Repair

Tendon and Ligament Injuries

Tendon and ligament injuries have been occurring with increasing frequency over the last several decades. Numerous factors contribute to this rise: an increase in the average age of the population along with medical advances that enable an aging population to participate in recreational sports.[1, 2] While most tendon and ligament injuries occur during participation in athletic activities, several underlying causes may make an injury more likely in certain individuals due to tissue weakening: tendon degeneration from impaired vascular supply and blood flow, drug use (anabolic hormone abuse among athletes, fluoroquinolone antibacterials, corticosteroid use either systematically or locally), and systemic or genetic disease.[2-4] Tendon and ligament injuries are of major clinical concern as no single agreed-upon successful treatment method exists, and no current treatment method can restore an injured tendon or ligament to its normal level of function.[3]

Three of the most commonly injured tendons and ligaments are the Achilles tendon, the anterior cruciate ligament (ACL), and the rotator cuff tendon. The Achilles tendon is ruptured more frequently than other tendons, and accounts for 40% of all operative tendon repairs. About 75% of cases can be attributed to participation in sports.[2, 5, 6] In Finland, the incidence of total Achilles ruptures increased from 4.2/100,000 inhabitants during 1979-1990 to 15.2/100,000 inhabitants during 1991-2000.[7] ACL reconstruction is one of the most commonly performed orthopedic operations.[8, 9] In the United States alone, an estimated 50,000 acute ACL reconstructions are performed annually.[10] As much as 65% of all ACL injuries occur during participation in a sport.[11] Rotator cuff repair is one of the most common surgical procedures performed on the shoulder.[1, 12] Injuries to the rotator cuff can occur in both young and old patients, but generally for different reasons. Most young patients are athletes who experienced a trauma while participating in a sport, while injuries in elderly patients usually result from degenerative changes.[13]

Current Fixation Methods

Treatment for tendon and ligament injuries varies for different tissues, but can be divided into two general categories: non-operative (conservative) and operative treatment. Operative treatment can be further divided into primary repair (suture), augmented repair (suture plus graft material), and reconstruction (autograft, allograft, or xenograft) of the injured tissue. There is a great deal of controversy within the orthopedic community over which repair method yields the most favorable results. Conservative treatment avoids the risk of complications associated with surgical repair (e.g., infection); however, conservative treatment is associated with an unacceptably high incidence (as much as 30%) of rerupture. [6, 7, 14, 15]

Operative treatment: primary repair. Primary repair of ruptured Achilles tendons has resulted in partial or complete reruptures in 1.4-4.8% of patients.[6, 15, 16] Likewise, primary repair of an acutely torn ACL often produces an unsatisfactory outcome, with as many as 40-50% of primary repairs failing within five years of treatment.[10, 17] Unsatisfactory results after a primary rotator cuff repair maybe as high as 25%.[18] The suture-tendon junction is usually the weak link in tendon primary repairs, due to the structure of tendinous tissue: the strength between the fibers is much less than that of the fibers themselves, so sutures can tear through the tendon when force is applied.[19] For primary repairs of rotator cuff injuries, the weak link is generally the bone-tendon interface because bones weakened by age and disease are often not able to support sutures and/or suture anchors. [12, 13, 20] In one study comparing fixation strength and failure mode for various rotator cuff repair techniques, nearly 70% of all control samples (primary repair using two transosseous sutures) failed due to the suture knot tearing through the cancellous bone. This group of failed repairs all had weak initial bone stock.[13] Another method for attaching rotator cuff tendon to the bone is through the use of suture anchors. This method is also plagued with problems, as patients suffering from osteoporosis often do not have strong enough bones to hold suture anchors in place. Loosened suture anchors can then lead to formation of a tendon-bone gap which inhibits healing, and ultimately, failure of the rotator cuff repair.[20] One study reported 10% of patients required a second operation due to loosening or pull-out of suture anchors.[18]

Operative treatment: surgical augmentation and reconstruction. Although primary repair is easier to perform, surgical augmentation provides a stronger repair, allows for more intensive rehabilitation, and decreases the rerupture rate.

Achilles tendon repairs. Several methods to reinforce the repair of Achilles tendons exist. These include: folding down one (Silfverskiold technique) or two (Lindholm technique) flaps from the gastrocnemius muscle[7, 14, 15], fanning out the plantaris tendon into a reinforcing membrane to be wrapped around the repaired tendon (Lynn technique)[21], using Gore-Tex® (PTFE) Soft Tissue Patch, bovine pericardium, Graftjacket™[19], and a Dacron vascular graft.[4] Reconstruction is often needed in Achilles tendon repair when the injury has been misdiagnosed or neglected for a period of time. A neglected Achilles rupture poses a problem for surgical repair due to gap formation from tendon shrinkage and/or scar tissue formation at the rupture site, making primary repair not a viable surgical option. In these instances, surgeons have used graft materials such as: Achilles tendon allografts, Marlex mesh, a polymer of lactic acid, carbon fibers, flexor tendons, and fascia lata auto- or allografts to bridge the gap of the ruptured tissue. [2] While graft materials improve the strength of tendon repair over suture alone, they do not eliminate the use of suture in the repair because the grafts need to be sutured in place. Therefore, there is still a risk of suture pull-through in an augmented or reconstructed repair, albeit a lesser risk since the graft material increases the area or 'footprint' of contact between tissue and suture.

ACL repairs. ACL tears are generally not repaired with sutures, because suturing fails over time. Instead, a torn ACL is most often replaced by a substitute graft made from a tendon. The two most commonly used grafts are patellar tendon autografts and hamstring tendon autografts. Both methods have their respective strengths and weaknesses, however; regardless of the choice of graft type, the main factor influencing the structural strength of the repair is the point of fixation of the graft to the bone.[9, 10, 17]

Rotator cuff repairs. Rotator cuff repairs often must be reinforced at the site of fixation to the bone due to weakening of the bone in elderly patients. Even in younger patients with healthy bone, strengthening the attachment of cuff tendon to the bone is desirable, because it permits more aggressive rehabilitation. The reinforcement is accomplished by distributing the force concentrated at the suture interfaces over a larger surface area by using a biocompatible patch.[13] Methods of augmentation include a Gore-Tex® (PTFE) patch between suture and bone, a Gore-Tex® patch between suture and bone and between suture and tendon, an Ethicon polydioxanone (PDS) band between suture and bone, application of a Zimmer® Collagen Repair Patch (porcine dermal tissue) over a suture repair, and application of a Restore™ Orthobiologic Implant (small intestine submucosa) over a suture repair.[12, 13, 22-24] Such patches can also be used to repair torn rotator cuffs where the tear is too large to be sutured.

Post-Operative Treatment—the Benefits of Early Rehabilitation

The final outcome of a tendon or ligament repair depends not only on the quality of the repair, but also on the post-operative treatment the patient receives.[25] The orthopedic community agrees that some period of ankle immobilization is required after Achilles tendon injury and repair, regardless of method of treatment used. However, there is much discussion as to how much is appropriate. Conventional post-operative treatment for surgically repaired Achilles tendons has meant immobilization in a below-the-knee plaster cast for six to eight weeks with little to no weightbearing.[7, 15, 16] Complications of prolonged immobilization include arthrofibrosis, calf atrophy, deep vein thrombosis, skin necrosis, and adhesions between skin and underlying tissues (a concern with graft materials or tendon flaps). Also, cast immobilization leads to lengthy rehabilitation of the leg. Recently, with stronger repairs due to improved surgical techniques, early mobilization has been found to enhance the healing process of the Achilles tendon. Immediately following surgery, a splint is applied to immobilize the foot and ankle After 1-5 days, this splint is replaced with an orthotic boot that permits a passive range of motion and full weightbearing. The orthotic boot is generally worn for 4-6 weeks, after which patients gradually resume normal activity as physical comfort permits. Tension applied to the tendon during healing improves the orientation of collagen fibers and calf muscle strength. [25, 26] Similar evidence supports employing early functional rehabilitation following surgery for ACL reconstruction[9, 10, 17] and rotator cuff repair[13, 24].

Collagen Membrane for Soft Tissue Repair

Collagen, one of the most abundant proteins in mammals, is present in connective tissues of primary mechanical function. [27] Collagen fibers have great tensile strength, and are the main component in tendons, ligaments, cartilage, skin, bone and teeth. Natural collagenous extracellular matrices harvested from animal dermis, pericardium, or small intestinal submucosa (SIS) have been utilized in various surgical procedures including hernia repair,[28] rotator cuff augmentation,[12, 29] and Achilles tendon repair.[30, 31] Various FDA-cleared products are currently available for soft tissue repair and reinforcement, including CuffPatch™ (Arthrotek, Warsaw, Ind.), Restore® (DePuy Orthopaedics, Warsaw, Ind.), Zimmer™ Collagen Repair Patch (Zimmer, Warsaw, Ind.). A primary reason why collagen membranes are selected for these therapeutic applications is their favorable mechanical properties, owing to the presence of self-aggregated and cross-linked collagen fibers.[32] Additionally, collagen membranes are non-toxic, biocompatible, and elicit a minimal immune response.[33] Furthermore, these biological membranes are readily biodegradable and reabsorbable. As degradation proceeds, host tissue in-growth and remodeling of the wound have resulted in the formation of functional tendons or ligaments as demonstrated in several preclinical animal models.[30, 31, 34-36] Xenografts that slowly degrade or are non-degradable are typically associated with the presence of foreign-body giant cells, chronic inflammation, and the accumulation of dense, poorly organized fibrous tissue.[31, 37] Finally, manipulation of collagen membranes has been widely reported and extensively characterized because the mechanical properties and rate of biodegradation of collagen sheets can be easily tailored through chemical cross-linking, multilayer lamination, or amino acid side chain modification.[38-41]

Novel Bioadhesive Collagen Tape

Figures 9, 10:
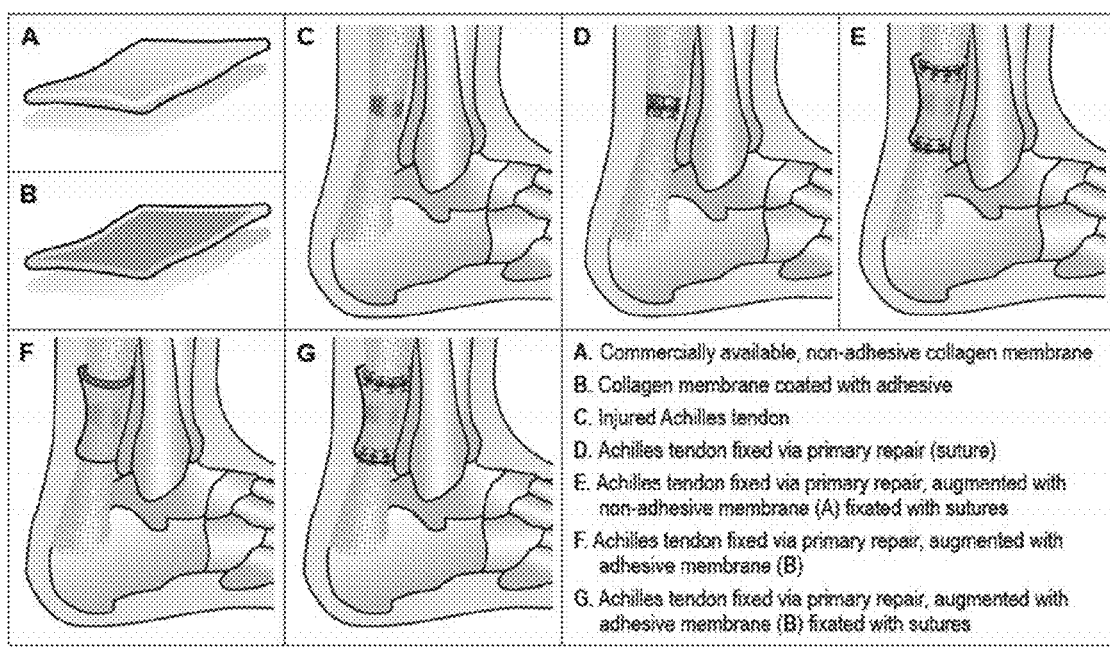
FIG. 9 provides examples of how a bioadhesive construct can be applied to a tendon.
FIG. 10 left intentionally blank.

A thin adhesive film can be coated onto collagen membranes to create a bioadhesive collagen tape that can be used as an augmentation device for tendon and ligament repair as illustrated in FIG. 9. By combining the water-resistant adhesive properties of MAP-mimetic (mussel adhesive protein) synthetic polymers with the biomechanical properties, bioinductive ability, and biodegradability of collagen membranes, these bioadhesive collagen tapes can potentially replace existing non-adhesive collagen patches that have been widely used for soft tissue repair. All currently available xenografts are affixed through the use of sutures. However, in some situations suturing might not be practical (i.e., massive rotator cuff tears, degenerative bone disorders, chronic shoulder injury, and neglected tendon tears where scar tissue has formed). [2, 12, 20] The only published literature that is remotely similar to the present invention includes combined gelatin-resorcinol-formaldehyde (GRF) glue and a collagen sheet to be used as a sutureless device for cardiovascular anastomosis.[68] Although wound closure was successful in a canine model, using formaldehyde as the cross-linking reagent is not desirable due to toxicity concerns, and GRF adhesives have not been approved by the FDA for clinical use in the US.[45] Additionally, curing the GRF glue requires mixing the ingredients, which could complicate preparation and intra-operative workflow. In contrast, the present strategy employs a prefabricated adhesive-coated membrane that would require only minimal preparation before use.

The proposed adhesive collagen tape can potentially be affixed to connective tissue without sutures or with minimal suturing as shown in FIG. 9-F and 9-G, respectively. By adhering the entire graft surface to the tendon or ligament, the stress on the wound is dispersed throughout a larger surface area, not localized at a small number of suture points used to fasten a non-adhesive patch. Thus, a much lower adhesive strength as compared to the tensile strength of the sutures may be sufficient to hold the patch intact. It is hypothesized that an augmentation device affixed using a bioadhesive could potentially better secure the wound, and thereby enable the patient to begin post-operative rehabilitation much sooner with a minimized chance of re-rupturing the tendon or ligament. Many studies have shown that application of tension shortly after surgical procedures is critical in regenerating well organized and functional collagen fibers in Achilles tendon repair, [25, 26, 30] ACL reconstruction,[9, 10, 17] and rotator cuff repair.[13, 24] Thus, early mobilization and partial load bearing may be essential to full recovery using an adhesive augmentation device.

A new series of biodegradable, biomimetic adhesive polymers will be coated onto collagen membranes to create a bioadhesive collagen tape. The tape will rely upon the strong tensile strength of the collagen membranes to hold a torn Achilles tendon intact. Equally important, the adhesive film on the relatively large surface area of the tape will transfer various mechanical stresses placed on the injured tendon to the collagen. The bioadhesive collagen tape will be characterized to see if it can function as an augmentation device to tendon and ligament repair by comparing it with conventional tendon and ligament repair methods (sutures), as well as with non-adhesive collagen patches.

Potential Commercial Applications

The bioadhesive collagen tapes proposed herein can potentially have great impact on how tendon or ligament repair is performed. It is envisioned that these constructs can potentially simplify surgical procedures, because a minimal number of sutures (or none at all) is needed to secure the wound. If the proposed adhesive tape is successful in tendon and ligament surgeries, similar material can potentially be applied in the repair of other soft tissues (i.e., hernia, and cardiovascular repair).

Preliminary Studies

Adhesion Test Performed on Collagen Sheet

Synthetic adhesive polymers, nerites-1 through nerites-4, were developed at Nerites Corporation (Nerites); their compositions are summarized in Table 1. These adhesive polymers were constructed from biocompatible PEG, which accounts for 42-92 wt %. These polymers are modified with derivatives of DOPA such as dopamine and 3,4-dihydroxyhydrocinnamic acid (DOHA), both of which function as the cross-linking precursor as well as water-resistant adhesive moieties. Catechols account for 5-8 wt % in these adhesive polymers. Apart from Nerites-4, these polymers are readily soluble in aqueous buffer at concentrations as high as 600 mg/mL. Nerites-4 consists of multiblock copolymers of PEG and hydrophobic polypropylene glycol (PPG), which needs to be kept close to the freezing temperature of water (0-5° C.) to remain soluble. Polymeric solutions of Nerites-4 behave like other amphiphilic block copolymers, such as Pluronic, that are capable of temperature- and concentration-dependent physical gel formation.

TABLE 1

Composition of adhesive polymers

| Adhesive Polymer | PEG Content (wt %)[a] | Catechol Content (wt %)[b] | Catechol Type | Hydrolysable Linkage | Comments |
|---|---|---|---|---|---|
| Nerites-1 | 92 | 7.8 | DOHA | Amide | Branch architecture |
| Nerites-2 | 73 | 8.2 | Dopamine | Urethane | Lysyl free —NH$_2$ |
| Nerites-3 | 88 | 6.5 | Dopamine | Urethane | — |
| Nerites-4 | 43 | 4.8 | Dopamine | Urethane | 43 wt % PPG |

[a] Determined by $^1$H NMR
[b] Determined from UV-vis[55]

Adhesives of the invention were cured by mixing the precursor solution with an equal volume of a cross-linking reagent (10-12 mg/mL of NaIO$_4$). The curing time can be controlled to occur from seconds to hours after mixing, with the optimized formulations capable of solidifying within seconds upon mixing. These adhesive polymers were tested to determine if they could function as a bioadhesive and tissue sealant, and compared their performance to a leading commercially available fibrin-based sealant (Tisseel V H, Baxter International, Inc.) and a topical cyanoacrylate-based adhesive (Dermabond, Ethicon, Inc.). Using rehydrated collagen sheets (Nippi, Inc.) as the test substrate, lap shear,[77] T-peel, [78] and burst strength[79] adhesion tests were performed using American Society for Testing and Materials (ASTM) standard test methods. All tests were performed within one hour of mixing with cross-linking reagent at a final polymer concentration of 15 wt %.

Figure 11:
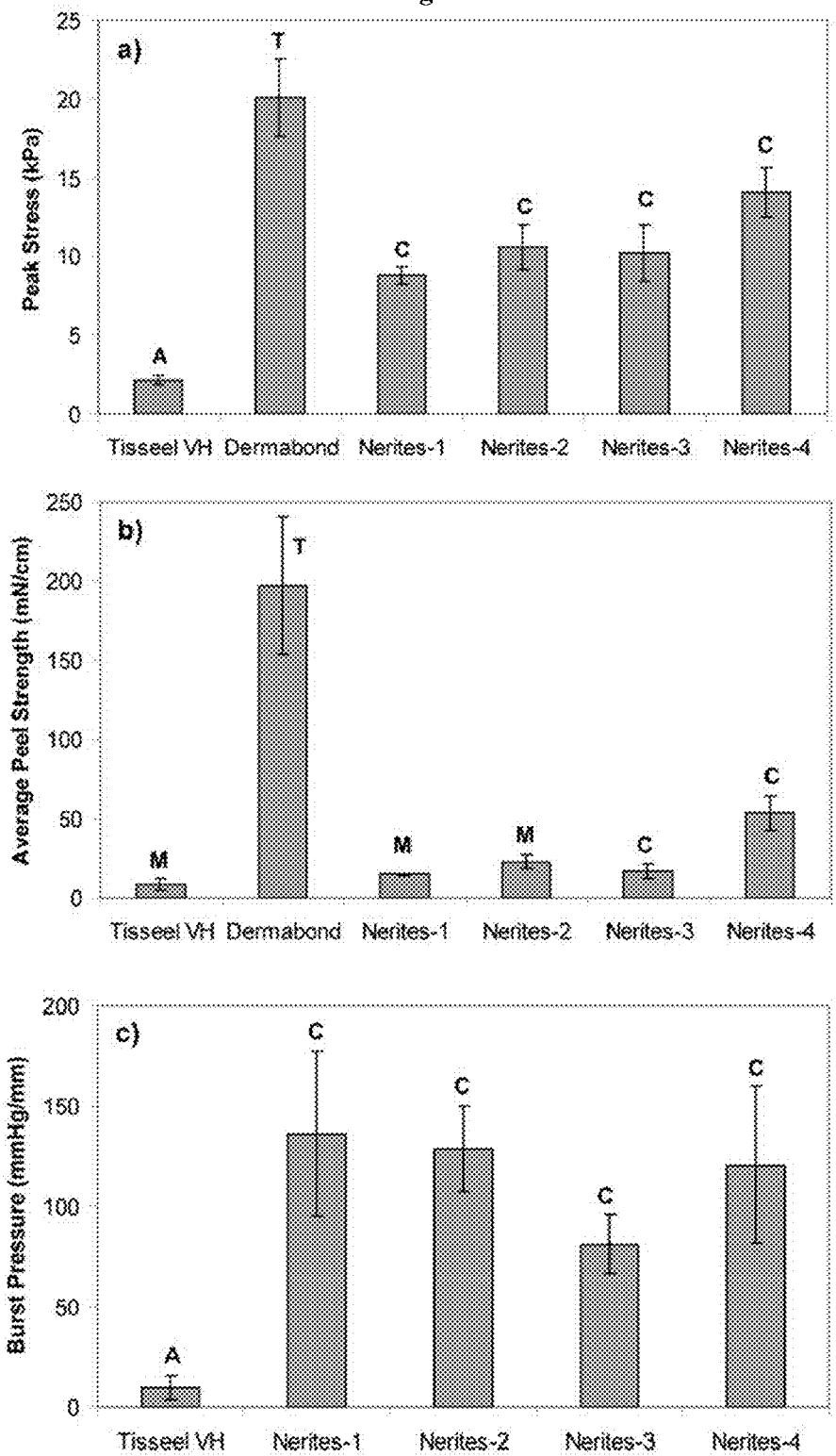
FIG. 11, provides adhesion test results of several bioadhesive constructs of the invention and a commercial product.

As shown in FIG. 11, the adhesives of the invention outperformed Tisseel V H in each of the three adhesion tests. The adhesives of the invention demonstrated more than six times the adhesion strength in lap shear and T-peel tests, while withstanding as much as 16 times the burst pressure per millimeter thickness as Tisseel V H in burst strength testing. Only Dermabond demonstrated stronger adhesive strengths in both lap shear and T-peel adhesion tests as compared to the adhesives of the invention, which resulted in the tearing of collagen substrates. However, cyanoacrylate-based adhesives, like Dermabond, are approved only for topical usage due to cytotoxicity issues and poor mechanical compatibility with soft tissues.[42] The present adhesives generally exhibited cohesive failure, indicating these adhesive formulations form relatively strong interfacial bonds with wetted collagen substrates. The relatively weak mechanical properties of these hydrogel-based adhesives are likely to contribute to the observed cohesive failure. In both the lap shear and T-peel tests, Nerites-4 demonstrated the highest adhesion strength among the adhesives, which may be attributed to the presence of hydrophobic PPG. PPG blocks likely formed physical cross-links that improved the cohesive properties of these hydrogels. Further engineering may be needed to increase the mechanical properties of these adhesives so they not only form strong interfacial bonds with the surface, but also have sufficient cohesive strength.

TABLE 2

Composition of adhesive polymers

| Adhesive Polymer | PEG Content (wt %)[a] | PPG/PCL Content (wt %)[a] | Dopamine Content (wt %)[b] | Molecular Weight (Mw)[c] | Poly-dispersity[c] | Comments |
|---|---|---|---|---|---|---|
| Nerites-4 | 43 | 43 wt % PPG | 4.8 | 58,000 | 1.2 | — |
| Nerites-5 | 62 | 25 wt % PCL | 8.0 | 17,000 | 1.1 | — |
| Nerites-6[d] | 60 | 18 wt % PCL | 12 | 11,000 | 6.6 | Lysyl free —$NH_2$ |
| Nerites-7 | 70 | — | 16 | 13,000 | 1.8 | — |
| Nerites-8 | 62 | — | 12 | TBD | TBD | Lysyl free —$NH_2$ |

[a]Determined from $^1$H NMR
[b]Determined from UV-vis [55]
[c]Determined from gel permeation chromatography in concert with laser light scattering (GPC-LS)
[d]May require further purification Proposed Adhesive Polymers to be Tested The adhesive polymers described above were designed to function as in situ curable tissue adhesives or sealants. Apart from being able to form strong adhesive bonds to wetted, biological tissues, these adhesives were screened for easy preparation (i.e., fast solublization) and rapid curing under biological conditions (i.e., humid environment, body temperature, etc.). However, these hydrogel-based adhesives have relatively weak mechanical strength, which contributed to the observed cohesive failure in the three adhesion tests. Therefore, it is important to combine the adhesive properties of DOPA-derivatives with a supporting substrate that has stronger mechanical properties for use in tendon and ligament augmentation, as these repaired tissues must be able to withstand the stresses associated with normal function and movement.

FIG. 12 and Table 2 show the chemical structure and composition of the adhesive polymers, respectively, to be used in conjunction with collagen membranes in the proposed research. Nerites-4 through Nerites-6 were constructed with a polymeric backbone consisting of amphiphilic multiblock copolymers of PEG and either PPG (Nerites-4) or polycaprolactone (PCL; Nerites-5 and Nerites-6). The presence of PEG allows the subsequent adhesive film to remain relatively hydrophilic to achieve good "wetting" or adhesive contact with the soft tissue substrate. The aggregation of the hydrophobic segments increases cohesive strength while preventing rapid dissolution of the film in the presence of water. Although Nerites-4 contains hydrolysable urethane linkages throughout its polymer backbone, the chemically cross-linked hydrogels of Nerites-4 exhibited no signs of degradation over three months (pH 7.4, 37° C.). Both Nerites-5 and Nerites-6 contain polyester linkages, which should increase the rate at which these polymers degrade into biocompatible degradation products (PEG, 6-hydroxyhexanoic acid, lysine, and cross-linked dopamine). Biodegradation of both the adhesive and the collagen backing is important to prevent the formation of poorly organized scar-tissue that does not contribute to load bearing. Nerites-7 and Nerites-8 were designed to contain an elevated level of the adhesive moiety, dopamine, and could be used as an additive to further increase the interfacial binding ability of the adhesive film. Additionally, both Nerites-6 and Nerites-8 were prepared with a free lysyl amine group adjacent to dopamine. Lysine residues can potentially participate in intermolecular cross-linking with dopamine as well as promote interfacial binding of the adhesive film. Additionally, the presence of the lysyl —$NH_2$ group renders the dihydroxyphenyl ring more hydrophilic, thus making it more accessible for adhesive contact.

Research Design and Methods

Project Design

Development and evaluation of novel water-resistant bioadhesive collagen tape for soft tissue repair will be undertaken. The adhesive coating will be characterized by determining the extent of swelling, hydrophilicity, and in vitro degradability. Adhesion and mechanical tests will be performed on the bioadhesive collagen tape to determine its ability to function as an augmentation device for tendon repair. These experiments were designed to accomplish the following specific aims:

Specific Aim 1: To develop bioadhesive collagen tapes by coating collagen membranes with water-resistant bioadhesives Experiment 1: Coat a thin layer of adhesive on collagen membrane Specific Aim 2: To determine the feasibility of using bioadhesive collagen tape as an augmentation device for tendon and ligament repair Experiment 2: Characterize polymeric adhesive film Experiment 3: Perform adhesion tests of bioadhesive collagen tape Experiment 4: Assess tensile loading of suture-fixed tendon wrapped with bioadhesive collagen tape Experiment 1: Coat a thin layer of adhesive on collagen membrane Rationale In the first experiment, a method will be developed to spread a thin and even adhesive film on the backing material. These adhesive coatings will consist of several formulations combined from polymers shown in FIG. 12 and Table 2 to obtain films with the desired adhesive and mechanical properties. Nerites-4, Nerites-5, and Nerites-6 will be used as the main components in the adhesive coating. These polymers are comprised of amphiphilic multiblock copolymers of PEG and PPG or PCL, which prevent the film from quickly dissolving in aqueous media, and the hydrophobic segments can form physical cross-links. Nerites-7 or Nerites-8 can be added to increase the dopamine content or to introduce lysyl —$NH_2$ groups to the film. Additionally, the thickness of the coating will be optimized, as the overall thickness of the adhesive coating may significantly affect the cohesive properties of the film.[80] Typically, commercially available medical adhesive tapes are coated with 25-70 g/m$^2$ of adhesive depending on the targeted application,[81-85] which translates to approximately 25-70 μm of dry film thickness, assuming a polymer density of 1 g/cm$^3$. We will use this thickness range as a guide in optimizing the thickness of the adhesive film.

Both collagen membranes and glass slides will be used as the backing materials for these adhesive films. Although collagen membrane will be used for the construction of the bioadhesive collagen tape, it swells in the presence of water and can complicate the characterization of the adhesive film in Experiment 2. Thus, glass slides will be used as backing for this experiment. Small intestinal submucosa (SIS) is one of the most studied collagenous matrixes used for soft tissue repair,[32] and commercially available SIS such as CuffPatch (Arthrotek, Warsaw, Ind.) and Restore (DePuy Orthopaedics, Warsaw, Ind.) will be used as the collagen backing.

Protocol

The adhesive films will be applied using a solvent casting method, where the polymer is first dissolved in a relatively volatile solvent (such as methanol or chloroform) to form a viscous solution that can be coated onto either collagen membranes or glass slides. After the solvent evaporates, a dry adhesive film will remain on the backing material. Procedures from ASTM standard D823[86] will be used for this coating process. An automated, motor-driven blade film applicator will be used to ensure an even thickness of the polymer film. Dry film thickness charts will be used as a guideline to determine how much material to use in order to obtain the desired dry film thickness.[87] For example, if a dry film with a thickness of 2.5 mils (63.5 µm) and we have a 55 wt % polymeric solution is desired, according to this chart one would need to apply the coating at 353 square feet per gallon (87 $cm^2$/mL) to form a wet film thickness of 4.5 mils (114 µm). After the adhesive films have dried, ASTM standard D1005[88] will be employed using a micrometer to measure the thickness of the film coated onto the backing. ASTM standard F2217[89] will be used to determine the mass of adhesive polymer that was deposited onto the backing in g/$m^2$, which is the prevalent reporting unit for the amount of adhesive coated on commercially available medical tapes.

Anticipated Results/Alternative Approaches

It is anticipated that dry films of the desired thickness can be evenly coated onto both collagen and glass slide backings using ASTM procedures. Use of a blade applicator was chosen over other methods described in ASTM D823 because this approach uses less material. If an even coating cannot be achieved using the blade applicator, the spray or the dip coating methods as described in ASTM standard D823[86] will be used. Commercially available collagen membranes will be used as the backing materials for the bioadhesive tape. However, since it is sometimes difficult to procure medical products from a potential competitor, multi-layered laminates of collagen sheets will be constructed using published methods for use as the backing material.[38-40] A single layer of collagen sheet has insufficient mechanical properties for most load-bearing applications and many commercially available products consist of laminates of multi-layered collagen sheets. Mechanical properties of these collagen laminates will be characterized and compared to published results.[40]

Experiment 2

Characterization of Polymeric Adhesive Film

Rationale

In this experiment, the adhesive films will be characterized by determining the extent to which they swell in an aqueous buffer, their in vitro rate of degradation, and their hydrophilicity through contact angle measurements. All three properties are interrelated and will affect the overall performance of the adhesive film. For example, the more hydrophilic the film is, the more water it can take up, causing it to swell more. This in turn increases the rate of degradation through hydrolysis. Large amounts of swelling are less desirable if the goal is to make a more cohesive film. However, the surface of the adhesive film needs to maintain a certain degree of hydrophilicity for the formation of good interfacial binding with wetted tissue surface. In addition to controlling the hydrophilicity of the film, chemical cross-links will be introduced through addition of an oxidizing reagent, which will be applied before each test. Upon oxidation, catechol is transformed into highly reactive quinone, which can react with neighboring catechols to form dimers and eventually oligomers of up to six catechols. [62] Chemical cross-linking can be used to solidify the adhesive film, which can affect the extent of swelling and ultimately the mechanical properties of the film. Furthermore, a chemically cross-linked film is less likely to dissociate through dissolution of the polymer into the surrounding aqueous media. Although these oxidants are potential irritants, they are likely reduced into benign forms after undergoing a red-ox reaction with the dihydroxyphenyl ring.[67]

Protocol

Three different tests will be performed to characterize the adhesive film coated onto a glass slide. Swelling experiments will be performed using published procedures with some modifications.[90, 91] Glass slides coated with the dry film will be submerged in phosphate buffered saline (PBS, pH 7.4) at 37° C. and their mass will be recorded at a predetermined time point. The extent of swelling is determined by the mass of the swollen film divided by the mass of dry film. Swelling of the film may take from a few hours to a day to reach equilibrium; the equilibrium will be measured to determine the extent of swelling. In vitro degradation of the adhesive film will be followed using published procedures.[91] The adhesive-coated slides will be submerged in PBS at 37° C. At predetermined time points, we will remove one of the coated slides, dry it, and weigh it. The mass loss of the dry film will be monitored until the film has completely dissolved (degraded). Contact angle measurements will be used to determine the hydrophilicity of the coated film. The advancing contact angle of a drop of water on the film will be measured using a goniometer. The effect of oxidative cross-linking on the film will also be determined by spraying a dilute solution of oxidizing reagent (e.g., sodium periodate, hydrogen periodate, or sodium hydroxide) on the surface before each test. The effect of the type and the concentration of oxidizing reagent utilized on swelling and the degradation profile will be determined.

Anticipated Results/Alternative Approaches

It is anticipated that the extent of swelling and the rate of degradation will be significantly affected by the hydrophilicity of the polymer used to make the film. The hydrophilicity of the coating can be increased by increasing the PEG content or by introducing lysyl amine groups, while elevated dopamine content will decrease hydrophilicity due to the hydrophobic nature of the dihydroxyphenyl ring. Adhesive films constructed from Nerites-4 are likely to degrade much more slowly than those of Nerites-5 and Nerites-6, as these two polymers contain ester linkages that hydrolyze at a faster rate than the urethane linkages in Nerites-4. Furthermore, Nerites-4 has much lower PEG content than its counterparts.

Introduction of chemical cross-linking will likely minimize the extent of swelling. Additionally, a chemically cross-linked film will be less likely to dissociate through dissolution, which allows for a more accurate measurement of the rate of degradation.

Although only a thin film will be coated, it is anticipated that the mass of the film can be measured accurately. For example, if two-thirds of the surface area of a standard glass slide (2.5 cm×7.5 cm) are coated with 25-70 g/m² of adhesive polymer, the mass of the dry film will be 33-88 mg, well above the sensitivity limit of our balance. One concern is that as the degradation of the film proceeds, it will be increasingly difficult to accurately measure the mass of the dry film. Either a larger glass slide will be used or degradation only of thicker films will be followed. Even if the mass of the degraded film cannot be accurately measured, it is anticipated that it can be determinde when the film has completely degraded through visual inspection. The film will likely have a reddish or brownish color due to the presence of oxidized dopamine, which can be readily distinguished from colorless glass slides.

Experiment 3

Adhesion Test of the Bioadhesive Collagen Tape

Rationale

As the tendon is pulled along its axis, the adhesive film will experience shear forces. Therefore, the lap shear adhesion test will be peformed to determine the adhesive properties of the collagen membrane coated with adhesives. A second sheet of collagen membrane will be used as the substrate to simulate attachment to a tendon or ligament, since collagen makes up as much as 70% dry weight of these connective tissues.[27] Bone will also be tested as a substrate as well because the tendon-bone joint is typically the weak link in rotator cuff surgery.[12, 13, 20] Before forming the adhesive joint, an oxidizing reagent will be applied to the film. Oxidized catechol can form irreversible covalent bonds with various functional groups such as —$NH_2$ (lysine) and SH (cysteine) likely to be present on biological substrates. [92] The effectiveness of forming these interfacial chemical bonds will likely affect the adhesive properties of the bioadhesive collagen tape. The effect of oxidizing reagent type and concentration on the adhesive strength of the bioadhesive collagen tape will be determined.

Protocol

Lap shear adhesion testing will be performed using ASTM standard F2255.[77] Both the bioadhesive collagen tape and the collagen substrate will be rehydrated before testing. Oxidizing reagent will be sprayed onto the adhesive film just before joining the two collagen membranes together. The adhesive joint will be pulled apart at different time points, ranging from hours to a day, to determine the rate of interfacial bond formation. The detached adhesive joint will be visually inspected to see if the mode of failure was adhesive or cohesive.

Anticipated Results/Alternative Approaches

It is anticipated that the adhesive strength of these bioadhesive collagen tapes will be significantly greater than that of the hydrogel-based adhesives (see Preliminary Studies). Over 85 wt % of these hydrogel-based adhesives is water. Low polymeric content is one reason why hydrogels generally have weak cohesive strength. Similar PEG-based hydrogels have a modulus of $10^4$ Pa,[55, 62] whereas swollen polymeric films based on PEG and PCL have demonstrated moduli that are three orders of magnitude higher.[93] Thus, if the catechols are properly oriented for interfacial binding, film-based adhesives will demonstrate considerably stronger adhesive strength than hydrogel-based adhesives. Multilayer lamination of SIS significantly increases the tensile properties of these collagen membranes.[28, 39] However, in the event that the adhesive joints fail due to tearing of the membrane, other modes of adhesion testing will be used. The 180° peel test (ASTM D3330)[94] will likely be used as the alternative testing method, as it measures a combination of tensile and shear forces.

Experiment 4

Tensile Loading of Suture-Fixed Tendon Wrapped with Bioadhesive Collagen Tape

Rationale

In this experiment, a bovine Achilles tendon model will be used to determine the effectiveness of using the proposed bioadhesive collagen tape as an augmentation device in tendon repair. The tensile strength needed to pull apart transected tendons which have been repaired using several different methods, as shown in FIG. 9, will be determined. Bovine Achilles tendon was chosen due to its size for easy handling and its ready availability. For controls, an intact tendon and a tendon repaired with sutures alone (FIG. 1-D) will be used. The test models will be:

sutured tendon augmented with nonadhesive collagen membrane sutured over the repair (FIG. 1-E), sutured tendon augmented with bioadhesive collagen tape (FIG. 1-F), and sutured tendon augmented with bioadhesive collagen tape sutured over the repair (FIG. 1-G).

The tensile strength of the bioadhesive collagen tape glued with and without sutures will be tested to an unfixed repair to simulate those injuries that cannot be fixed with sutures (e.g., neglected Achilles tendon ruptures and massive rotator cuff tears).

Protocol

Tendons will be cleanly severed and then repaired with a modified Kessler suture pattern, the standard in clinical practice for tendon repair.[95] The collagen patches will be wrapped around the severed tendon with or without further suturing. Tensile tests will be performed on a Universal Materials Testing Machine (Admet). Each end of the tendon will be clamped to the load cell. The tendons will then be stretched at a rate of 0.033 cm/sec (20 mm/min) until the repair fails,[95] and the force at failure and the mode and location of failure will be recorded.

Anticipated Results/Alternative Approaches

Results of the tensile testing for various configurations will be compared to the tensile strength of the intact Achilles tendon and the suture-only repaired Achilles tendon to determine which method produces the strongest repaired Achilles tendon. The rate at which the tendon is stretched can be either increased or decreased if need be. Within the literature, stretching rates varied anywhere from 0.01 cm/sec to 1.67 cm/sec[31, 95-99] for mechanical testing on tendons and ligaments. Because no standardized testing parameters for tensile testing of tendons or ligaments were found, a stretching rate based on studies utilizing similar clamping techniques was selected. In the event the tendons repeatedly fail at the clamp, (i.e., pressure exerted on the tissue by the clamping device damages the tissue) a procedure modified from a published method,[96] may be used in which the ends of the tendon are placed between two sheets of blotting paper, which are then folded twice and clamped into the clamping device. Another alternative could be to investigate using sinusoidal clamps (either purchased or constructed in-house) to help distribute the force placed on the tendon at the clamping site, as was done in another study.[98] The bioadhesive collagen tape can be wrapped around the tendon multiple times as well to determine its impact on repair strength.

BIBLIOGRAPHY

1. Williams, G. R. J., et al, *Rotator Cuff Tears: Why do we repair them?* The Journal of Bone and Joint Surgery, 2004. 86-A(12): p. 2764-2776.
2. Leppilahti, J., Orava, S., *Total Achilles Tendon Rupture: A Review*. Sports Med., 1998. 25(2): p. 79-100.
3. Tozer, S., Duprez, D., *Tendon and Ligament: Development, Repair and Disease*. Birth Defects Research (Part C), 2005. 75: p. 226-236.
4. Maffulli, N., *Rupture of the Achilles Tendon*. The Journal of Bone and Joint Surgery, 1999. 81-A(7): p. 1019-1036.
5. Jozsa, L., Kvist, M., Balint, B. J., et al, *The role of recreational sport activity in Achilles tendon rupture: A clinical, pathoanatomical, and sociological study of 292 cases*. The American Journal of Sports Medicine, 1989. 17: p. 338-343.
6. Strauss, E. J., Ishak, C., Jazrawi, L., Sherman, O., Rosen, J., *Operative Treatment of acute Achilles tendon ruptures: An institutional review of clinical outcomes*. Injury, International Journal of the care of the Injured, 2007. 38: p. 832-838.
7. Pajala, A., Kangas, J., Ohtonen, P., Leppilahti, J., *Rerupture and Deep Infection Following Treatment of Total Achilles Tendon Rupture*. The Journal of Bone and Joint Surgery, 2002. 84-A(11): p. 2016-2021.
8. Brown, C. H., Carson, E. W, *Revision Anterior Cruciate Ligament Surgery*. Clin Sports Med, 1999. 18: p. 109-171.
9. *ACL Injury: Does it Require Surgery?* 2007 [cited; Available from: http://orthoinfo.aaos.org/topic.cfm?topic=A00297.
10. Frank, C. B., Jackson, D. W., *Current Concepts Review—The Science of Reconstruction of the Anterior Cruciate Ligament*. The Journal of Bone and Joint Surgery, 1997. 79-A(10): p. 1556-1576.
11. Ireland, M. L., *Anterior Cruciate Ligament Injury in Female Athletes: Epidemiology*. Journal of Athletic Training, 1999. 34(2): p. 150-154.
12. Nicholson, G. P., et al., *Evaluation of a cross-linked acellular porcine dermal patch for rotator cuff repair augmentation in an ovine model*. J. Shoulder Elbow Surg., 2007. 16(5S): p. 184S-190S.
13. France, P. E., Paulos, L. E., Harner, C. D., Straight, C. B., *Biomechanical evaluation of rotator cuff fixation methods*. The American Journal of Sports Medicine, 1989. 17(2): p. 176-181.
14. Garabito, A., Martinez-Miranda, J., Sanchez-Sotelo, J., *Augmented Repair of Acute Achilles Tendon Ruptures Using Gastrocnemius-soleus Fascia*. International Orthopaedics, 2005. 29: p. 42-46.
15. Winter, E., Weise, K., Weller, S., Ambacher, T., *Surgical Repair of Achilles Tendon Rupture: Comparison of Surgical with Conservative Treatment*. Arch. Orthop. Trauma Surg., 1998. 117: p. 364-367.
16. Nistor, L., *Surgical and Non-surgical Treatment of Achilles Tendon Rupture*. The Journal of Bone and Joint Surgery, 1981. 63-A(3): p. 394-399.
17. Johnson, R. J., Beynnon, Bruce D., Nichols, Claude E., Renstrom, A. F. H., *The Treatment of Injuries of the Anterior Cruciate Ligament*. The Journal of Bone and Joint Surgery, 1992. 74-A(1): p. 140-151.
18. Djurasovic, M., Marra, G., Arroyo, J. S., et al, *Revision Rotator Cuff Repair: Factors Influencing Results*. The Journal of Bone and Joint Surgery, 2001. 83-A(12): p. 1849-1855.
19. Kummer, F. J., Iesaka, K., *The Role of Graft Materials in Suture Augmentation for Tendon Repairs and Reattachment*. J. Biomed. Mater. Res. Part B: Appl. Biomater, 2005. 74B: p. 789-791.
20. Tingart, M. J., et al, *Pullout strength of suture anchors used in rotator cuff repair*. The Journal of Bone and Joint Surgery, 2003. 85-A(11): p. 2190-2198.
21. Lynn, T., *Repair of the Torn Achilles Tendon, Using the Plantaris Tendon as a Reinforcing Membrane*. The Journal of Bone and Joint Surgery, 1964. 48-A(2): p. 268-272.
22. *Zimmer Collagen Repair Patch*. Tissue Science Laboratories, 2005.
23. *Restore Orthobiologic Implants for Use in Rotator Cuff Shoulder Surgery*. Mercer-Buck Orthopaedics, 2005.
24. Hirooka, A., et al, *Augmentation with a Gore-Tex patch for repair of large rotator cuff tears that cannot be sutured*. J Orthopaedic Science, 2002. 7: p. 451-456.
25. Mandelbaum, B. R., Myerson, M. S., Forster, R., *Achilles tendon ruptures: a new method of repair, early range of motion, and functional rehabilitation*. The American Journal of Sports Medicine, 1995. 23(4): p. 392-395.
26. Speck, M., Klaue, K., *Early Full Weightbearing and Functional Treatment after Surgical Repair of Acute Achilles Tendon Rupture*. The American Journal of Sports Medicine, 1998. 26(6): p. 789-793.
27. Harkness, R. D., *Biological functions of collagen*. Biol. Rev. Camb. Philos. Soc., 1961. 36: p. 399-463.
28. Abraham, G. A., Murray, J., Billiar, K., Sullivan, S. J., *Evaluation of the porcine intestinal collagen layer as a biomaterial*. J. Biomed. Mater. Res., 2000. 51: p. 442-452.
29. Metcalf, M. H., F. H. S. III, and B. Kellum, *Surgical technique for xenograft (SIS) augmentation of rotator-cuff repairs*. 2002. 12(3): p. 204-208.
30. Gilbert, T. W., et al., *Degradation and Remodeling of Small Intestinal Submucosa in Canine Achilles Tendon Repair*. The Journal of Bone and Joint Surgery (American), 2007. 89: p. 621-630.
31. Badylak, S. F., et al, *The Use of Xenogeneic small intestinal submucosa as a biomaterial for Achilles tendon repair in a dog model*. Journal of Biomedical Materials Research, 1995. 29: p. 977-985.
32. Badylak, S. F., *The extracellular matrix as a biologic scaffold material*. Biomaterials, 2007. 28: p. 3587-3593.
33. Ansaloni, L., et al., *Immune response to small intestinal submucosa (surgisis) implant in humans: preliminary observations*. J. Invest. Surg., 2007. 20(4): p. 237-41.
34. Musahl, V., et al., *The use of porcine small intestinal submucosa to enhance the healing of the medial collateral ligament—a functional tissue engineering study in rabbits*. J. Orthop. Res., 2004 22(1): p. 214-20.
35. Badylak, S., et al., *Resorbable bioscaffold for esophageal repair in a dog model*. J. Pediatr. Surg., 2000 35(7): p. 1097-103.
36. Ledet, E. H., et al., *A pilot study to evaluate the effectiveness of small intestinal submucosa used to repair spinal ligaments in the goat*. Spine J., 2002 2(3): p. 188-96.
37. Valentin, J. E., et al., *Extracellular Matrix Bioscaffolds for Orthopaedic Applications. A Comparative Histologic Study*. J. Bone Joint Surg. Am., 2006. 88: p. 2673-2686.
38. Khor, E., *Methods for the treatment of collagenous tissues for bioprostheses*. Biomaterials, 1997 18(2): p. 95-105.

39. Gloeckner, D. C., Sacks, M. S., Billiar, K. L., Bachrach, N., *Mechanical evaluation and design of a multilayered collagenous repair biomaterial.* J. Biomed. Mater. Res., 2000. 52: p. 365-373.
40. Billiar, K., Murray, J., Laude, D., Abraham, G., Bachrach, N., *Effects of carbodiimide crosslinking conditions on the physical properties of laminated intestinal submucosa.* J. Biomed. Mater. Res., 2001. 56: p. 101-108.
41. Gratzer, P. F., Santerre, J. P., Lee, J. M., *The effect of chemical modification of amino acid side-chains on collagen degradation by enzymes.* j. Biomed. Mater. Res. Part B: Appl. Biomater, 2006. 81B: p. 1-111.
42. Refojo, M. F., C. H. Dohlman, and J. Koliopoulos, *Adhesives in opthalmology: a review.* Surv. Ophthamol., 1971. 15(4): p. 217-36.
43. Saltz, R., et al., *Experimental and clinical applications of fibrin glue.* Plast Reconstr Surg, 1991. 88(6): p. 1005-15; discussion 1016-7.
44. Banninger, H., et al., *Fibrin glue in surgery: frequent development of inhibitors of bovine thrombin and human factor V.* British Journal of Haematology, 1993. 85(3): p. 528-32.
45. Ikada, Y., *Tissue adhesives, in Wound Closure Biomaterials and Devices,* C. C. Chu, J. A. von Fraunhofer, and H. P. Greisler, Editors. 1997, CRC Press, Inc.: Boca Raton, Fla. p. 317-346.
46. Waite, J. H., *Nature's underwater adhesive specialist.* Int. J. Adhes. Adhes., 1987. 7(1): p. 9-14.
47. Yamamoto, H., *Marine adhesive proteins and some biotechnological applications.* Biotechnology and Genetic Engineering Reviews, 1996. 13: p. 133-65.
48. Kramer, K. J., et al., *Insect cuticle tanning: Enzymes and cross-link structure,* in *Natural Occurring Pest Bioregulators.* 1991. p. 87-105.
49. Yu, M., J. Hwang, and T. J. Deming, *Role of L-3,4-dihydroxyphenylanine in mussel adhesive proteins.* Journal of American Chemical Society, 1999. 121(24): p. 5825-5826.
50. Deming, T. J., M. Yu, and J. Hwang, *Mechanical studies of adhesion and crosslinkning in marine adhesive protein analogs.* Polymeric Materials: Science and Engineering, 1999. 80: p. 471-472.
51. Waite, J. H., *Mussel beards: A coming of Age.* Chemistry and Industry, 1991. 2 September: p. 607-611.
52. Papov, V. V., et al., *Hydroxyarginine-containing polyphenolic proteins in the adhesive plaques of the marine mussel Mytilus edulis.* Journal of Biological Chemistry, 1995. 270 (34): p. 20183-92.
53. Waite, J. H. and X. Qin, *Polyphosphoprotein from the Adhesive Pads of Mytilus edulis.* Biochemistry, 2001. 40(9): p. 2887-93.
54. Yu, M. and T. J. Deming, *Synthetic polypeptide mimics of marine adhesives.* Macromolecules, 1998. 31(15): p. 4739-45.
55. Lee, B. P., et al., *Rapid Photocurable of Amphiphilic Block Copolymers Hydrogels with High DOPA Contents.* Maclomolecules, 2006. 39: p. 1740-48.
56. Lee, H., N. F. Scherer, and P. B. Messersmith, *Single Molecule Mechanics of Mussel Adhesion.* Proc. Natl. Acad. Sci., 2006. 103: p. 12999-13003.
57. Maugh, K. J., et al., *Recombinant bioadhesive proteins of marine animals and their use in adhesive compositions,* in *Genex Corp.* 1988: USA. p. 124.
58. Strausberg, R. L., et al., *Development of a microbial system for production of mussel adhesive protein,* in *Adhesives from Renewable Resources.* 1989. p. 453-464.
59. Filpula, D. R., et al., *Structural and functional repetition in a marine mussel adhesive protein.* Biotechnol. Prog., 1990. 6(3): p. 171-7.
60. Yamamoto, H., S. Yamauchi, and S. Ohara, *Synthesis and adhesive studies of marine adhesive proteins of the Chilean Mussel Aulacomya ater.* Biomimetics, 1992. 1(3): p. 219-38.
61. Yamamoto, H. and K. Ohkawa, *Synthesis of adhesive protein from the vitellaria of the liver fluke Fasciola hepatica.* Amino Acids, 1993. 5(1): p. 71-5.
62. Lee, B. P., J. L. Dalsin, and P. B. Messersmith, *Synthesis and Gelation of DOPA-Modified Poly(ethylene glycol) Hydrogels.* Biomacromolecules, 2002. 3(5): p. 1038-47.
63. Huang, K., et al., *Synthesis and Characterization of Self-Assembling Block Copolymers Containing Bioadhesive End Groups.* Biomacromolecules, 2002. 3(2): p. 397-406.
64. Lee, B. P., et al., *Synthesis of 3,4-Dihydroxyphenylalanine (DOPA) Containing Monomers and Their Copolymerization with PEG-Diacrylate to from Hydrogels.* Journal of Biomaterials Science, Polymer Edition, 2004. 15: p. 449-464.
65. Guvendiren, M., et al. *Adhesion in Self-Assembled Hydrogels with High DOPA Content.* in *30th Annual Meeting of the Adhesion Society.* 2007. Tampa, Fla.
66. Lee, H., B. P. Lee, and P. B. Messersmith, *A Reversible Wet/Dry Adhesive Inspired by Mussels and Geckos.* Nature, 2007. 448(19 July): p. 338-341.
67. Burke, S. A., et al., *Thermal gelation and tissue adhesion of biomimetic hydrogels.* Biomed. Mater., 2007. 2: p. 203-210.
68. Oiwa, H., et al., *Experimental study of small arterial anastomosis with gelatin-resorcin-formaldehyde glue and collagen sheet.* Artif Organs, 2001 25(4): p. 281-91.
69. Gunawan, R., et al., *Surface Presentation of Bioactive Ligands in a Non-Adhesive Background using DOPA-Tethered Biotinylated Poly(Ethylene Glycol).* Langmuir, 2007. 23(21): p. 10635-10643.
70. Nunalee, F. N., et al., *QCM Studies of Polymer Gels and Solutions in Liquid Environment.* Analytical Chemistry, 2006. 78: p. 1158-1166.
71. Dalsin, J. L., et al., *Mussel Adhesive Protein Mimetic Polymers for the Preparation of Nonfouling Surfaces.* Journal of American Chemical Society, 2003. 125: p. 4253-4258.
72. Lee, B. P., J. L. Dalsin, and P. B. Messersmith, *Synthetic Polymer Mimics Of Mussel Adhesive Proteins for Medical Applications,* in *Biological Adheisves,* A. M. Smith and J. A. Callow, Editors. 2006, Springer-Verlag. p. 257-278.
73. Messersmith, P. B., et al., *Biomimetic adhesive compositions containing 3,4-Dihydroxyphenyl-L-alanine and useful for bonding substrates under water.* 2003: WO 2003008376.
74. Messersmith, P. B., et al., *Adhesive polymeric compositions for use in substantially aqueous environment.* 2005: WO 2005118831.
75. Messersmith, P. B., et al., *Polymeric adhesive compositions containing dihydroxyphenyl moieties and their uses in prevention of protein or cellular adhesion and biofouling.* 2005: US 2005288398.
76. Shull, K. R., et al., *Modified acrylic block copolymers for hydrogels and pressure sensitive wet adhesives.* 2007: US 2007208141.
77. ASTM-F2255, *Standard Test Method for Strength Properties of Tissue Adhesives in Lap-Shear by Tension Loading.* 2003.
78. ASTM-F2256, *Standard Test Methods for Strength Properties of Tissue Adhesives in T-Peel Tension Loading.* 2005.

79. ASTM-F2392, *Standard Test Method for Burst Strength of Surgical Sealants* 2004.
80. Minghetti, P., F. Cilurzo, and A. Casiraghi, *Measuring adhesive performance in transdermal delivery systems*. American Journal of Drug Delivery, 2004. 2(3): p. 193-206.
81. *MED 5030 Product Information Bulletin*. Avery-Dennison.
82. Nho, K., et al., *PEG-modified hemoglobin as an oxygen carrier*, in *Poly(ethylene glycol) chemistry: biotechnical and biomedical applicationss*, J. M. Harris, Editor. 1992, Plenum Press: New York. p. 171-182.
83. *ARcare® 90446 Product Data Sheet*. Adhesive Research Inc., 2004.
84. *ARcare® 90339 Product Data Sheet*. Adhesive Research Inc., 2004.
85. Jaschke, A., *Oligonucleotide-poly(ethylene glycol) conjugates: synthesis, properties, and applications*, in *Poly(ethylene glycol): chemistry and biological applications*, J. M. Harris and S. Zalipsky, Editors. 1997, American Chemical Society: Washington, D. C. p. 265-283.
86. ASTM-D823, *Standard Practicese for Producing Films of Uniform Thickness of Paint, Varnish, and Related Products on Test Panels*. 2001.
87. Schacht, E. H. and K. Hoste, *Poly(ethylene glycol)-grafted polymers as drug carriers*, in *Poly(ethylene glycol): chemistry and biological applications*, J. M. Harris and S. Zalipsky, Editors. 1997, American Chemical Society: Washington, D. C. p. 297-315.
88. ASTM-D 1005, *Standard Test Method for Measurement of Dry-Film Thickness of Organic Coatings Using Micrometers*. 2001.
89. ASTM-F2217, *Standard Practice for Coating/Adhesive Weight Determination*. 2007.
90. Cohn, D., et al., *Biodegradable poly(ethylene oxide)/poly (e-caprolactone) multiblock copolymers*. Journal of Biomedical Materials Research, 2002. 59(2): p. 273-281.
91. Nagata, M. and I. Kitazima, *Photocurable biodegradable poly(epsilon-caprolactone)/poly(ethylene glycol) multiblock copolymers showing shape-memory properties* Colloid & Polymer Science, 2006. 284: p. 380-386.
92. Sagert, J., C. Sun, and J. H. Waite, *Chemical Subtleties of Mussel and Polychaete Holdfasts*, in *Biological Adheisves*, A. M. Smith and J. A. Callow, Editors. 2006, Springer-Verlag. p. 125-143.
93. Bae, Y. H., et al., *Biodegradable amphiphilic multiblock copolymers and their implications for biomedical applications*. Journal of Controlled Release, 2000. 64(1-3): p. 3-13.
94. ASTM-D3330, *Standard Test Method for Peel Adhesion of Pressure-Sensitive Tape*. 2004.
95. Shaieb, M. D., Singer, D. I., *Tensile Strengths of various suture techniques*. The Journal of Hand Surgery (British and European Volume), 1997. 22B(6): p. 764-767.
96. Probst, A., et al, *A New Clamping Technique for Biomechanical Testing of Tendons in Small Animals*. Journal of Investigative Surgery, 2000. 13: p. 313-318.
97. Garrett, W. E., Safran, M. R., Seaber, A. V., Glisson, R. R., Ribbeck, B. M., *Biomechanical comparison of stimulated and nonstimulated skeletal muscle pulled to failure*. The American Journal of Sports Medicine, 1987. 15(5): p. 448-454.
98. Kurtz, C. A., et al, *Insulin-Like Growth Factor I Accelerates Functional Recovery from Achilles Tendon Injury in a Rat Model*. The American Journal of Sports Medicine, 1999. 27(3): p. 363-369.
99. Forslund, C., Rueger, D., Aspenberg, P., *A Comparative Dose-Response Study of Cartilage-Derived Morphogenetic Protein (CDMP)*-1, -2 *and*-3 *for Tendon Healing in Rats*. Journal of Orthopaedic Research, 2003. 21: p. 617-621.

Bioadhesives

Suitable materials that can serve as bioadhesives useful to prepare the constructs of the invention include those described in 60/910,683 filed on Apr. 9, 2007, entitled "DOPA-Functionalized, Branched, Poly(ethylene-Glycol) Adhesives", by Sean A. Burke, Jeffrey L. Dalsin, Bruce P. Lee and Phillip B. Messersmith, U.S. Ser. No. 12/099,254, filed Apr. 8, 2008, entitled "DOPA-Functionalized, Branched, Poly(ethylene-Glycol) Adhesives", by Sean A. Burke, Jeffrey L. Dalsin, Bruce P. Lee and Phillip B. Messersmith, U.S. Ser. No. 11/676,099, filed Feb. 16, 2007, entitled "Modified Acrylic Block Copolymers for Hydrogels and Pressure Sensitive Wet Adhesives", by Kenneth R. Shull, Murat Guvendiren, Phillip B. Messermsith and Bruce P. Lee and U.S. Ser. No. 11/834,651, filed Aug. 6, 2007, entitled "Biomimetic Compounds and Synthetic Methods Therefor", by Bruce P. Lee, the contents of which are incorporated in their entirety herein by reference including any provisional applications referred to therein for a priority date(s) for all purposes.

"Monomer" as the term is used herein to mean non-repeating compound or chemical that is capable of polymerization to form a pB.

"Prepolymer" as the term is used herein to mean an oligomeric compound that is capable of polymerization or polymer chain extension to form a pB. The molecular weight of a prepolymer will be much lower than, on the order of 10% or less of, the molecular weight of the pB.

Monomers and prepolymers can be and often are polymerized together to produce a pB.

"pB" as the term is used herein to mean a polymer backbone comprising a polymer, co-polymer, terpolymer, oligomer or multi-mer resulting from the polymerization of pB monomers, pB prepolymers, or a mixture of pB monomers and/or prepolymers. The polymer backbone is preferably a homopolymer but most preferably a copolymer. The polymer backbone is DHPp excluding DHPD.

pB is preferably polyether, polyester, polyamide, polyurethane, polycarbonate, or polyacrylate among many others and the combination thereof.

pB can be constructed of different linkages, but is preferably comprised of acrylate, carbon-carbon, ether, amide, urea, urethane, ester, or carbonate linkages or a combination thereof to achieve the desired rate of degradation or chemical stability.

pB of desired physical properties can be selected from prefabricated functionalized polymers or FP, a pB that contain functional groups (i.e. amine, hydroxyl, thiol, carboxyl, vinyl group, etc.) that can be modified with DHPD to from DHPp.

The actual method of linking the monomer or prepolymer to form a pB will result in the formation of amide, ester, urethane, urea, carbonate, or carbon-carbon linkages or the combination of these linkages, and the stability of the pB is dependent on the stability of these linkages.

"FP" as the term is used herein to mean a polymer backbone functionalized with amine, thiol, carboxy, hydroxyl, or vinyl groups, which can be used to react with DHPD to form DHPp, for example.

"DHPD weight percent" as the term is used herein to mean the percentage by weight in DHPp that is DHPD.

"DHPp molecular weight" as the term is used herein to mean the sum of the molecular weights of the polymer backbone and the DHPD attached to said polymer backbone.

In one aspect, the polymer comprises the formula

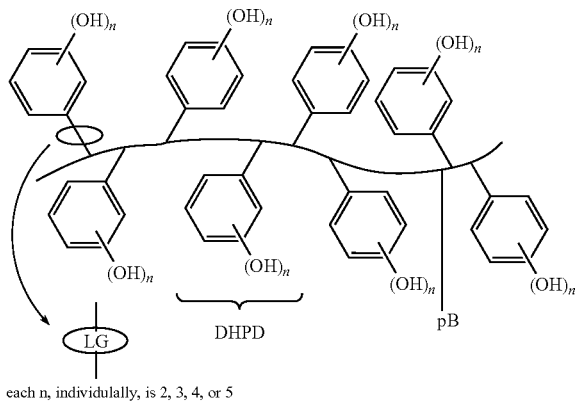

each n, individulally, is 2, 3, 4, or 5 wherein LG is an optional linking group or linker, DHPD is a multihydroxyphenyl group, each n, individually, is 2, 3, 4 or 5, and pB is a polymeric backbone.

In another aspect, the polymer comprises the formula:

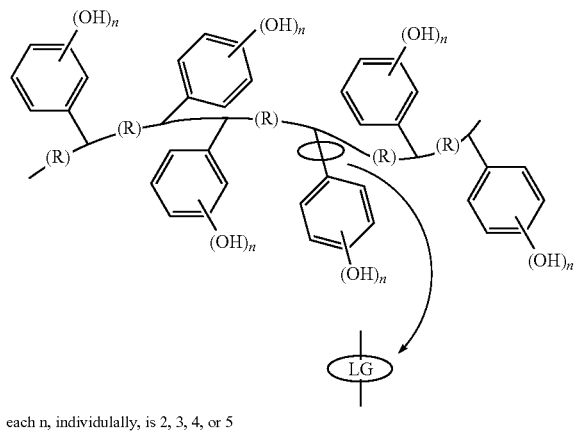

each n, individulally, is 2, 3, 4 or 5 wherein R is a monomer or prepolymer linked or polymerized to form pB, pB is a polymeric backbone, LG is an optional linking group or linker and each n, individually, is 2, 3, 4 or 5.

In another aspect, the present invention provides a multi-armed, poly (alkylene oxide) polyether, multihydroxy (dihydroxy)phenyl derivative (DHPD) having the general formula:

CA-[Z-PA-(L)$_a$-(DHPD)$_b$-(AA)$_c$-PG]$_n$ wherein
CA is a central atom selected from carbon, oxygen, sulfur, nitrogen, or a secondary amine, most particularly a carbon atom;
each Z, independently, is a C1 to a C6 linear or branched, substituted or unsubstituted alkyl group or a bond;
each PA, independently, is a substantially poly(alkylene oxide) polyether or derivative thereof;
each L, independently, optionally, is a linker or is a linking group selected from amide, ester, urea, carbonate or urethane linking groups;
each DHPD, independently is a multihydroxy phenyl derivative;
each AA, independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker
"b" has a value of one or more;
"c" has a value in the range of from 0 to about 20; and
"n" has a value from 3 to 15. Such materials are useful as adhesives, and more specifically, medical adhesives that can be utilized as sealants.

The identifier "CA" refers to a central atom, a central point from which branching occurs, that can be carbon, oxygen, sulfur, a nitrogen atom or a secondary amine. It should be understood therefore, that when carbon is a central atom, that the central point is quaternary having a four armed branch. However, each of the four arms can be subsequently further branched. For example, the central carbon could be the pivotal point of a moiety such as 2, 2-dimethylpentane, wherein each of the methylenes attached to the quaternary carbon could each form 3 branches for an ultimate total of 12 branches, to which then are attached one or more PA(s) defined herein below. An exemplary CA containing molecule is pentaerythritol, $C(CH_2OH)_4$.

Likewise, oxygen and sulfur can serve as the central atom. Both of these heteroatoms can then further be linked to, for example, a methylene or ethylene that is branched, forming multiple arms therefrom and to which are then attached one or more PA(s).

When the central atom is nitrogen, branching would occur so that at least 3 arms would form from the central nitrogen. However, each arm can be further branched depending on functionality linked to the nitrogen atom. As above, if the moiety is an ethylene, the ethylene group can serve as additional points of attachment (up to 5 points per ethylene) to which are then attached one or more PA(s). Hence, it is possible that a molecule where the central atom is nitrogen, could have up to 15 branches starting therefrom, wherein 3 fully substituted ethylene moieties are attached to the central nitrogen atom.

Where the central atom is a secondary amine,

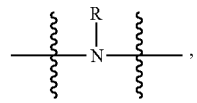

wherein R can be a hydrogen atom or an substituted or unsubstituted, branched or unbranched alkyl group. The remaining sites on the amine then would serve as points of attachment for at least 2 arms. Again, each arm can be further branched depending on functionality linked to the nitrogen atom. As above, if the moiety is an ethylene, the ethylene group can serve as additional points of attachment (up to 5 points per ethylene) to which are then attached one or more PA(s). Hence, it is possible that a molecule where the central atom is a secondary amine, there could be up to 10 branches emanating therefrom, wherein 2 fully substituted ethylene moieties are attached to the central nitrogen atom.

In particular, the central atom is a carbon atom that is attached to four PAs as defined herein.

It should be understood that the central atom (CA) can be part of a PA as further defined herein. In particular, the CA can be either a carbon or an oxygen atom when part of the PA.

The compound can include a spacer group, Z, that joins the central atom (CA) to the PA. Suitable spacer groups include C1 to C6 linear or branched, substituted or unsubstituted alkyl groups. In one embodiment, Z is a methylene (—$CH_2$—, ethylene —$CH_2CH_2$— or propene —$CH_2CH_2CH_2$—). Alternatively, the spacer group can be a bond formed between the central atom and a terminal portion of a PA.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms ($C_1$-$C_6$ alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2R^b$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$—$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O)_2$, —$P(O)(OR^b)(O^-)$, —$P(O)(OR^b)(OR^b)$, —$C(O)R^b$, —$C(S)R^b$, —$C(NR^b)R^b$, —$C(O)OR^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$—$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$—$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and $NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms e.g., N, O, S, P, etc. and of functional groups e.g., —COOH, —$NH_2$, —SH, as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, or of this polymer. It should also be understood that PAs can include terminal end groups such as PA-O—$CH_2$—$CH_2$—$NH_2$, e.g., PEG-O—$CH_2$—$CH_2$—$NH_2$ (as a common form of amine terminated PA). PA-O—$CH_2$—$CH_2$—$CH_2$—$NH_2$, e.g., PEG-O—$CH_2$—$CH_2$—$CH_2$—$NH_2$ is also available as well as PA-O—$(CH_2$—$CH(CH_3)$—$O)_{xx}$—$CH_2$—$CH(CH_3)$—$NH_2$, where xx is 0 to about 3, e.g., PEG-O—$(CH_2$—$CH(CH_3)$—$O)_{xx}$—$CH_2$—$CH(CH_3)$—$NH_2$ and a PA with an acid end-group typically has a structure of PA-O—$CH_2$—COOH, e.g., PEG-O—$CH_2$—COOH. These are all contemplated as being within the scope of the invention and should not be considered limiting.

Generally each PA of the molecule has a molecular weight between about 1,250 and about 12,500 daltons and most particularly between about 2,500 and about 5,000 daltons. Therefore, it should be understood that the desired MW of the whole or combined polymer is between about 5,000 and about 50,000 Da with the most preferred MW of between about 10,000 and about 20,000 Da, where the molecule has four "arms", each arm having a MW of between about 1,250 and about 12,500 daltons with the most preferred MW of 2,500 and about 5,000 Da.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation. In one embodiment, the PA is a polyalkylene glycol polyether or derivative thereof, and most particularly is polyethylene glycol (PEG), the PEG unit having a molecular weight generally in the range of between about 1,250 and about 12,500 daltons, in particular between about 2,500 and about 5,000 daltons.

It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

It should be understood that the PA terminal end groups can be functionalized. Typically the end groups are OH, $NH_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notation of "L" refers to either a linker or a linking group. A "linker" refers to a moiety that has two points of attachment on either end of the moiety. For example, an alkyl dicarboxylic acid HOOC-alkyl-COOH (e.g., succinic acid) would "link" a terminal end group of a PA (such as a hydroxyl or an amine to form an ester or an amide respectively) with a reactive group of the DHPD (such as an $NH_2$, OH, or COOH). Suitable linkers include an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano [2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C3 through C10 dicarbonyl alkylenes such as malonic acid, succinic acid, etc.

A linking group refers to the reaction product of the terminal end moieties of the PA and DHPD (the situation where "a" is 0; no linker present) condense to form an amide, ester, urea, carbonate or urethane linkage depending on the reactive sites on the PA and DHPD. In other words, a direct bond is formed between the PA and DHPD portion of the molecule and no linker is present.

The denotation "DHDP" refers to a multihydroxy phenyl derivative, such as a dihydroxy phenyl derivative, for example, a 3, 4 dihydroxy phenyl moiety. Suitable DHDP derivatives include the formula:

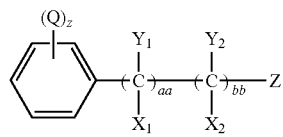

wherein Q is an OH;
"z" is 2 to 5;
each $X_1$, independently, is H, $NH_2$, OH, or COOH;
each $Y_1$, independently, is H, $NH_2$, OH, or COOH;
each $X_2$, independently, is H, $NH_2$, OH, or COOH;
each $Y_2$, independently, is H, $NH_2$, OH, or COOH;
Z is COOH, $NH_2$, OH or SH;
aa is a value of 0 to about 4;
bb is a value of 0 to about 4; and
optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1.

In one aspect, z is 3.

In particular, "z" is 2 and the hydroxyls are located at the 3 and 4 positions of the phenyl ring.

In one embodiment, each $X_1$, $X_2$, $Y_1$ and $Y_2$ are hydrogen atoms, aa is 1, bb is 1 and Z is either COOH or $NH_2$.

In another embodiment, $X_1$ and $Y_1$ are both hydrogen atoms, $X_2$ is a hydrogen atom, aa is 1, bb is 1, $Y_2$ is $NH_2$ and Z is COOH.

In still another embodiment, $X_1$ and $Y_2$ are both hydrogen atoms, aa is 1, bb is 0, and Z is COOH or $NH_2$.

In still another embodiment, aa is 0, bb is 0 and Z is COOH or $NH_2$.

In still yet another embodiment, z is 3, aa is 0, bb is 0 and Z is COOH or $NH_2$.

It should be understood that where aa is 0 or bb is 0, then $X_1$ and $Y_1$ or $X_2$ and $Y_2$, respectively, are not present.

It should be understood, that upon condensation of the DHDP molecule with the PA that a molecule of water, for example, is generated such that a bond is formed as described above (amide, ether, ester, urea, carbonate or urethane).

In particular, DHPD molecules include dopamine, 3,4-dihydroxy phenylalanine (DOPA), 3,4-dihydroxyhydrocinnamic acid, 3,4-dihydroxyphenyl ethanol, 3, 4 dihydroxyphenylacetic acid, 3, 4 dihydroxyphenylamine, 3,4-dihydroxybenzoic acid, gallic acid, 2, 3, 4, trihydroxybenzoic acid and 3, 4 dihydroxycinnamic acid, etc.

The denotation "AA" refers to an optional amino acid moiety or segment comprising one or more amino acids. Of particular interest are those amino acids with polar side chains, and more particularly amino acids with polar side chains and which are weakly to strongly basic. Amino acids with polar acidic, polar-neutral, non-polar neutral side chains are within the contemplation of the present invention. For some applications non-polar side chain amino acids may be more important for maintenance and determination three-dimensional structure than, e.g., enhancement of adhesion. Suitable amino acids are lysine, arginine and histidine, with any of the standard amino acids potentially being useable. Non-standard amino acids are also contemplated by the present invention.

The denotation "PG" refers to an optional protecting group, and if absent, is a hydrogen atom. A "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

The denotation "a" refers to a value of 0 when no linker is present (a bond is formed between the terminal end reactive portions of a PA and a DHPD) or is 1 when a linker is present.

The denotation of "b" has a value of one or more, typically between about 1 and about 20, more particularly between about 1 and about 10 and most particularly between about 1 and about 5, e.g., 1 to 3 inclusive. It should be understood that the DHPD can be one or more DHPD different molecules when b is 2 or more The denotation of "c" refers to a value of from 0 to about 20. It should be understood that the AA can be one or more different amino acids if c is 2 or more. In one embodiment, the sum of b+c is between 1 to about 20, in particular between about 1 to about 10 and more particularly between about 1 and about 5.

The denotation of "n" refers to values from 3 to about 15. In particular, n is 3, 4, or 5.

Note that as indicated in formula I, DHPD and AA moieties can be segments or "blocks" and can be and often are interspersed such that the DHPD/AA portion of each "arm" molecule can be a random copolymer or a random "block" copolymer. Therefore, for example, formula I(a) comprises:

While generally conforming to structural formula I, the "arms" of the compositions of this invention are separately and independently the same or different.

The present invention provides in one embodiment, a multi-armed, poly (alkylene oxide) polyether, multihydroxy (dihydroxy)phenyl derivative (DHPD) having the general formula:

wherein

CA is a central atom that is carbon;

each Z, independently, is a C1 to a C6 linear or branched, substituted or unsubstituted alkyl group or a bond;

each PA, individually, is a substantially poly(alkylene oxide) polyether or derivative thereof;

each L, independently, optionally, is a linker or is a linking group selected from amide, ester, urea, carbonate or urethane linking groups;

each DHPD, independently, is a multihydroxy phenyl derivative;

each AA, independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker;

"b" has a value of one or more;

"c" has a value in the range of from 0 to about 20; and

"n" has a value of 4. Such materials are useful as adhesives, and more specifically, medical adhesives that can be utilized as sealants.

In one aspect, CA is a carbon atom and each Z is a methylene.

In another aspect, CA is a carbon atom, each Z is a methylene and each PA is a polyethylene oxide polyether that is a polyethylene oxide (PEG). The molecular weight of each PEG unit is between about 1,250 and about 12,500 daltons, in particular between about 2,500 and about 5,000 daltons.

In still another aspect, CA is a carbon atom, each Z is a methylene, each PA is a polyethylene oxide polyether that is a polyethylene oxide (PEG) and the linking group is an amide, ester, urea, carbonate or urethane. The molecular weight of each PEG unit is between about 1,250 and about 12,500 daltons, in particular between about 2,500 and about 5,000 daltons. In particular, the linking group is an amide, urethane or ester.

In still another aspect, CA is a carbon atom, each Z is a methylene, each PA is a polyethylene oxide polyether that is a polyethylene oxide (PEG), the linking group is an amide, ester, urea, carbonate or urethane and the DHDP is dopamine, 3,4-dihydroxyphenyl alanine, 3,4-dihydroxyphenyl ethanol or 3,4-dihydroxyhydrocinnamic acid (or combinations thereof). The molecular weight of each PEG unit is between about 1,250 and about 12,500 daltons, in particular between about 2,500 and about 5,000 daltons. In particular, the linking group is an amide, urethane or ester.

In still another aspect, CA is a carbon atom, each Z is a methylene, each PA is a polyethylene oxide polyether that is a polyethylene oxide (PEG), the linking group is an amide, ester, urea, carbonate or urethane, the DHPD is dopamine, 3,4-dihydroxyphenyl alanine, 3,4-dihydroxyphenyl ethanol or 3,4-dihydroxyhydrocinnamic acid (or combinations thereof) and each AA is lysine. The molecular weight of each PEG unit is between about 1,250 and about 12,500 daltons, in particular between about 2,500 and about 5,000 daltons. In particular, the linking group is an amide, urethane or ester.

In still another aspect, CA is a carbon atom, each Z is a methylene, each PA is a polyethylene oxide polyether that is a polyethylene oxide (PEG), the linking group is an amide, ester, urea, carbonate or urethane, the DHPD is dopamine, 3,4-dihydroxyphenyl alanine, 3,4-dihydroxyphenyl ethanol or 3,4-dihydroxyhydrocinnamic acid (or combinations thereof) and the PG is either a "Boc" or a hydrogen atom. The molecular weight of each PEG unit is between about 1,250 and about 12,500 daltons, in particular between about 2,500 and about 5,000 daltons. In particular, the linking group is an amide, urethane or ester.

In certain embodiments, "b" has a value of 1, 2, 3, or 4.

In certain embodiments, "c" has a value of zero, 1, 2, 3 or 4.

AA moieties can be segments or "blocks" and can be and often are interspersed such that the DHPD/AA portion of each "arm" molecule can be a random copolymer or a random or sequenced "block" copolymer. Therefore, for example, comprising the general formula:

wherein CA is a carbon atom, Z, PA, L, DHPD, AA, PG, "a", "b", "c" and "n" are as defined above and zz is from 1 to about 20, in particular from about 2 to about 10 and most particularly from about 4 to about 8.

In certain embodiment, molecules according to this invention may be represented by:

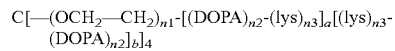

wherein a+b=1 meaning if a is 1 b is 0 and vice versa;

$n_1$ has a value in the range of about 10 to 500, preferably about 20 to about 250, and most preferably about 25 to about 100, for example, $n_1$ has value of between about 28 and 284 for PA of between about 1,250 and about 12,500 Da and in particular between about 56 and about 113 for a PA of between about 2,500 and about 5,000 Da;

$n_2$ has a value of 1 to about 10; $n_3$ has a value of 0 to about 10. In the above formula, it is to be understood that DOPA-lys (or other amino acids) peptide can be sequential or random.

Typically, formulations of the invention (the adhesive composition) have a solids content of between about 10% to about 50% solids by weight, in particular between about 15% and about 40% by weight and particularly between about 20% and about 35% by weight.

Exemplifying this invention, refined liquid adhesives possessing related chemical architecture were synthesized. The adhesive formulations depicted in FIG. 13 comprise a preferred branched, 4-armed poly(ethylene glycol) (PEG) end-functionalized with a single DOPA (C-(PEG-DOPA-Boc)$_4$), several DOPA residues (C-(PEG-DOPA$_4$)$_4$), a randomly alternating DOPA-lysine peptide (C-(PEG-DOPA$_3$-Lys$_2$)$_4$), a deaminated DOPA, 3,4-dihydroxyhydrocinnamic acid (C-(PEG-DOHA)$_4$), a dopamine through a urethane-linkage (C—(PEG-DMu)$_4$) and dopamine succinamic acid through an ester-linkage (C-(PEG-DMe)$_4$).

C-(PEG)-(DOHA)$_4$ is also sometimes referred to as Quadra Seal-DH herein. Regardless of polymer formulation, DOPA provides both adhesive and cohesive properties to the system, as it does in the naturally occurring MAPs. Without wishing to be bound to a theory, it is believed that the addition of the preferred amino acid lysine, contributes to adhesive interactions on metal oxide surfaces through electrostatic interactions with negatively charged oxides. Cohesion or crosslinking is achieved via oxidation of DOPA catechol by sodium periodate (NaIO$_4$) to form reactive quinone. It is further theorized, again without wishing to be bound by a theory, that quinone can react with other nearby catechols and functional groups on surfaces, thereby achieving covalent crosslinking.

The phrase "pharmaceutically acceptable carrier" means a pharmaceutically-acceptable material, composition or vehicle, such as a liquid or solid filler, diluent, excipient, solvent or encapsulating material that can be combined with the adhesive compositions of the invention. Each carrier should be "acceptable" in the sense of being compatible with the other ingredients of the composition and not injurious to the individual. Some examples of materials which may serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; phosphate buffered saline with a neutral pH and other non-toxic compatible substances employed in pharmaceutical formulations.

Additional terms/abbreviations useful throughout the application include:

Medhesive-022=PEU-1
Medhesive-023=PEU-2
Medhesive-024=PEEU-1
Medhesive-026=PEU-3
Medhesive-027=PEEU-3
Medhesive-038=Medhesive-022, wherein a 2 k PEG is used wherein a 1 k PEG is used in Medhesive-022
Nerites-1=QuadraSeal-DH
Nerites-2=Mehesive-023
Nerites-3=Mehesive-038
Nerites-4=Mehesive-026
Nerites-5=Mehesive-024
Nerites-6=Mehesive-027
Nerites-7=Mehesive-030
Nerites-8=Mehesive-043

The following paragraphs enumerated consecutively from 1 through 27 provide for various aspects of the present invention. In one embodiment, in a first paragraph (1), the present invention provides a bioadhesive construct, comprising: a support suitable for tissue repair or reconstruction; and a coating comprising a multihydroxyphenyl (DHPD) functionalized polymer (DHPp).

2. The bioadhesive construct of paragraph 1, further comprising an oxidant.

3. The bioadhesive construct of either of paragraphs 1 or 2, wherein the oxidant is formulated with the coating.

4. The bioadhesive of either of paragraphs 1 or 2, wherein the oxidant is applied to the coating.

5. The bioadhesive construct of any of paragraphs 1 through 3, wherein the support is a film, a mesh, a membrane, a nonwoven or a prosthetic.

6. The bioadhesive construct of paragraph 4, wherein the support is a film, a mesh, a membrane, a nonwoven or a prosthetic.

7. The bioahesive construct of any of paragraphs 1 through 3 or 5, wherein the construct is hydrated.

8. The bioadhesive construct of either of paragraphs 4 or 6, wherein the construct is hydrated.

9. The bioadhesive construct of any of paragraphs 1 through 3 or 5, or any of paragraphs 4, 6 or 8, wherein the DHPp polymer comprises the formula:

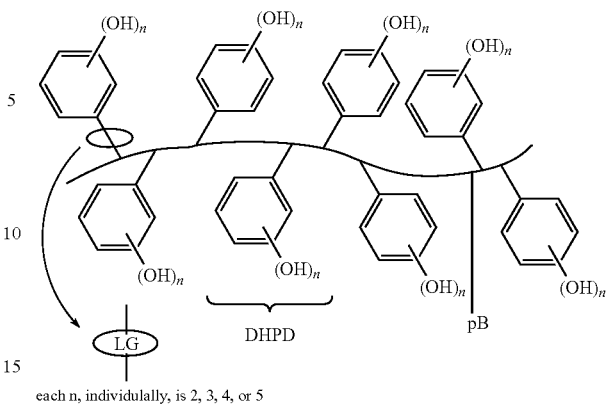

each n, individulally, is 2, 3, 4, or 5 wherein LG is an optional linking group or linker, DHPD is a multihydroxyphenyl group, each n, individually, is 2, 3, 4 or 5, and pB is a polymeric backbone.

10. The bioadhesive construct of paragraph 9, wherein the DHPD comprises at least about 1 to 100 weight percent of the DHPp.

11. The bioadhesive construct of paragraph 9, wherein the DHPD comprises at least about 2 to about 65 weight percent of the DHPp.

12. The bioadhesive construct of paragraph 9, wherein the DHPD comprises at least about 3 to about 55 weight percent of the DHPp.

13. The bioadhesive construct of paragraph 9, wherein the pB consists essentially of a polyalkylene oxide.

14. The bioadhesive construct of paragraph 9, wherein the pB is substantially a homopolymer.

15. The bioadhesive construct of paragraph 9, wherein the pB is substantially a copolymer.

16. The bioadhesive construct of any of paragraphs 9 through 15, wherein the DHPD is a 3, 4 dihydroxy phenyl.

17. The bioadhesive construct of any of paragraphs 9 through 16, wherein the DHPD's are linked to the pB via a urethane, urea, amide, ester, carbonate or carbon-carbon bond.

18. The bioadhesive construct of any of paragraphs 1 through 3 or 5, or any of paragraphs 4, 6 or 8, wherein the DHPp polymer comprises the formula:

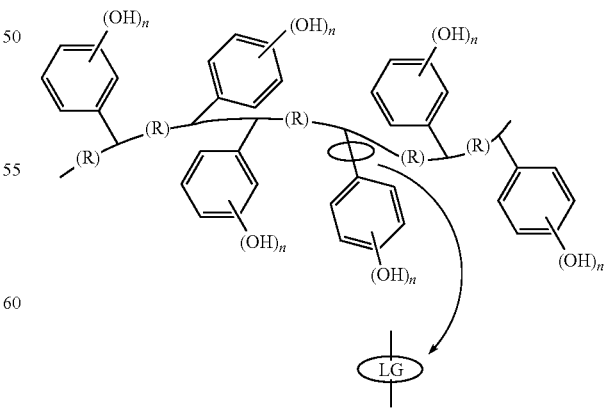

each n, individulally, is 2, 3, 4, or 5 wherein R is a monomer or prepolymer linked or polymerized to form pB, pB is a polymeric backbone, LG is an optional linking group or linker and each n, individually, is 2, 3, 4 or 5.

19. The bioadhesive construct of paragraph 18, wherein R is a polyether, a polyester, a polyamide, a polyacrylate a polymethacrylate or a polyalkyl.

20. The bioadhesive construct of either of paragraphs 18 or 19, wherein the DHPD is a 3, 4 dihydroxy phenyl.

21. The bioadhesive construct of any of paragraphs 18 through 20, wherein the DHPD's are linked to the pB via a urethane, urea, amide, ester, carbonate or carbon-carbon bond.

22. The bioadhesive of any of paragraphs 1 through 3 or 5, or any of paragraphs 4, 6 or 8, wherein the functionalized DHPp comprises the formula:

wherein

CA is a central atom that is carbon;

each Z, independently, is a C1 to a C6 linear or branched, substituted or unsubstituted alkyl group or a bond;

each PA, independently, is a substantially poly(alkylene oxide) polyether or derivative thereof;

each L, independently, optionally, is a linker or is a linking group selected from amide, ester, urea, carbonate or urethane linking groups;

each DHPD, independently is a multihydroxy phenyl derivative;

each AA independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker;

"b" has a value of one or more;

"c" has a value in the range of from 0 to about 20; and

"n" has a value of 4.

23. The bioadhesive construct of paragraph 22, wherein each DHPD is either dopamine, 3,4-dihydroxyphenyl alanine, 2-phenyl ethanol or 3,4-dihydroxyhydrocinnamic acid.

24. The bioadhesive construct of either of paragraphs 22 or 23, wherein the linking group is an amide, urea or urethane.

25. The bioadhesive construct of any of paragraphs 1 through 3 or 5, or any of paragraphs 4, 6 or 8, wherein the DHPp polymer comprises the formula:

wherein

CA is a central atom selected from carbon, oxygen, sulfur, nitrogen, or a secondary amine;

each Z, independently is a C1 to a C6 linear or branched, substituted or unsubstituted alkyl group or a bond;

each PA, independently, is a substantially poly(alkylene oxide) polyether or derivative thereof;

each L, independently, optionally, is a linker or is a linking group selected from amide, ester, urea, carbonate or urethane linking groups;

each DHPD, independently, is a multihydroxy phenyl derivative;

each AA, independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker;

"b" has a value of one or more;

"c" has a value in the range of from 0 to about 20; and

"n" has a value from 3 to 15.

26. A method to repair tissue, comprising the steps: applying the bioadhesive construct of any of paragraphs 1 through 3 or 5 to the tissue or prosthetic and allowing the construct to adhere to the tissue or prosthetic.

27. A method to repair tissue, comprising the steps: applying the bioadhesive construct of any of paragraphs 4, 6 or 8 to the tissue or prosthetic; contacting the oxidant to the functionalized polymer and allowing the construct to adhere to the tissue or prosthetic.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES FROM Ser. No. 11/834,651

Example 1

Synthesis of DMA1

20 g of sodium borate, 8 g of $NaHCO_3$ and 10 g of dopamine HCl (52.8 mmol) were dissolved in 200 mL of $H_2O$ and bubbled with Ar. 9.4 mL of methacrylate anhydride (58.1 mmol) in 50 ml of THF was added slowly. The reaction was carried out overnight and the reaction mixture was washed twice with ethyl acetate and the organic layers were discarded. The aqueous layer was reduced to a pH<2 and the crude product was extracted with ethyl acetate. After reduction of ethyl acetate and recrystallization in hexane, 9 g of DMA1 (41 mmol) was obtained with a 78% yield. Both $^1H$ and $^{13}C$ NMR was used to verify the purity of the final product.

Example 2

Synthesis of DMA2

20 g of sodium borate, 8 g of $NaHCO_3$ and 10 g of dopamine HCl (52.8 mmol) were dissolved in 200 mL of $H_2O$ and bubbled with Ar. 8.6 mL acryloyl chloride (105 mmol) in 50 mL THF was then added dropwise. The reaction was carried out overnight and the reaction mixture was washed twice with ethyl acetate and the organic layers were discarded. The aqueous layer was reduced to a pH<2 and the crude product was extracted with ethyl acetate. After reduction of ethyl acetate and recrystallization in hexane, 6.6 g of DMA2 (32 mmol) was obtained with a 60% yield. Both $^1H$ and $^{13}C$ NMR was used to verify the purity of the final product.

Example 3

Synthesis of DMA3

30 g of 4,7,10-trioxa-1,13-tridecanediamine (3EG-diamine, 136 mmol) was added to 50 mL of THF. 6.0 g of di-tert-butyl dicarbonate (27.2 mmol) in 30 mL of THF was added slowly and the mixture was stirred overnight at room temperature. 50 mL of deionized water was added and the solution was extracted with 50 mL of DCM four times. The combined organic layer was washed with saturated NaCl and dried over $MgSO_4$. After filtering $MgSO_4$ and removing DCM through reduced pressure, 8.0 g of Boc-3EG-$NH_2$ was obtained. Without further purification, 8.0 g of Boc-3EG-$NH_2$ (25 mmol) and 14 mL of triethyl amine ($Et_3N$,100 mmol) were add to 50 mL of DCM and placed in an ice water bath. 16 mL of methacrylic anhydride (100 mmol) in 35 mL of DCM was added slowly and the mixture was stirred overnight at room temperature. After washing with 5% $NaHCO_3$, 1N HCl, and saturated NaCl and drying over $MgSO_4$, the DCM layer was reduced to around 50 mL. 20 mL of 4N HCl in dioxane was added and the mixture was stirred at room temperature for 30 min. After removing the solvent mixture and drying the crude product in a vacuum, the crude product was further purified by precipitation in an ethanol/hexane mixture to yield 9.0 g of MA-3EG-$NH_2$HCl. 9.0 g of MA-3EG-$NH_2$HCl was dissolved in 100 mL of DCM and 6.1 g of 3,4-dihydroxyhydrocinnamic acid (DOHA, 33.3 mmol) in 50 mL of DMF, 4.46 g of 1-hydroxybenzotriazole hydrate (HOBt, 33.3 mmol), 12.5 g of 2-(1H-Benzotriazole-1-yl)-1,1,3,3-tetramethyluronium hexafluorophosphate (HBTU, 33.3 mmol), and 4.67 mL of $Et_3N$ (33.3 mmol) were added. The mixture was stirred for 3 hrs at room temperature. The reaction mixture was extensively washed with 1N HCl and saturated NaCl. The organic layer was dried to yield 860 mg of DMA3. Both $^1H$ and $^{13}C$ NMR was used to verify the purity of the final product.

Example 4

Synthesis of PDMA-1

20 mL of poly(ethylene glycol) methyl ether methacrylate (EG9ME, Mw=475) was passed through 30 g of $Al_2O_3$ to remove inhibitors. 2.0 g of DMA-1 (9.0 mmol), 4.7 g of EG9ME (9.8 mmol), and 62 mg of AIBN (0.38 mmol) were dissolved in 15 mL of DMF. Atmospheric oxygen was removed through freeze-pump-thaw treatment three times and replaced with Ar. While under vacuum, the reaction mixture was incubated at 60° C. for 5 hours and precipitated by adding to 50 mL of ethyl ether. After drying, 4 g of a clear sticky solid was obtained (Gel permeation chromatography in concert with light scattering (GPC): $M_w$=430,000, PD=1.8; $^1H$ NMR: 24 wt % DMA1).

Example 5

Synthesis of PDMA-22

987 mg of DMA1 (4.5 mmol), 10 g of N-isopropyl acrylamide (NIPAM, 88.4 mmol), 123 mg of AIBN (0.75 mmol), and 170 mg of cysteamine hydrochloride (1.5 mmol) were dissolved in 50 mL of DMF. Atmospheric oxygen was removed through freeze-pump-thaw treatment three times and replaced with Ar. While under vacuum, the reaction mixture was incubated at 60° C. overnight and precipitated by adding to 450 mL of ethyl ether. The polymer was filtered and further precipitated in chloroform/ethyl ether. After drying, 4.7 g of white solid was obtained (GPC: $M_w$=81,000, PD=1.1; UV-vis: 11±0.33 wt % DMA1).

Example 6

Synthesis of PEU-1

20 g (20 mmol) of PEG-diol (1000 MW) was azeotropically dried with toluene evaporation and dried in a vacuum dessicator overnight. 105 mL of 20% phosgene solution in toluene (200 mmol) was added to PEG dissolved in 100 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for four hours with Ar purging, after which the solvent was removed with rotary evaporation. The resulting PEG-dCF was dried with a vacuum pump overnight and used without further purification.

PEG-dCF was dissolved in 50 mL of chloroform and the mixture was kept in an icewater bath. 7.0 g of 4-nitrophenol (50 mmol) and 6.2 mL of triethylamine (440 mmol) in 50 mL of DMF was added dropwise in an Ar atmosphere and the mixture was stirred at room temperature for three hrs. 8.6 g of lysine tetrabutylammonium salt (Lys-TBA, 20 mmol) in 50 mL of DMF was added dropwise over 15 min and the mixture was stirred at room temperature for 24 hrs. 5.7 g of dopamine-HCl (30 mmol), 4.2 mL of triethylamine (30 mmol), 3.2 g of HOBt (24 mmol), and 9.1 g of HBTU (24 mmol) were added and the mixture was further stirred at room temperature for two hours. Insoluble particles were filtered and the filtrate was added to 1.7 L of ethyl ether. After sitting at 4° C. overnight, the supernatant was decanted and the precipitate was dried with a vacuum pump. The crude product was further purified by dialyzing (3,500 MWCO) in deionized water acidified to pH 3.5 with HCl for two days. After freeze drying, 15 g of gooey white product was obtained. (GPC: Mw=200,000; UV-vis: 13±1.3 wt % dopamine)

Example 7

Synthesis of PEE-1

8 g of 1000 MW PEG-diol (8 mmol), 2 g of Cbz-Asp-Anh (8 mmol), and 3.1 mg of p-toluenesulfonic salt (0.016 mmol) were dissolved in 50 mL of toluene in a round bottom flask equipped with a Dean-Stark apparatus and a condensation column. While purging with Ar, the mixture was stirred in a 145° C. oil bath for 20 hrs. After cooling to room temperature, toluene was removed by rotoevaporation and the polymer was dried in a vacuum. 23.8 µL of titanium(IV) isopropoxide was added and the mixture was stirred under vacuum (0.5 torr) in a 130° C. oil bath for 18 hrs. 60 mL of chloroform was added and the solution was filtered into 450 mL of ethyl ether. The precipitated polymer was filtered and dried under vacuum to yield 6 g of p(EG1k-CbzAsp) (GPC: Mw=65,000, PD=4.0).

5 g of p(EG1k-CbzAsp) was dissolved in 30 mL of DMF and purged with Ar for 20 min. 10 g of 10 wt % palladium loaded on carbon (Pd/C) was added and 155 mL of formic acid was added dropwise. The mixture was stirred under Ar overnight and Pd/C was filtered and washed with 200 mL of 1N HCl. The filtrate was extracted with DCM and the organic layer was dried over $MgSO_4$. $MgSO_4$ was filtered and DCM was reduced to around 50 mL and added to 450 mL of ethyl ether. The resulting polymer was filtered and dried under vacuum to yield 2.1 g of p(EG1k-Asp) (GPC: Mw=41,000, PD=4.4).

2.1 g of p(EG1k-Asp) (1.77 mmol —$NH_2$) was dissolved in 30 mL of DCM and 15 mL of DMF. 842 mg of N-Boc-DOPA (2.83 mmol), 382 mg of HOBt (2.83 mmol), HBTU (2.83 mmol), and 595 µL of $Et_3N$ (4.25 mmol) were added. The mixture was stirred for 1 hr at room temperature and added to 450 mL ethyl ether. The polymer was further precipitated in cold MeOH and dried in vacuum to yield 1.9 g of PEE-1 (GPC: Mw=33,800, PD=1.3; UV-vis: 7.7±1.3 wt % DOPA).

Example 8

Synthesis of PEE-5

50 g of PEG-diol (1,000 MW, 50 mmol) and 200 mL of toluene were stirred in a 3-necked flask equipped with a Dean-Stark apparatus and a condensation column. While purging under Ar, the PEG was dried by evaporating 150 mL of toluene in a 145° C. oil bath. After the temperature of the mixture cooled to room temperature, 100 mL of DCM was added and the polymer solution was submerged in an ice water bath. 17.5 mL of $Et_3N$ (125 mmol) in 60 mL of DCM and 5.7 mL of fumaryl chloride (50 mmol) in 70 mL of DCM were added dropwise and simultanesously over 30 min. The mixture was stirred for 8 hrs at room temperature. Organic salt was filtered out and the filtrate was added to 2.7 L of ethyl ether. After precipitating once more in DCM/ethyl ether, the polymer was dried to yield 45.5 g of p(EG1k-Fum) (GPC: Mw=21,500, PD=3.2).

45 g of p(EG1k-Fum) (41.7 mmol of fumarate vinyl group), 36.2 mL of 3-mercaptopropionic acid (MPA, 417 mmol), and 5.7 g of AIBN were dissolved in 300 mL of DMF. The solution was degassed three times with freeze-pump-thaw cycles. While sealed under vacuum (5 torr), the mixture was stirred in a 60° C. water bath overnight. The resulting polymer was precipitated twice with ethyl ether and dried to yield 41.7 g of p(EG1kf-MPA) (GPC: Mw=14,300, PD=2.3)

41 g of p(EG1kf-MPA) was dissolved in 135 mL of DMF and 270 mL of DCM. 10.5 g of dopamine HCl (55.4 mmol), 7.5 g of HOBt (55.4 mmol), 20.9 g of HBTU (55.4 mmol), and 11.6 mL of $Et_3N$ (83 mmol) were added. The mixture was stirred for 2 hrs at room temperature and then added to 2.5 L of ethyl ether. The polymer was further purified by dialysis using 3500 MWCO dialysis tubing in deionized water for 24 hrs. After lyophilization, 30 g of PEE-5 was obtained (GPC-LS: Mw=21,000, PD=2.0; UV-vis: 9.4±0.91 wt % dopamine).

Example 9

Synthesis of PEE-9

4 g of HMPA (30 mmol) and 6 g of PEG-diol (600 MW, 10 mmol) were dissolved in 20 mL of chloroform, 20 mL of THF, and 40 mL of DMF. While stirring in an ice water bath with Ar purging, 4.18 mL of succinyl chloride (38 mmol) in 30 mL of chloroform and 14 mL of $Et_3N$ (100 mmol) in 20 mL of chloroform were added simultaneously and dropwise over 3.5 hrs. The reaction mixture was stirred at room temperature overnight. The insoluble organic salt was filtered out and the filtrate was added to 800 mL of ethyl ether. The precipitate was dried under a vacuum to yield 8 g of p(EG600DMPA-SA) ($^1$H NMR: HMPA:PEG=3:1).

8 g of p(EG600DMPA-SA) (10 mmol —COOH) was dissolved in 20 mL of chloroform and 10 mL of DMF. 3.8 g of HBTU (26 mmol), 1.35 g of HOBt (10 mmol), 2.8 g of dopamine HCl (15 mmol), and 3.64 mL of $Et_3N$ (26 mmol) were added and the reaction mixture was stirred for an hour. The mixture was added to 400 mL of ethyl ether and the precipitated polymer was further purified by dialyzing using 3500 MWCO dialysis tubing in deionized water for 24 hrs. After lyophilization, 600 mg of PEE-9 was obtained (GPC-LS: Mw=15,000, PD=4.8; UV-vis: 1.0±0.053 μmol dopamine/mg polymer, 16±0.82 wt % dopamine).

Example 10

Synthesis of PEA-2

903 mg of Jeffamine ED-2001 (0.95 mmol —$NH_2$) in 10 mL of THF was reacted with 700 mg of Cbz-DOPA-NCA (1.4 mmol) and 439 mg of Cbz-Lys-NCA (1.41 mmol) for three days. 293 μL of triethylamine (2.1 mmol) was added to the mixture and 105 μL of succinyl chloride (0.95) was added dropwise and stirred overnight. After precipitating the polymer in ethyl ether and drying under a vacuum, 800 mg of solid was obtained. ($^1$H NMR: 0.6 Cbz-DOPA and 2.2 Cbz-Lys per ED2k)

The dried compound was dissolved in 4 mL of MeOH and Pd (10 wt % in carbon support) was added with Ar purging. 12 mL of 1 N formic acid was added dropwise and the mixture was stirred overnight under Ar atmosphere. 20 mL 1 N HCl was added and Pd/C was removed by filtration. The filtrate was dialyzed in deionized water (3,500 MWCO) for 24 hours. After lyophilization, 80 mg of PEA-2 was obtained. (GPC: Mw=16,000; PD=1.4; UV-vis: 3.6 wt % DOPA)

Example 11

Synthesis of GEL-1

3.3 g of DOHA (18.3 mmol) was dissolved in 25 mL of DMSO and 35 mL of 100 mM MES buffer (pH 6.0, 300 mM NaCl) and 3.5 g of EDC (18.3 mmol) and 702 mg of NHS (6.1 mmol) were added. The mixture was stirred at room temperature for 10 min and 10 g of gelatin (75 bloom, Type B, Bovine) was dissolved in 100 mL of 100 mM MES buffer (pH 6.0, 300 mM NaCl) was added. The pH was adjusted to 6.0 with concentrated HCl and the mixture was stirred at room temperature overnight. The mixture was added to dialysis tubing (15,000 MWCO) and dialyzed in deionized water acidified to pH 3.5 for 24 hrs. After lyophilization, 5.1 g of GEL-1 was obtained (UV-vis: 8.4±0.71 DOHA per gelatin chain, 5.9±0.47 wt % DOHA).

Example 12

Synthesis of GEL-4

10 g of gelatin (75 bloom, Type B, Bovine) was dissolved in 200 mL of 100 mM MES buffer (pH 6.0, 300 mM NaCl). 2.3 g of cysteamine dihydrochloride (10.2 mmol) was added and stirred until it dissolved. 1.63 g of EDC (8.5 mmol) and 245 mg of NHS (2.1 mmol) were added and the mixture was stirred overnight at room temperature. The pH was raised to 7.5 by adding 1 N NaOH, and 9.44 g of DTT (61.2 mmol) was added. The pH of the solution was increased to 8.5 and the mixture was stirred at room temperature for 24 hrs. The pH was reduced to 3.5 by adding 6 N HCl, and the reaction mixture was dialyzed using 15,000 MWCO dialysis tubing with deionized water acidified to pH 3.5 for 24 hrs. The solution was lyophilized to yield 7.5 g of Gelatin-g-CA (UV-vis: 0.46±0.077 μmol CA/mg polymer or 11±1.8 CA per gelatin chain).

7.5 g of Gelatin-g-CA (3.4 mmol —SH) was dissolved in 100 mL of 12.5 mM acetic acid. 279 mg of AIBN (1.7 mmol) in 20 mL of MeOH and 3.73 g of DMA1 (17 mmol) were added and the mixture was degassed with two cycles of freeze-pump-thaw cycles. While sealed under Ar, the mixture was stirred in an 85° C. oil bath overnight. The mixture was dialyzed using 15,000 MWCO dialysis tubing with deionized water acidified to pH 3.5 for 24 hrs. The solution was lyophilized to yield 4.5 g of GEL-4 (UV-vis: 54 wt % DMA1, 128±56 DMA1 per gelatin chain).

Example 13

Synthesis of GEL-5

9 g of gelatin (75 bloom, Type B, Bovine) was dissolved in 100 mL of deionized water. 150 mg of AIBN (0.91 mmol) in 1 mL of DMF was added and the mixture was degassed with Ar bubbling for 20 min. The mixture was stirred in a 50° C. water bath for 10 min. 1.0 g of DMA1 (4.6 mmol) in 10 mL of MeOH was added dropwise and the mixture was stirred at 60° C. overnight. The reaction mixture was added to 750 mL of acetone and the precipitate was further purified by dialyzing in deionized water (using 3,500 MWCO dialysis tubing) for 24 hrs. The solution was precipitated in acetone and the polymer was dried in a vacuum desiccator to yield 5.0 g of GEL-5 (UV-vis: 17 wt % DMA1, 21±2.3 DMA1 per gelatin chain).

EXAMPLES FROM Ser. No. 12/099,254

It should be understood that throughout the specification different abbreviations may be used for certain of the compounds. For example, C-(PEG-DOPA-Boc)$_4$ equals PEG10k-(D)$_4$, C-(PEG-DOPA$_4$)$_4$ equals PEG10k-(D$_4$)$_4$, C-(PEG-DOPA$_3$-Lys$_2$)$_4$ equals PEG10k-(DL)$_4$, C-(PEG-DOHA)$_4$ equals PEG10k-(DH)$_4$, C-(PEG-DMu)$_4$ equals PEG10k-(DMu)$_4$ and C-PEG-DMe)$_4$ equals PEG10k-(DMe)$_4$.

Detailed descriptions of the synthesis, curing, and adhesive experimentation for these adhesive polymers is as follow:

Synthesis of C-(PEG-DOPA-Boc)$_4$, C-(PEG-DOHA)$_4$ (QuadraSeal-DH), and C-(PEG-DMe)$_4$ C-(PEG-DOPA-Boc)$_4$ was synthesized by dissolving branched PEG-NH$_2$ (MW=10,000 Da) in a 2:1 DCM:DMF to make a 45 mg/mL polymer solution. 1.6 molar equivalent (relative to —NH$_2$) of N-Boc-DOPA, 1-hydroxybenzotriazole hydrate, and O-(Benzotriazol-1-yl)-N,N,N',N'-tetramethyluronium hexafluorophosphate were then added. 2.4 equivalent of triethylamine was finally added and the mixture was stirred at room temperature for 1 hour. Polymer purification was performed by precipitation in diethyl ether and cold methanol.

C-(PEG-DOHA)$_4$ (m=56) was synthesized as described above using 3,4-dihydroxy-hydrocinnamic acid (DOHA) instead of N-Boc-DOPA. The resulting polymer was purified by precipitation in diethyl ether followed by dialysis with deionized water (3500 MWCO) for 24 hours. Subsequent lyophilization yielded C-(PEG-DOHA)$_4$ (m=56), FIG. 13d.

C-(PEG-DOHA)$_4$ (m=113) was synthesized as described above using 3,4-dihydroxy-hydrocinnamic acid (DOHA) instead of N-Boc-DOPA and PEG-NH$_2$ (MW=20,000 Da). The resulting polymer was purified by precipitation in diethyl ether followed by dialysis with deionized water (3500 MWCO) for 24 hours. Subsequent lyophilization yielded C-(PEG-DOHA)$_4$ (m=113).

C-(PEG-DMe)$_4$ was synthesized by first reacting branched PEG-OH (MW=10,000 Da) with 5 times excess (relative to —OH) of succinic anhydride and catalytic amount of pyridine in chloroform at 70° C. for 18 hrs. After repeated precipitation in chloroform/ethyl ether, the resulting C-(PEG-SA)$_4$ is further reacted with 1.6 equivalent of dopamine hydrochloride using similar procedures as described above. The resulting polymer was purified by precipitation in diethyl ether followed by dialysis with deionized water acidified to pH 3.5 with hydrochloric acid (3500 MWCO) for 24 hours. Subsequent lyophilization yielded C-(PEG-DMe)$_4$.

Synthesis of C-(PEG-DOPA$_4$)$_4$ (QuadraSeal-D4) and C-(PEG-DOPA$_3$-Lys$_2$)$_4$.

N-carboxyanhydrides (NCAs) of DOPA (diacetyl-DOPA-NCA) and lysine (Fmoc-Lys-NCA) were prepared by following literature procedures [1,2]. Four-armed PEG-NH$_2$ (MW=10,000 Da) was first dried by azeotropic evaporation with benzene and dried in a desiccator for ≧3 h. Ring-opening polymerization of NCA was performed by dissolving 4-armed PEG-NH$_2$ in anhydrous THF at 100 mg/mL and purged with argon. Six molar excess (relative to —NH$_2$) of diacectyl-DOPA-NCA with or without Fmoc-Lys-NCA was added neat. The reaction mixture was stirred at room temperature for 5 d with a dry tube outlet. The peptide-modified block copolymers were purified in succession with ethyl ether three times. Peptide-coupled PEG was dissolved in anhydrous DMF at a concentration of 50 mg/mL and bubbled with Ar for 10 min. Pyridine was added to make a 5% solution and stirred for 15 min with Ar bubbling. The mixture was rotary evaporated to remove excess pyridine and precipitated in ethyl ether. The crude polymer was further purified by dialyzing the compound in deionized water (MWCO 3500) for 4 hours and lyophilized to yield the final products.

Synthesis of PEG10k-(DMu)$_4$:

10 g of 4-armed PEG-OH (10,000 MW; 4 mmol —OH) was dried with azeotropic evaporation with toluene and dried in a vacuum desiccator. To PEG in 90 mL of toluene was added 10.6 mL of phosgene solution (20% phosgene in toluene; 20 mmol phosgene) and the mixture was stirred for 4 hrs in a 55° C. oil bath, with Ar purging and a NaOH solution trap in the outlet to trap escaped phosgene. The mixture was evaporated and dried with vacuum for overnight. 65 mL of chloroform and 691 mg of N-hydroxysuccinimide (6 mmol) were added to chloroformate-activated PEG and 672 mL of triethylamine (4.8 mmol) in 10 mL of chloroform was added dropwise. The mixture was stirred under Ar for 4 hrs. 1.52 g of dopamine-HCl (8 mmol), 2.24 mL of triethylamine (8 mmol), and 25 mL of DMF was added, and the polymer mixture was stirred at room temperature for overnight. 100 mL of chloroform was added and the solution was washed successively with 100 mL each of 12 mM HCl, saturated NaCl solution, and H$_2$O. The organic layer was dried over MgSO$_4$. MgSO$_4$ was removed by filtration and the filtrate was reduced to around 50 mL and added to 450 mL of diethyl ether. The precipitate was filter and dried to yield 8.96 g of PEG10k-(DMu)$_4$.

Additional Examples

Example

Synthesis of Medhesive-023

26 g (26 mmol) of PEG-diol (1000 MW) was azeotropically dried with toluene evaporation and dried in a vacuum dessicator overnight. 136 mL of 20% phosgene solution in toluene (260 mmol) was added to PEG dissolved in 130 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation. The resulting PEG-dCF was dried with a vacuum pump overnight and used without further purification.

PEG-dCF was dissolved in 50 mL chloroform, to which a mixture of 7.48 g of NHS (65 mmol), 9.1 mL of triethylamine (65 mmol) and 50 mL of DMF was added dropwise. The mixture was stirred at room temperature for 3 hrs under Argon. 11.2 g Lysine-TBA (26 mmol) was dissolved in 50 mL DMF and added dropwise over a period of 15 minutes. The mixture was stirred at room temperature for overnight. 9.86 g of HBTU (26 mmol), 3.51 g of HOBt (26 mmol) and 5.46 mL triethylamine (39 mmol) were added to the reaction mixture and stirred for 10 minutes, followed by the addition of 13.7 g Boc-Lys-TBA (26 mmol) in 25 mL DMF and stirred for an additional 30 minutes. Next, 7.4 g dopamine-HCl (39 mmol) and 14.8 g HBTU (39 mmol) were added to the flask and stirred for 1 hour, and the mixture was added to 1.6 L of diethyl ether. The precipitate was collected with vacuum filtration and dried. The polymer was dissolved in 170 mL chloroform and 250 mL of 4M HCl in dioxane were added. After 15 minutes of stirring, the solvents were removed via rotary evaporation and the polymer was dried under vacuum. The crude polymer was further purified using dialysis with 3500 MWCO tubes in 7 L of water (acidified to pH 3.5) for 2 days. Lyophilization of the polymer solution yielded 16.6 g of Medhesive-023. $^1$H NMR confirmed chemical structure; UV-vis: 0.54±0.026 μmol dopamine/mg polymer, 8.2±0.40 wt % dopamine.

Example

Synthesis of Medhesive-024 Also Referred to as PEEU-1

18.9 g (18.9 mmol) of PEG-diol (1000 MW) was azeotropically dried with toluene evaporation and dried in a vacuum dessicator overnight. 100 mL of 20% phosgene solution in toluene (189 mmol) was added to PEG dissolved in 100 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation. The resulting PEG-dCF was dried with a vacuum pump overnight and used without further purification.

PEG-dCF was dissolved in 50 mL of chloroform and the mixture was kept in an icewater bath. 5.46 g of NHS (47.4 mmol) and 5.84 mL of triethylamine (41.7 mmol) in 20 mL of DMF was added dropwise to the PEG solution. And the mixture was stirred at room temperature for 3 hrs. Polycaprolactone diglycine touluene sulfonic salt (PCL-(GlyTSA)$_2$) PCL=1250 Da) in 50 mL of chloroform was added. 2.03 g of Lysine (13.9 mmol) was freeze dried with 9.26 mL of 1.5 M tetrabutyl ammonium hydroxide and the resulting Lys-TBA salt in 50 mL DMF was added. The mixture was stirred at room temperature for 24 hrs. 5.39 g of dopamine HCl (28.4 mmol), 8.61 g of HBTU (22.7 mmol), 3.07 g of HOBt (22.7 mmol) and 3.98 mL triethylamine (28.4 mmol) were added. Stirred at room temperature for 1 hr and the mixture was added to 2 L ethyl ether. The precipitate was collected with vacuum filtration and the polymer was further dialyzed with 3500 MWCO tubes in 8 L of water (acidified to pH 3.5) for 2 days. Lyophilization of the polymer solution yielded 12 g of Medhesive-024. $^1$H NMR indicated 62 wt % PEG, 25 wt % PCL, 7 wt % lysine, and 6 wt % dopamine.

Example

Synthesis of Medhesive-026

36 g (18.9 mmol) of PEG-PPG-PEG (1900 MW) was azeotropically dried with toluene evaporation and dried in a vacuum dessicator overnight. 100 mL of 20% phosgene solution in toluene (189 mmol) was added to PEG dissolved in 100 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation. The resulting PEG-dCF was dried with a vacuum pump overnight and used without further purification.

A solution containing 5.46 g of NHS (67.4 mmol) in 50 mL of DMF and 5.84 mL of triethylamine (41.7 mmol) was added dropwise over 10 minutes to the ClOC—O-PEG-PPC-PEG-O—COCl dissolved in 50 mL of chloroform in an ice bath. The resulting mixture was stirred at room temperature for 3 hrs with argon purging. 9.3 g of Lysine (37.8 mmol) was freeze dried with 25.2 mL of 1.5 M tetrabutyl ammonium hydroxide and Lys-TBA salt (18.9 mmol) in 50 mL DMF was added over 5 minutes. The mixture was stirred at room temperature for 24 hours. 5.39 g of dopamine HCl (28.4 mmol), 8.11 g of HBTU (22.7 mmol), 3.07 g of HOBt (22.7 mmol) and 3.98 mL triethylamine (28.4 mmol) were added along with 50 mL chloroform. The solution was stirred at room temperature for 1 hr and the mixture filtered using coarse filter paper into 2.0 L of ethyl ether and placed in 4° C. for overnight. The precipitate was collected with vacuum filtration and dried under vacuum. The polymer was dissolved in 200 mL methanol and dialyzed with 3500 MWCO tubes in 7 L of water (acidified to pH 3.5) for 2 days. Lyophilization of the polymer solution yielded 19 g of Medhesive-026. $^1$H NMR confirmed chemical structure and showed ~70% coupling of dopamine; UV-vis: 0.354±0.031 mmol dopamine/mg polymer, 4.8±0.42 wt % dopamine.

Example

Synthesis of Medhesive-027

22.7 g (37.8 mmol) of PEG-diol (600 MW) was azeotropically dried with toluene evaporation and dried in a vacuum dessicator overnight. PEG600 was dissolved in 200 mL toluene and 200 mL (378 mmol) phosgene solution was added in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation and the polymer was dried for 24 hours under vacuum to yield PEG600-dCF.

1.9 g (1.9 mmol) PEG-diol (1000 MW) was azeotropically dried with toluene evaporation and dried in a vacuum dessicator overnight. Dissolved PEG1000 in 10 mL toluene and added 10 mL (19 mmol) phosgene solution. The 1 k MW PEG solution was heated to 60 C. in a round bottom flask equipped with a condensation flask, an argon inlet, and an outlet to a solution of 20 wt % NaOH in 50% MeOH to trap escaped phosgene and stirred for 3 hours. The toluene was removed with rotary evaporation and further dried with vacuum to yield PEG1000-dCF.

7.6 g (3.8 mmol) of PCL-diol (2000 MW), 624.5 mg (8.32 mmol) Glycine, and 1.58 g (8.32 mmol) pTSA-H$_2$O were dissolved in 50 mL toluene. The reaction mixture was refluxed at 140-150° C. for overnight. The resulting PCL(Gly-TSA)$_2$ was cooled to room temperature and any solvents were removed with rotary evaporation and further dried under vacuum. PCL(Gly-TSA)$_2$ was dissolved in 50 mL chloroform and 5 mL DMF and 1.17 mL (8.32 mmol) triethylamine was added. The reaction flask was submerged in an ice water bath while stirring. Next, PEG1k-dCF in 30 mL chloroform was added dropwise while Ar purging. This mixture was stirred overnight at room temperature to form [EG1kCL2kG].

10.9 g (94.6 mmol) NHS was dissolved in 50 mL DMF, 11.7 mL (83.2 mmol) triethylamine and 70 mL chloroform. This NHS/triethylamine mixture was added dropwise to PEG600-dCF dissolved in 150 mL chloroform stirring in an ice water bath. The reaction mixture was stirred at room temperature overnight to form PEG600(NHS)$_2$.

5.25 g (35.9 mmol) Lysine was dissolved in 23.9 mL (35.9 mmol) 1.5M TBA and 30 mL water and freeze-dried. 8.84 g BOC-Lys (3.59 mmol) was dissolved in 23.9 mL (35.9 mmol) 1.5M TBA and 40 mL water and freeze-dried to yield Boc-Lys-TBA.

[EG1kCL2kG] was added dropwise to PEG600(NHS)$_2$ over a period of 10 minutes. Lys-TBA was dissolved in 75 mL DMF and added dropwise. The reaction mixture was stirred for 24 hours. Next 4.85 g HOBt (35.9 mmol), 13.6 g HBTU (35.9 mmol), and 20 mL triethylamine (35.9 mmol) were added and the mixture stirred for 10 minutes, followed by the addition of BOC-Lys-TBA in 50 mL DMF. Stirred for an additional 30 minutes. Added 20.5 g (108 mmol) dopamine-HCl, 9.72 g (71.9 mmol) HOBT and 29.3 (71.9 mmol) HBTU and stirred for 2 hours and added the reaction mixture to 2.4 L diethyl ether. The precipitate was collected by decanting the supernatant and drying under vacuum. The polymer was dissolved in 250 mL chloroform and added 375 mL 4M HCl in dioxane, stirring for 15 minutes. Used rotary evaporation to remove solvents. The crude polymer was purified using dialyis with 15,000 MWCO tubes in 8 L of water for 2 days, using water acidified to pH 3.5 on the second day. Lyophilization of the polymer solution yielded 22 g of Medhesive-027. $^1$H NMR confirmed chemical structure showing a molar ratio of dopamine:PEG600:PCL2k:Lys:PEG1k=1:1.41:0.15:1.61:0.07. UV-vis: 0.81±0.014 µmol dopamine/mg polymer, 12±0.21 wt % dopamine.

Example

Synthesis of Medhesive-030

22.7 g (37.8 mmol) of PEG-diol (600 MW) was azeotropically dried with toluene evaporation and dried in a vacuum dessicator overnight. 200 mL of 20% phosgene solution in toluene (378 mmol) was added to PEG dissolved in 100 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation. The resulting PEG-dCF was dried with a vacuum pump overnight and used without further purification.

To PEG-dCF was added 10.9 g of NHS (94.6 mmol) and 100 mL of chloroform and 11.7 mL of triethylamine (83.2 mmol) in 25 mL of DMF was added dropwise to the PEG solution. And the mixture was stirred at room temperature for 3 hrs. 9.3 g of Lysine (37.8 mmol) was freeze dried with 25.2 mL of 1.5 M tetrabutyl ammonium hydroxide and the resulting Lys-TBA salt in 75 mL DMF was added. The mixture was stirred at room temperature for overnight. 10.4 g of dopamine HCl (54.6 mmol), 17.2 g of HBTU (45.5 mmol), 6.10 g of HOBt (45.4 mmol) and 7.6 mL triethylamine (54.6 mmol) were added. Stirred at room temperature for 2 hrs and the mixture was added to 1.4 L of ethyl ether. The precipitate was collected with vacuum filtration and the polymer was further dialyzed with 3500 MWCO tubes in 7 L of water (acidified to pH 3.5) for 2 days. Lyophilization of the polymer solution yielded 14 g of Medhesive-030. Dopamine modification was repeated to afford 100% coupling of dopamine to the polymer. $^1$H NMR confirmed chemical structure; UV-vis: 1.1±0.037 µmol dopamine/mg polymer, 16±0.57 wt % dopamine; GPC: Mw=13,000, PD=1.8.

Example

Synthesis of Medhesive-038

37.8 g (18.9 mmol) of PEG-diol (2000 MW) was azeotropically dried with toluene evaporation and dried in a vacuum dessicator overnight. 100 mL of 20% phosgene solution in toluene (189 mmol) was added to PEG dissolved in 100 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation. The resulting PEG-dCF was dried with a vacuum pump overnight and used without further purification.

To PEG-dCF was added 5.45 g of NHS (47.3 mmol) and 200 mL of chloroform and 5.85 mL of triethylamine (47.3 mmol) in 80 mL of DMF was added dropwise to the PEG solution. And the mixture was stirred at room temperature for 4 hrs. 2.76 g of Lysine (18.9 mmol) was freeze dried with 18.9 mL of 1M tetrabutyl ammonium hydroxide and the resulting Lys-TBA salt in 40 mL DMF was added. The mixture was stirred at room temperature for overnight. The mixture was added to 800 mL of diethyl ether. The precipitate was collected via vacuum filtration and dried. Dissolved 10 g of the dried precipitate (4.12 mmol) in 44 mL of chloroform and 22 mL of DMF and added to 1.17 g of Dopamine HCl (6.18 mmol), 668 mg of HOBt (4.94 mmol), 1.87 g of HBTU (4.94 mmol), and 1.04 mL of triethylamine (7.42 mmol). Stirred at room temperature for 1 hr and the mixture was added to 400 mL of ethyl ether. The precipitate was collected with vacuum filtration and the polymer was further dialyzed with 15000 MWCO tubes in 3.5 L of water (acidified to pH 3.5) for 2 days. Lyophilization of the polymer solution yielded 14 g of Medhesive-038. Dopamine modification was repeated to afford 100% coupling of dopamine to the polymer. $^1$H NMR confirmed chemical structure; UV-vis: 0.40±0.014 µmmol dopamine/mg polymer, 6.2±0.22 wt % dopamine; GPC: Mw=25,700, PD=1.7.

Example

Synthesis of Medhesive-043

22.7 g (37.8 mmol) of PEG-diol (600 MW) was azeotropically dried with toluene evaporation and dried in a vacuum dessicator overnight. 200 mL of 20% phosgene solution in toluene (378 mmol) was added to PEG dissolved in 100 mL of toluene in a round bottom flask equipped with a condensation flask, an argon inlet, and an outlet to a solution of 20 wt % NaOH in 50% MeOH to trap escaped phosgene. The mixture was stirred in a 55° C. oil bath for three hours with Ar purging, after which the solvent was removed with rotary evaporation. The resulting PEG-dCF was dried with a vacuum pump overnight and used without further purification.

To PEG-dCF was added 10.9 g of NHS (94.6 mmol) and 100 mL of chloroform and 11.7 mL of triethylamine (83.2 mmol) in 25 mL of DMF was added dropwise to the PEG solution. And the mixture was stirred at room temperature for 3 hrs. 5.53 g of Lysine (37.8 mmol) was dissolved in 30 mL DMF and added dropwise and stirred at room temperature for overnight. The mixture was added to 800 mL of diethyl ether. The precipitate was collected via vacuum filtration and dried.

Dissolved the dried precipitate (37.8 mmol) in 150 mL of chloroform and 75 mL of DMF to 5.1 g of HOBt (37.8 mmol), 14.3 g of HBTU (37.8 mmol), 9.31 g of Boc-Lysine (37.8 mmol) and 15.9 mL of triethylamine (113 mmol). The mixture is stirred at room temperature for 1 hour. Added 5.1 g of HOBt (37.8 mmol), 14.3 g of HBTU (37.8 mmol), and 14.3 g of Dopamine HCl (75.4 mmol) and allowed to stir for 1 hour at room temperature. The mixture was added to 1400 mL of diethyl ether. The precipitate was collected via vacuum filtration and dried. Dissolved the dried precipitate in 160 mL of chloroform and 250 mL of 6M HCl Dioxane and stirred for 3 hours at room temperature. The solvent was evaporated under vacuum with NaOH trap. Added 300 mL of toluene and evaporated under vacuum. 400 mL of water is added and vacuum filtered the precipitate. The crude product was further purified through dialysis (3500 MWCO) in deionized $H_2O$ for 4 hours, deionized water (acidified to pH 3.5) for 40 hrs and deionized water for 4 more hours. After lyophilization, 14.0 g of Medhesive-068 was obtained. $^1$H NMR confirmed chemical structure; UV-vis: 0.756±0.068 μmmol dopamine/mg polymer, 12±1.0 wt % dopamine.

Example

Coating of Adhesive Film onto Collagen Backing

Collagen sheets were rehydrated in water and cut into 8-inch strips and further rinsed with 0.1% solution of sodium dodecyl sulfate (SDS) for 20 minutes. Collagen sheets were then rinsed with water and placed in phosphate buffered saline (PBS) until use. The hydrated collagen sheets were further cut into circles (diameter ~8.8 cm) and placed in a petri dish. Adhesive polymer in 5 mL of methanol or chloroform were added to the collagen and the solvent was allow to slowly evaporate at different temperatures (room temperature, 37, and 50° C.) while agitating the petri dish gently. The adhesive-coated collagen was further dried in vacuum desiccator for at least 12 hours.

Example

Adhesion Tests Performed on Adhesive-Coated Collagen Sheets

Figure 14:
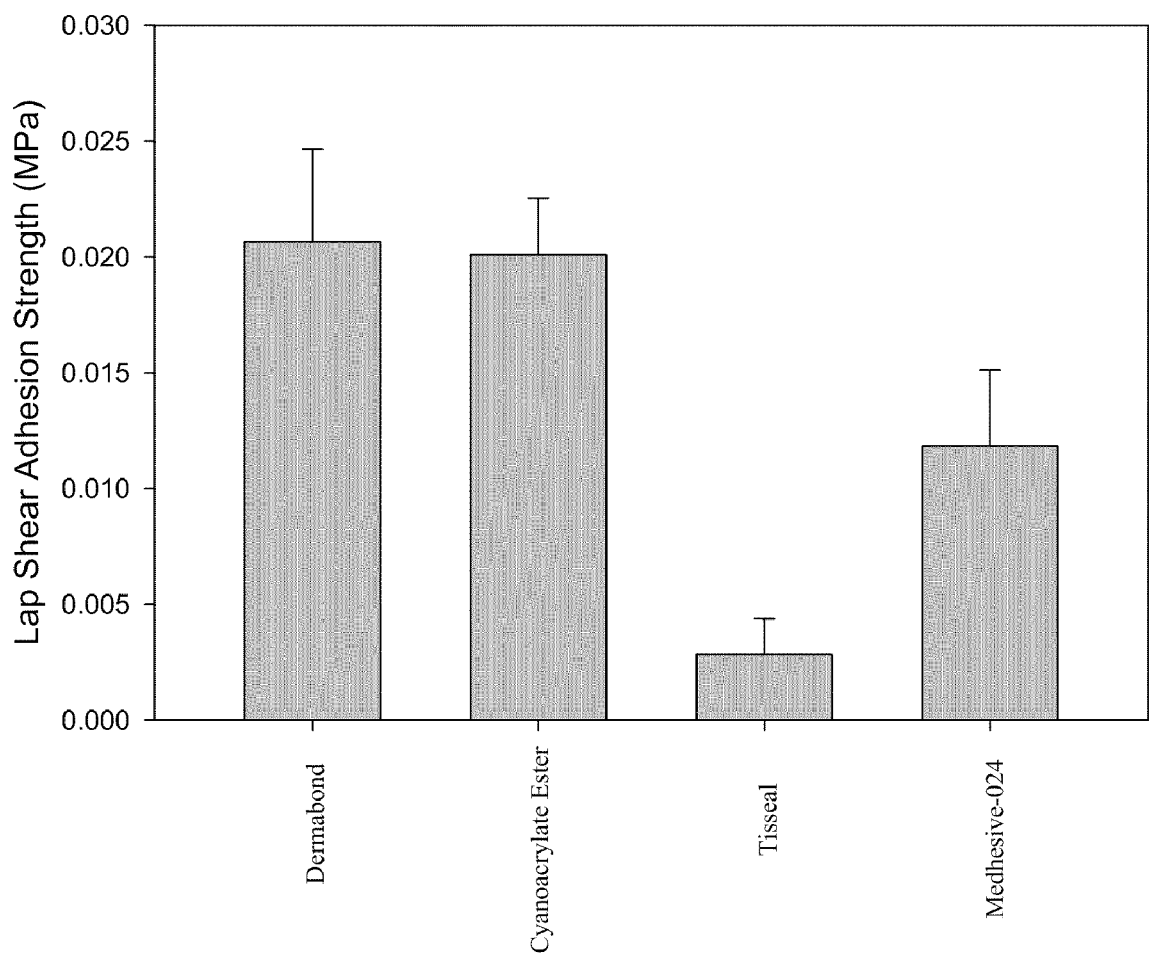
FIG. 14 provides lap shear adhesion tests performed on bioadhesive constructs of the invention.
Figure 15:
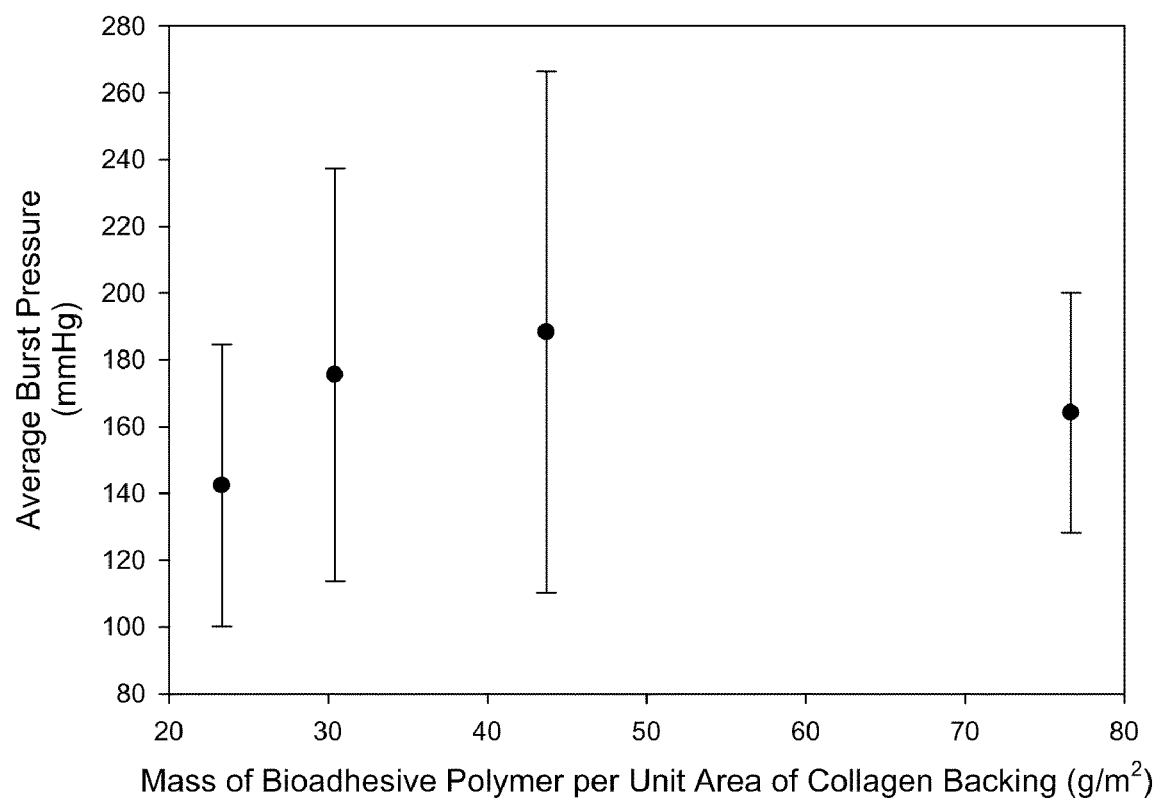
FIG. 15 provides burst strengths for a bioadhesive construct of the invention.

The bioadhesive-coated collagen sheet is rehydrated for 1 hr with PBS. 31.7 uL of a 20 mg/mL $NaIO_4$ was added to the collagen substrate followed be the bioadhesive-coated collagen sheet. A glass plate is placed over the adhesive joint, which is further weighted down with a 100 gram weight for 1 hr. Another 31.7 uL of 20 mg/mL $NaIO_4$ was applied to the top of the collagen backing and the adhesive joint was allow to cure for additional 1 hr. After soaking in PBS buffer for 1 hr, both lap shear (ASTM F2255) and burst strength (ASTM F2392) adhesion tests (FIG. 8) were performed following procedures from ASTM standards. FIG. 14 shows the lap shear adhesion strength that is needed to separate bioadhesive-coated collagen backing adhered to collagen substrate. Medhesive-024 demonstrated adhesive strength that is significantly higher then Tisseel but lower than that of cyanoacrylate-based adhesives. FIG. 15 shows the amount of pressure that is required to burst through a joint sealed with adhesive-coated collagen backing Medhesive-024 demonstrated maximum burst strength of 190±78 mmHg.

Example

Coating QuadraSeal-DH (QS-DH) (FIG. 13d) Adhesive on Marlex Surgical Mesh

Figure 16:
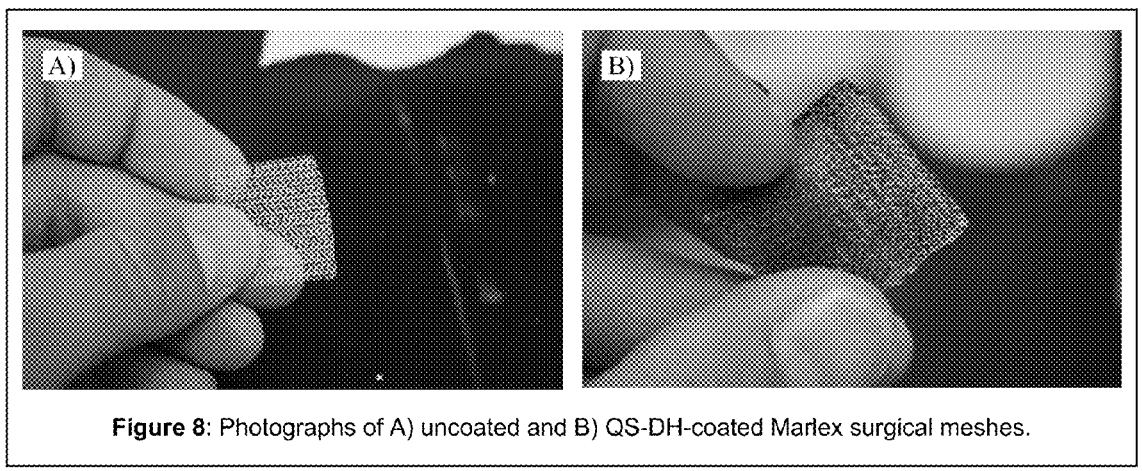
FIG. 16 depicts a surgical mesh coated with a bioadhesive coating described in the specification.

Marlex surgical mesh was cleaned with sonication in 2-propanol and treated with $O_2$ plasma. 15 wt % of QS-DH adhesive (cured with $NaIO_4$) was applied onto the mesh through an applicator. Photographs of both uncoated and adhesive-coated Marlex surgical mesh (FIG. 16) demonstrate the feasibility of using our adhesive materials to encapsulate synthetic materials used in soft tissue reconstruction.

Example

In Vitro Degradation

Figure 4:
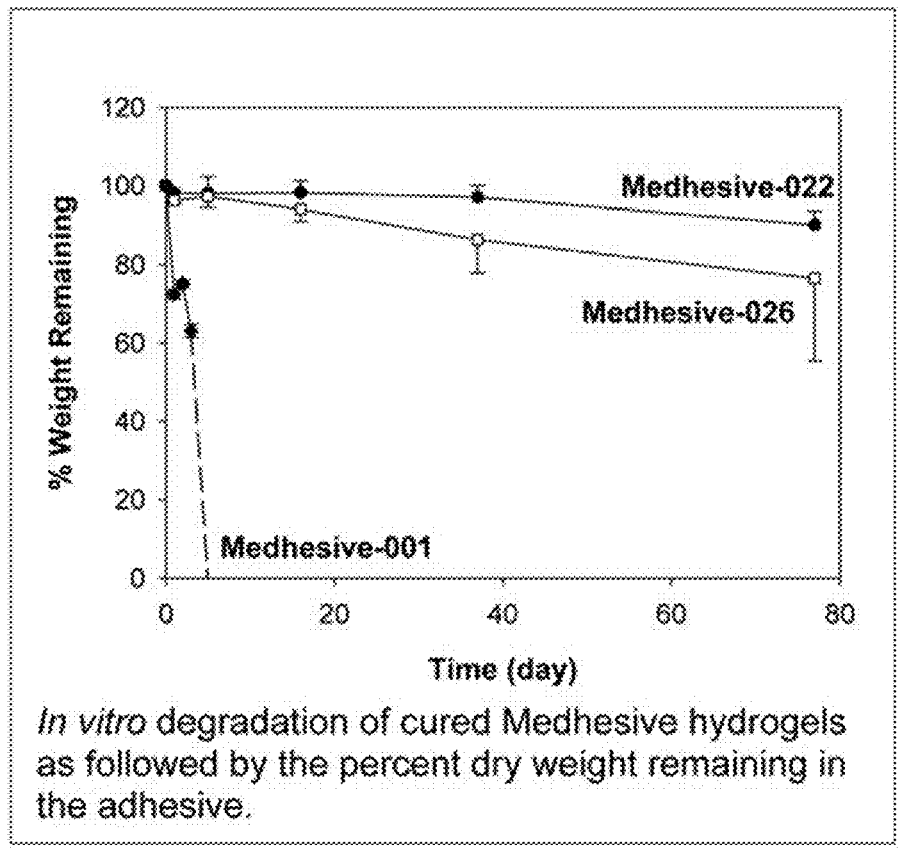
FIG. 4 provides degradation information regarding several of the bioadhesives of the invention.

The primary degradation pathway of Medhesive is through hydrolysis. In vitro degradation of Medhesive was performed by incubating the cured Medhesive hydrogels in PBS (pH 7.4) at 37° C. and their percent dry weight loss was followed over time. As shown in FIG. 4, Medhesive-001 also referred to as PEES, which contains ester linkages throughout its polymer backbone, lost nearly 30 wt % of its dry mass after just one day of incubation and was completely degraded within five days. On the other hand, urethane-based Medhesives such as Medhesive-022 (also PEU-1) and Medhesive-026 (also PEU-3) lost only 10 and 23 wt % of their dry mass, respectively, after 77 days of incubation. By further engineering the polymer backbone of Medhesive polymers, we expect to generate polymers that will degrade predictably over a span of weeks or months.

Example

Adhesion Tests of Adhesive Performed on Collagen Substrate

Medhesive polymers were adhere to collagen substrates and compared their performance to a leading commercially available fibrin-based sealant (Tisseel V H, Baxter International, Inc.), a topical cyanoacrylate-based adhesive (Dermabond, Ethicon, Inc.), and QuadraSeal-DH (FIG. 13d), a PEG-based sealant Nerites developed. Following procedures outlined in American Society for Testing and Materials (ASTM), we performed lap shear (ASTM F2255) and burst strength (ASTM F2392) adhesion tests using rehydrated collagen sheets (Nippi, Inc.) as the test substrate. All tests were performed within one hour of mixing with cross-linking reagent ($NaIO_4$) at a final polymer concentration of 15 wt %. As shown in FIG. 7, Medhesive demonstrated more than seven times the adhesion strength as compared to that of Tisseel. Only Dermabond demonstrated stronger adhesive strength compared to Medhesive. However, cyanoacrylate-based adhesives, like Dermabond, are approved only for topical usage due to cytotoxicity issues and poor mechanical compatibility with soft tissues.[83] On the other hand, preliminary biocompatibility tests and histological data performed on Nerites' adhesives revealed that they are relatively benign. Medhesive generally exhibited cohesive failure, indicating these adhesive formulations form relatively strong interfacial bonds with wetted collagen substrates while exhibiting relatively weak bulk mechanical properties. These hydrogel-based adhesives have very high water content (75-95 wt % water when fully swollen), which likely contributes to the observed cohesive failure. Further engineering may be needed to increase the mechanical properties of these adhesives to improve their bulk cohesive properties.

Patterned Adhesive Coating of Mesh for Accelerated Mesh-Tissue Integration

Figure 17:
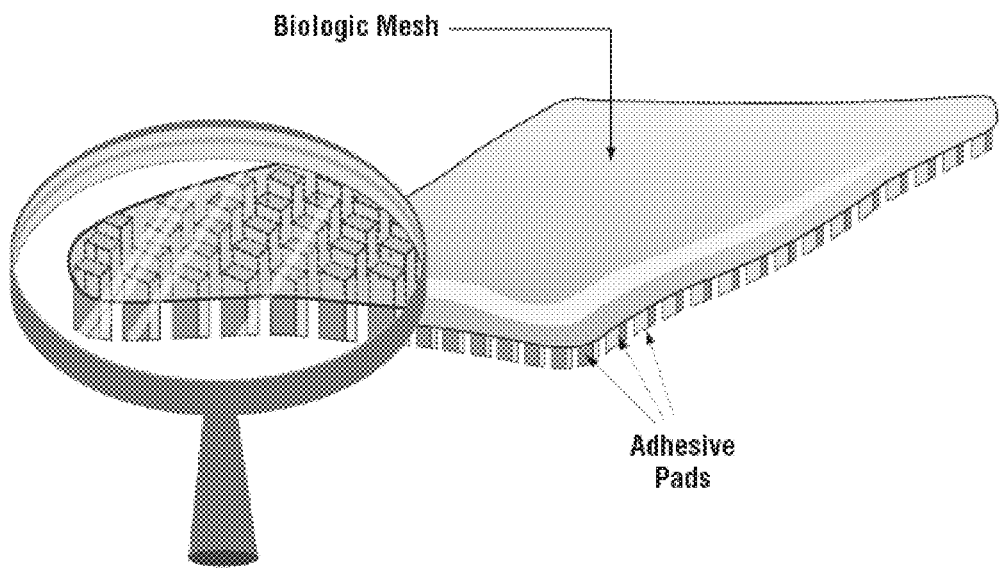
FIG. 17 provides a mesh coated with adhesive pads.
Figure 18:
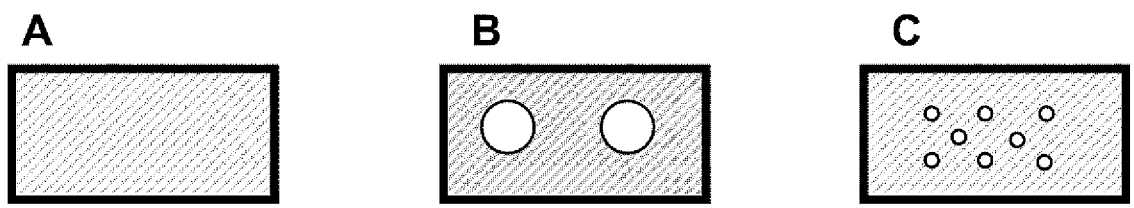
FIG. 18 provides schematics of A) construct with 100% area coverage, B) a patterned construct with 2 circular uncoated areas with larger diameter, and C), a patterned construct with 8 circular uncoated areas with smaller diameter.

The adhesive polymer can be coated on the mesh in a pattern to promote faster integration of the host tissue and mesh. Unlike other fixation methods, adhesives may act as a barrier for tissue ingrowth into the mesh if their degradation rate is slower than the cell invasion rate and subsequent graft incorporation. Meshes secured with a slow degrading adhesive such as cyanoacrylate demonstrated impaired tissue integration. For meshes secured with conventional methods, the tensile strength of the mesh-tissue interface reached a maximum within four weeks after implantation, indicating that the meshes were fully integrated with the host tissue. This suggests that cellular infiltration occurs earlier. While the adhesive polymers of the invention exhibit a variety of degradation profiles, some formulations may take several months to be completely absorbed. To ensure rapid tissue integration into the mesh while maintaining strong adhesion at the time of implantation, adhesives can be coated onto a mesh in an array of adhesive pads, leaving other areas of the mesh uncoated as shown in FIG. 17. Other patterns with various geometric shapes (circular, rectangular, etc.) can also be created FIG. 18. The regions coated with adhesive will provide the initial bonding strength necessary to secure the mesh in place, while the uncoated regions will provide an unobstructed path for cellular invasion and tissue ingrowth to immediately occur.

To create a patterned adhesive polymer coating, a solvent casting method could be used, in which a metallic lattice will be placed over the mesh while the polymer solution is drying. The lattice will be used to displace the polymer solution so that an uncoated region is formed as the solution dries. By controlling the dimensions (5-10 mm) and the thickness (0.2-1.0 mm) of the lattice, it is possible to vary the ratio of the surface areas of the coated and uncoated regions. Bovine pericardium will be used both as the surrogate backing and test substrate. Lap shear adhesion testing will be performed to determine the effect of the patterned coating on the adhesive properties of the bioadhesive construct. For each coating pattern, a minimum of 10 repetitions will be tested, and statistical analysis will be performed using ANOVA, the Tukey post hoc analysis, and a significance level of $p=0.05$.

It is expected that a patterned adhesive can be easily achieved using the described method. The adhesive strength of the patterned coating will likely be slightly lower compared to the non-patterned adhesive coating since the overall surface area of the adhesive is decreased. By varying the ratio of the surface areas between the coated and uncoated regions, the surface can be tailored adjust for the initial adhesive strength to the rate of tissue ingrowth. A pattern that results in greater than 80% of the adhesive strength of the non-patterned coating will be selected for subsequent animal studies. The rate of tissue ingrowth will be determined by implanting both patterned and non-patterned bioadhesive constructs into a rabbit model.

Waite, J. H., *Nature's underwater adhesive specialist*. Int. J. Adhes. Adhes., 1987. 7(1): p. 9-14.

2. Yamamoto, H., *Marine adhesive proteins and some biotechnological applications*. Biotechnology and Genetic Engineering Reviews, 1996. 13: p. 133-65.

3. Yu, M., J. Hwang, and T. J. Deming, *Role of L-3,4-dihydroxyphenylanine in mussel adhesive proteins*. Journal of American Chemical Society, 1999. 121(24): p. 5825-5826.

4. Deming, T. J., M. Yu, and J. Hwang, *Mechanical studies of adhesion and crosslinking in marine adhesive protein analogs*. Polymeric Materials: Science and Engineering, 1999. 80: p. 471-472.

5. Waite, J. H., *Mussel beards: A coming of Age*. Chemistry and Industry, 1991. 2 September: p. 607-611.

6. Waite, J. H. and S. O. Andersen, *3,4-Dihydroxyphenylalanine in an insoluble shell protein of Mytilus edulis*. Biochimica et Biophysica Acta, 1978. 541(1): p. 107-14.

7. Pardo, J., et al., *Purification of adhesive proteins from mussels*. Protein Expr Purif, 1990. 1(2): p. 147-50.

8. Papov, V. V., et al., *Hydroxyarginine-containing polyphenolic proteins in the adhesive plaques of the marine mussel Mytilus edulis*. Journal of Biological Chemistry, 1995. 270 (34): p. 20183-92.

9. Maugh, K. J., et al., *Recombinant bioadhesive proteins of marine animals and their use in adhesive compositions*, in *Genex Corp.* 1988: USA. p. 124.

10. Strausberg, R. L., et al., *Development of a microbial system for production of mussel adhesive protein*, in *Adhesives from Renewable Resources*. 1989. p. 453-464.

11. Filpula, D. R., et al., *Structural and functional repetition in a marine mussel adhesive protein*. Biotechnol. Prog., 1990. 6(3): p. 171-7.

12. Yu, M. and T. J. Deming, *Synthetic polypeptide mimics of marine adhesives*. Macromolecules, 1998. 31(15): p. 4739-45.

13. Yamamoto, H., *Adhesive studies of synthetic polypeptides: a model for marine adhesive proteins*. J. Adhes. Sci. Technol., 1987. 1(2): p. 177-83.

14. Yamamoto, H., et al., *Insolubilizing and adhesive studies of water-soluble synthetic model proteins*. Int. J. Biol. Macromol., 1990. 12(5): p. 305-10.

15. Tatehata, H., et al., *Model polypeptide of mussel adhesive protein. I. Synthesis and adhesive studies of sequential polypeptides (X-Tyr-Lys)n and (Y-Lys)n*. Journal of Applied Polymer Science, 2000. 76(6): p. 929-937.

16. Strausberg, R. L. and R. P. Link, *Protein-based medical adhesives*. Trends in Biotechnology, 1990. 8(2): p. 53-7.

17. Young, G. A. and D. J. Crisp, *Marine Animals and Adhesion*, in *Adhesion 6*. Barking, K. W. Allen, Editor. 1982, Applied Science Publishers, Ltd.: England.

18. Ninan, L., et al., *Adhesive strength of marine mussel extracts on porcine skin*. Biomaterials, 2003. 24(22): p. 4091-9.

19. Schnurrer, J. and C.-M. Lehr, *Mucoadhesive properties of the mussel adhesive protein*. International Journal of Pharmaceutics, 1996. 141(1,2): p. 251-256.

20. Lee, B. P., et al., *Synthesis of 3,4-Dihydroxyphenylalanine (DOPA) Containing Monomers and Their Copolymerization with PEG-Diacrylate to from Hydrogels*. Journal of Biomaterials Science, Polymer Edition, 2004. 15: p. 449-464.

21. Lee, B. P., J. L. Dalsin, and P. B. Messersmith, *Synthesis and Gelation of DOPA-Modified Poly(ethylene glycol) Hydrogels*. Biomacromolecules, 2002. 3(5): p. 1038-47.

22. Lee, B. P., et al., *Rapid Photocurable of Amphiphilic Block Copolymers Hydrogels with High DOPA Contents*. Maclomolecules, 2006. 39: p. 1740-48.

23. Huang, K., et al., *Synthesis and Characterization of Self-Assembling Block Copolymers Containing Bioadhesive End Groups*. Biomacromolecules, 2002. 3(2): p. 397-406.

24. Dalsin, J. L., et al., *Mussel Adhesive Protein Mimetic Polymers for the Preparation of Nonfouling Surfaces*. Journal of American Chemical Society, 2003. 125: p. 4253-4258.

25. Dalsin, J. L., L. Lin, and P. B. Messersmith, *Antifouling performance of poly(ethylene glycol) anchored onto surfaces by mussel adhesive protein mimetic peptides*. Polymeric Materials Science and Engineering, 2004. 90: p. 247-248.
26. Dalsin, J. L., et al., *Protein Resistance of Titanium Oxide Surfaces Modified by Biologically Inspired mPEG-DOPA*. Langmuir, 2005. 21(2): p. 640-646.
27. Statz, A. R., et al., *New Peptidomimetic Polymers for Antifouling Surfaces*. Journal of the American Chemical Society, 2005. 127(22): p. 7972-7973.
28. Fan, X., L. Lin, and P. B. Messersmith, *Surface-initiated polymerization from TiO₂nanoparticle surfaces through a biomimetic initiator: A new route toward polymer-matrix nanocomposites*. Composites Science and Technology, 2006. 66: p. 1195-1201.
29. Dossot, M., et al., *Role of phenolic derivatives in photopolymerization of an acrylate coating*. Journal of Applied Polymer Science, 2000. 78(12): p. 2061-2074.
30. Khudyakov, I. V., et al., *Kinetics of Photopolymerization of Acrylates with Functionality of 1-6*. Ind. Eng. Chem. Res., 1999. 38: p. 3353-3359.
31. Sichel, G., et al., *Relationship between melanin content and superoxide dismutase (SOD) activity in the liver of various species of animals*. Cell Biochem. Funct, 1987. 5(2): p. 123-8.
32. Waite, J. H. and X. Qin, *Polyphosphoprotein from the Adhesive Pads of Mytilus edulis*. Biochemistry, 2001. 40(9): p. 2887-93.
33. Long, J. R., et al., *A peptide that inhibits hydroxyapatite growth is in an extended conformation on the crystal surface*. Proceedings of the National Academy of Sciences of the United States of America, 1998. 95(21): p. 12083-12087.
34. Meisel, H. and C. Olieman, *Estimation of calcium-binding constants of casein phosphopeptides by capillary zone electrophoresis*. Anal. Chim. Acta, 1998. 372(1-2): p. 291-297.
35. Lu, G., D. Wu, and R. Fu, *Studies on the synthesis and antibacterial activities of polymeric quaternary ammonium salts from dimethylaminoethyl methacrylate*. Reactive & Functional Polymers, 2007. 67(4): p. 355-366.
36. Li, Z., et al., *Two-Level Antibacterial Coating with Both Release-Killing and Contact-Killing Capabilities*. Langmuir 2006. 22(24): p. 9820-9823.
37. Sun, Q., et al., *Improved antifouling property of zwitterionic ultrafiltration membrane composed of acrylonitrile and sulfobetaine copolymer*. Journal of Membrane Science, 2006. 285(1+2): p. 299-305.
38. Kitano, H., et al., *Resistance of zwitterionic telomers accumulated on metal surfaces against nonspecific adsorption of proteins*. Journal of Colloid and Interface Science, 2005. 282(2): p. 340-348.
39. Hajjaji, N., et al., *Effect of N-alkylbetaines on the corrosion of iron in 1 M hydrochloric acid solution*. Corrosion, 1993. 49(4): p. 326-34.
40. Morgan, D. M. L., V. L. Larvin, and J. D. Pearson, *Biochemical characterization of polycation-induced cytotoxicity to human vascular endothelial cells*. Journal of Cell Science, 1989. 94(3): p. 553-9.
41. Fischer, D., et al., *In vitro cytotoxicity testing of polycations: influence of polymer structure on cell viability and hemolysis*. Biomaterials 2003. 24(7): p. 1121-1131.
42. Zekorn, T. D., et al., *Biocompatibility and immunology in the encapsulation of islets of Langerhans (bioartificial pancreas)*. Int J Artif Organs, 1996. 19(4): p. 251-7.
43. Ishihara, M., et al., *Photocrosslinkable chitosan as a dressing for wound occlusion and accelerator in healing process*. Biomaterials, 2002. 23(3): p. 833-40.
44. Huin-Amargier, C., et al., *New physically and chemically crosslinked hyaluronate (HA)-based hydrogels for cartilage repair*. Journal of Biomedical Materials Research, Part A, 2006. 76A(2): p. 416-424.
45. Stevens, P. V., Food Australia, 1992. 44(7): p. 320-324.
46. Ikada, Y., *Tissue adhesives*, in *Wound Closure Biomaterials and Devices*, C. C. Chu, J. A. von Fraunhofer, and H. P. Greisler, Editors. 1997, CRC Press, Inc.: Boca Raton, Fla. p. 317-346.
47. Sierra, D. and R. Saltz, *Surgical Adhesives and Sealants: Current Technology and Applications*. 1996, Lancaster, Pa.: Technomic Publishing Company, Inc.
48. Donkerwolcke, M., F. Burny, and D. Muster, *Tissues and bone adhesives-historical aspects*. Biomaterials 1998. 19 p. 1461-1466.
49. Rzepecki, L. M., K. M. Hansen, and J. H. Waite, *Bioadhesives: dopa and phenolic proteins as component of organic composite materials*, in *Principles of Cell Adhesion*. 1995, CRC Press. p. 107-142.
50. Spotnitz, W. D., *History of tissue adhesive*, in *Surgical Adhesives and Sealants: Current Technology and Applications*, D. H. Sierra and R. Saltz, Editors. 1996, Technomic Publishing Co. Inc.: Lancaster, Pa. p. 3-11.
51. ASTM-F2392, *Standard Test Method for Burst Strength of Surgical Sealants* 2004.
52. Lee, B. P., J. L. Dalsin, and P. B. Messersmith, *Synthetic Polymer Mimics Of Mussel Adhesive Proteins for Medical Applications*, in *Biological Adheisves*, A. M. Smith and J. A. Callow, Editors. 2006, Springer-Verlag. p. 257-278.
53. Benedek, I., *End-Uses of Pressure Sensitive Products*, in *Developments In Pressure-Sensitive Products*, I. Benedek, Editor. 2006, CRC Press: Boca Raton, Fla. p. 539-596.
54. Creton, C., *Pressure-sensitive adhesives: an introductory course*. MRS Bulletin, 2003. 28(6): p. 434-439.
55. Lucast, D. H., *Adhesive considerations for developing stick-to-skin products*. Adhesives Age 2000. 43(10): p. 38-39.
56. Venkatraman, S, and R. Gale, *Skin adhesives and skin adhesion. 1. Transdermal drug delivery systems*. Biomaterials, 1998. 19(13): p. 1119-36.
57. Feldstein, M. M., N. A. Plate, and G. W. Cleary, *Molecular design of hydrophilic pressure-sensitive adhesives for medical applications*, in *Developments In Pressure-Sensitive Products*, I. Benedek, Editor. 2006, CRC Press: Boca Raton, Fla. p. 473-503.
58. Skelhorne, G. and H. Munro, *Hydrogel Adhesive for Wound-Care Applications*. Medical Device Technology, 2002: p. 19-23.
59. Chalykh, A. A., et al., *Pressure-Sensitive Adhesion in the Blends of Poly(N-Vinyl Pyrrolidone) and Poly(Ethylene Glycol) of Disparate Chain Lengths*. The Journal of Adhesion, 2002 78(8): p. 667-694.
60. Ruibal, R. and V. Ernst, *The structure of the digital setae of lizards*. J. Morphology, 1965. 117: p. 271-293.
61. Geim, A. K., et al., *Microfabricated adhesive mimicking gecko foot-hair*. Nat. Materials, 2003. 2: p. 461-463.
62. Northen, M. T. and K. L. Turner, *A batch fabricated biomimetic dry adhesive*. Nanotechnology 2005. 16: p. 1159-1166.
63. Sitti, M. and R. Fearing, *Synthetic gecko foot-hair micro/nano-structures as dry adhesives*. J. Adhes. Sci. Technol., 2003. 17: p. 1055-1073.

64. Yurdumakan, B., et al., *Synthetic gecko foot-hairs from multiwalled carbon nanotubes.* Chem. Commun., 2005. 30: p. 3799-3801.
65. Peressadko, A. and S. N. Gorb, *When less is more: Experimental evidence for tenacity enhancement by division of contact area.* J. Adhesion, 2004. 80: p. 1-5.
66. Crosby, A. J., M. Hageman, and A. Duncan, *Controlling polymer adhesion with "Pancakes".* Langmuir 2005. 21: p. 11738-11743.
67. Northen, M. T. and K. L. Turner, *Meso-scale adhesion testing of integrated micro-and nano-scale structures.* Sensors and Actuators A, 2006. 130-131: p. 583-587.
68. Huber, G., et al., *Evidence for capillary contributions to gecko adhesion from single spatula nanomechanical measurements.* Proc. Nat. Acad. Sci. USA, 2005. 102: p. 16293-16296.
69. Sun, W., et al., *The nature of the gecko lizard adhesive force.* Biophys. J., 2005. 89: p. L14-16.
70. Wisniewski, N. and M. Reichert, *Methods for reducing biosensor membrane biofouling.* Colloids Surf B Biointerfaces, 2000 18(3-4): p. 197-219.
71. Gu, J. D., et al., *The role of microbial biofilms in deterioration of space station candidate materials.* Int. Biodeterior Biodegradaton, 1998. 41(1): p. 25-33.
72. Harris, J. M., *Introduction to biotechnical and biomedical applications of poly(ethylene glycol),* in *Poly(ethylene glycol) chemistry: biotechnical and biomedical applications,* J. M. Harris, Editor. 1992, Plenum Press: New York. p. 1-14.
73. Ryu, D. Y., et al., *A Generalized Approach to the Modification of Solid Surfaces* Science 2005. 308(5719): p. 236-239.
74. Ratner, B. D., *Titanium in Medicine: Material Science, Surface Science, Engineering, Biological Responses and Medical Applications,* ed. D. M. Brunette, et al. 2000, Heidelberg: Springer-Verlag.
75. Leonard, E. F., V. T. Turitto, and L. Vroman, *Blood in contact with natural and artificial surfaces.* New York Academy of Sciences, 1987. 516: p. 688.
76. Mukkamala, R., A. M. Kushner, and C. R. Bertozzi, *Hydrogel polymers from alkylthio acrylates for biomedical applications.* Polymer Gels: Fundamentals and Applications, 2003. 833: p. 163-174.
77. Bruinsma, G. M., H. C. van der Mei, and H. J. Busscher, *Bacterial adhesion to surface hydrophilic and hydrophobic contact lenses.* Biomaterials 2001. 22(24): p. 3217-3224.
78. Zawada, J., *A-dec, Inc.* 2005.
79. Kingshott, P., H. Thissen, and H. J. Griesser, *Effects of cloud-point grafting, chain length, and density of PEG layers on competitive adsorption of ocular proteins.* Biomaterials, 2002. 23(9): p. 2043-2056.

List of PEG-Based Monomers Used in this Patent Application

| Monomer | Abbreviation | $R_{10}$ | $R_{12}$ |
|---|---|---|---|
| Poly(ethylene glycol) methyl ether methacrylate (Mn~300) | EG4ME | (structure with $(O-CH_2CH_2)_4$) | —$CH_3$ |
| Poly(ethylene glycol) methyl ether methacrylate (Mn~475) | EG9ME | (structure with $(O-CH_2CH_2)_9$) | —$CH_3$ |
| Poly(ethylene glycol) methyl ether acrylamide (Mn~680) | EG12AA | (structure with $(O-CH_2CH_2)_{12}$) | —H |
| Poly(ethylene glycol) methyl ether methacrylamide (Mn~1085) | EG22MA | (structure with $(O-CH_2CH_2)_{22}$) | —$CH_3$ |

| Monomer | Abbreviation | $R_{10}$ | $R_{12}$ |
|---|---|---|---|
| Acrylamide | AAm | (structure with $NH_2$) | —H |

-continued

| Monomer | Abbreviation | R₁₀ | R₁₂ |
|---|---|---|---|
| N-Acryloylmorpholine | NAM | (morpholine acrylamide structure) | —H |
| 2-Hydroxyethyl methacrylate | HEMA | (2-hydroxyethyl ester structure) | —CH₃ |
| N-Isopropylacrylamide | NIPAM | (isopropyl acrylamide structure) | —H |
| 2-Methoxyethyl acrylate | MEA | (2-methoxyethyl ester structure) | —H |
| [3-(Methacryloylamino)propyl]dimethyl(3-sulfopropyl)ammonium hydroxide | SBMA | (sulfobetaine structure) | —CH₃ |
| 1-Vinyl-2-pyrrolidone | VP | (pyrrolidone structure) | —H |

List of Basic Monomers Used in this Patent Application

| Monomer | Abbreviation | R₁₀ | R₁₂ |
|---|---|---|---|
| (3-Acrylamidopropyl)trimethylammonium | APTA | (trimethylammonium propyl acrylamide structure) | —H |
| Allylamine | AA | (CH₂-NH₂ allyl structure) | —H |
| 1,4-Diaminobutane methacrylamide | DABMA | (diaminobutane methacrylamide structure) | —CH₃ |

List of Acidic Monomers Used in this Patent Application

| Monomer | Abbreviation | R₁₀ | R₁₂ |
|---|---|---|---|
| 2-Acrylamido-2-methyl-1-propanesulfonic acid | AMPS | (sulfonic acid acrylamide structure) | —H |

| Monomer | Abbreviation | $R_{10}$ | $R_{12}$ |
|---|---|---|---|
| Ethylene glycol methacrylate phosphate | EGMP | 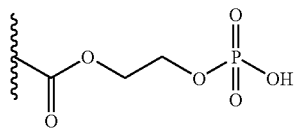 | —$CH_3$ |

Hydrophobic Monomer Used in this Patent Application

| Monomer | Abbreviation | $R_{10}$ | $R_{12}$ |
|---|---|---|---|
| 2,2,2-Trifluoroethyl methacrylate | TFEM | 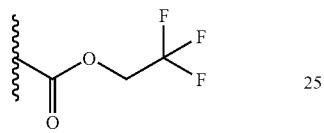 | —$CH_3$ |

List of PEG-Based Polymers Prepared from AIBN-Initiated Polymerization

| Polymer | Reaction Solvent | Monomer Feed Molar Ratio | Monomer:AIBN Feed Molar Ratio | Reaction Time (Hrs) | $M_w$ | PD | DMA wt % |
|---|---|---|---|---|---|---|---|
| PDMA-1 | DMF | 1:1 DMA1:EG9ME | 50:1 | 5 | 430,000 | 1.8 | 24 |
| PDMA-2 | DMF | 1:9 DMA1:EG9ME | 98:1 | 18 | >$10^6$ | — | 4.1 |
| PDMA-3 | DMF | 1:1 DMA1:EG4ME | 50:1 | 17 | 790,000 | 4.1 | 32 |
| PDMA-4 | DMF | 1:3 DMA1:EG12AA | 50:1 | 16 | 9,500 | 1.7 | 12 |
| PDMA-5 | DMF | 1:1 DMA3:EG9ME | 40:1 | 18 | — | — | 26 |

List of Water Soluble Polymers Prepared from AIBN-Initiated Polymerization

| Polymer | Reaction Solvent | Monomer Feed Molar Ratio | Monomer:AIBN Feed Molar Ratio | Reaction Time (Hrs) | $M_w$ | PD | DMA wt % |
|---|---|---|---|---|---|---|---|
| PDMA-6 | 0.5M NaCl | 1:8 DMA1:SBMA | 77:1 | 18 | 220,000 | 1.2 | 8.6 |
| PDMA-7 | DMF | 1:20 DMA1:NAM | 250:1 | 16 | 250,000 | 3.5 | 4.5 |
| PDMA-8 | DMF | 1:20 DMA2:NAM | 250:1 | 16 | — | — | 8.5 |
| PDMA-9 | DMF | 1:10 DMA1:Am | 250:1 | 16 | — | — | 18 |
| PDMA-10 | Water/ Methanol | 1:10 DMA1:Am | 250:1 | 16 | — | — | 23 |

List of Water Insoluble, Hydrophilic Polymers Prepared from AIBN-Initiated Polymerization

| Polymer | Reaction Solvent | Monomer Feed Molar Ratio | Monomer:AIBN Feed Molar Ratio | Reaction Time (Hrs) | $M_w$ | PD | DMA wt % |
|---|---|---|---|---|---|---|---|
| PDMA-11 | DMF | 1:3 DMA1:HEMA | 100:1 | 18 | — | — | 27 |
| PDMA-12 | DMF | 1:8 DMA1:MEA | 100:1 | 18 | 250,000 | 1.7 | 21 |

Hydrophobic Polymer Prepared from AIBN-Initiated Polymerization

| Polymer | Reaction Solvent | Monomer Feed Molar Ratio | Monomer:AIBN Feed Molar Ratio | Reaction Time (Hrs) | $M_w$ | PD | DMA wt % |
|---|---|---|---|---|---|---|---|
| DMA-13 | DMF | 1:25 DMA1:TFME | 105:1 | 17 | — | — | 2.8 |

List of 3-Component Polymers Prepared from AIBN-Initiated Polymerization

| Polymer | Reaction Solvent | Monomer Feed Molar Ratio | Monomer:AIBN Feed Molar Ratio | Reaction Time (Hrs) | $M_w$ | PD | DMA wt % |
|---|---|---|---|---|---|---|---|
| PDMA-14 | DMF | 1:1:1 DMA1:DABMA:EG9ME | 75:1 | 17 | 108 | 1.2 | 13 |
| PDMA-15 | DMF | 1:2:4 DMA:AA:EG9ME | 70:1 | 4 | 132,000 (67 wt %) 61,000 (33 wt %)* | 1.2 1.3 | 7.0 |
| PDMA-16 | DMF | 1:1:1 DMA1:APTA:EG9ME | 75:1 | 16 | 78,000 | 1.0 | 18 |
| PDMA-17 | DMF | 1:1:25 DMA1:APTA:NAM | 84:1 | 16 | — | — | 6.8 |
| PDMA-18 | DMF | 2:1:4 DMA1:AMPS:EG4ME | 35:1 | 4 | 82,000 | 1.9 | 14 |
| PDMA-19 | DMF | 1:1:1 DMA1:AMPS:EG9ME | 75:1 | 16 | 97,000 | 2.0 | 17 |
| PDMA-20 | Water/ Methanol | 2:1:20 DMA1:AMPS:Am | 245:1 | 3 | — | — | 19 |
| PDMA-21 | DMF | 1:1:8 DMA1:EGMP:EG9ME | 67:1 | 16 | 81,000 | 1.2 | 3.9 |

*Bimodal molecular weight distribution

List of Polymers Prepared Using CA as the Chain Transfer Agent

| Polymer | Reaction Solvent | Monomer Feed Molar Ratio | Monomer:AIBN Feed Molar Ratio | Reaction Time (Hrs) | $M_w$ | PD | DMA wt % |
|---|---|---|---|---|---|---|---|
| PDMA-22 | DMF | 1:20 DMA1:NIPAM | 125:2:1 Monomer:CA:AIBN | 18 | 81,000 | 1.1 | 11 |
| PDMA-23 | DMF | 1:3 DMA1:NAM | 95:12:1 Monomer:CA:AIBN | 18 | 5,700 | 2.1 | 31 |
| PDMA-24 | DMF | 1:1 DMA1:EG22MA | 27:1.3:1 Monomer:CA:AIBN | 18 | 106,000 (58 wt %) 7,600 (42 wt %)* | 1.7 1.6 | 5.0 |

*Bimodal molecular weight distribution

Hydrophilic Prepolymers Used in Chain Extension Reaction

| Prepolymer | Abbreviation | Chemical Structure In Poly(Ether Urethane)/Poly(Ether Ester) | In Poly(Ether Ester) |
|---|---|---|---|
| Polyethylene glycol 600 MW | EG600 | (structure with n=13) | (structure with n=13) |
| Polyethylene glycol 1000 MW | EG1k | (structure with n=22) | (structure with n=22) |
| Polyethylene glycol 8000 MW | EG8k | (structure with n=181) | (structure with n=181) |
| Branched, 4-Armed Polyethylene glycol | EG10kb | — | (4-armed structure with n=56) |

Hydrophobic Prepolymers Used in Chain Extension Reaction

| Prepolymer | Abbreviation | Chemical Structure |
|---|---|---|
| Polycaprolactone 2000 MW | CL2k | (structure) |
| Polycaprolactone Bis-Glycine 1000 MW | CL1kG | (structure) |
| Polycaprolactone Bis-Glycine 2000 MW | CL2kG | (structure) |

Amphiphilic Prepolymers Used in Chain Extension Reaction

| Prepolymer | Abbreviation | Chemical Structure |
|---|---|---|
| PEG-PPG-PEG 1900 MW | F2k | –(O–CH$_2$CH$_2$)$_{10}$–(O–CH(CH$_3$)CH$_2$)$_{16}$–(O–CH$_2$CH$_2$)$_{10}$–O– |
| PEG-PPG-PEG 8350 MW | F68 | –(O–CH$_2$CH$_2$)$_{77}$–(O–CH(CH$_3$)CH$_2$)$_{30}$–(O–CH$_2$CH$_2$)$_{77}$–O– |
| PPG-PEG-PPG 1900 MW | ED2k | –NH–CH(CH$_3$)–[(OCH$_2$CH$_2$)$_2$(OCH$_2$CH(CH$_3$))$_{36}$(OCH(CH$_3$)CH$_2$)$_3$]–NH– |

Chain Extender Used in Chain Extension Reaction

| Prepolymer | Abbreviation | Chemical Structure |
|---|---|---|
| Lysine | Lys | (lysine with R$_{15}$ on α-carbonyl, linked via both amines) |
| Aspartic Acid | Asp | (aspartate with R$_{15}$–NH– on α-carbon, two carbonyl linkages) |
| 2,2-Bis(Hydroxymethyl) Propionic Acid | HMPA | (central C with CH$_3$, C(=O)R$_{15}$, and two –CH$_2$O– linkages) |
| Fumarate coupled with 3-Mercaptopropionic Acid | fMPA | R$_{15}$–C(=O)–CH$_2$CH$_2$–S–CH(C(=O)–)–CH$_2$–C(=O)– |
| Fumarate coupled with Cysteamine | fCA | R$_{15}$–NH–CH$_2$CH$_2$–S–CH(C(=O)–)–CH$_2$–C(=O)– |
| Succinic Acid | SA | –C(=O)–CH$_2$CH$_2$–C(=O)– |

R$_{15}$ = DHPD or R$_{15}$ = H for lysine with free —NH$_2$ where specified.

Poly(Ether Urethane)

| Polymer | Backbone Composition | DHPD Type | Weight % DHPD | M$_w$ | PD | Note |
|---|---|---|---|---|---|---|
| PEU-1 | 89 wt % EG1k; 11 wt % Lys | Dopamine | 13 | 200,000 | 2.0 | |
| PEU-2 | 89 wt % EG1k; 11 wt % Lys | Dopamine | 8.2 | 140,000 | 1.2 | Additional Lysine |
| PEU-3 | 94 wt % F2k; 6 wt % Lys | Dopamine | 4.8 | — | — | |
| PEU-4 | 29 wt % EG1k; 65 wt % | Dopamine | 6.4 | — | — | |

Poly(Ether Ester)

| Polymer | Backbone Composition | DHPD Type | Weight % | M$_w$ | PD | Note |
|---|---|---|---|---|---|---|
| PEE-1 | 91 wt % EG1k; | DOPA | 7.7 | 34,000 | 1.3 | |
| PEE-2 | 86 wt % EG600; | DOHA | 21 | 18,000 | 4.2 | |
| PEE-3 | 91 wt % EG1k; | DOHA | 13 | 11,000 | 2.9 | |

-continued

| Polymer | Backbone Composition | DHPD Type | Weight % | $M_w$ | PD | Note |
|---|---|---|---|---|---|---|
| PEE-4 | 85 wt % EG1k; | Dopamine | 9.4 | 21,000 | 2.0 | |
| PEE-5 | 71 wt % EG1k; | Dopamine | 6.8 | 77% 17,000* | 2.7 1.2 | |
| PEE-6 | 92 wt % F2k; 8 wt % fMPA | Dopamine | 3.0 | 79% 27,000* | 1.8 1.4 | |
| PEE-7 | 64 wt % EG1k; | DOHA | 6.1 | 63,000 | 1.7 | |
| PEE-8 | 68 wt % EG600; | Dopamine | 16 | 15,000 | 4.8 | |

*Bimodal molecular weight distribution.

Poly(Ether Amide)

| Polymer | Backbone Composition | DHPD Type | Weight % DHPD | $M_w$ | PD | Note |
|---|---|---|---|---|---|---|
| PEA-1 | 93 wt % ED2k; 7 wt % fCA | DOHA | 5.9 | — | — | |
| PEA-2 | 80 wt % ED2k; 12 wt % Lys; | DOPA | 2.9 | 16,000 | 1.4 | Lysine with free —NH$_2$ |

Poly(Ether Ester Urethane)

| Polymer | Backbone Composition | DHPD Type | Weight % | $M_w$ | PD | Note |
|---|---|---|---|---|---|---|
| PEEU-1 | 66 wt % EG1k; 26 wt % | Dopamine | 6.0 | — | — | |
| PEEU-2 | 63 wt % EG1k; 18 wt % | Dopamine | 10 | — | — | |
| PEEU-3 | 64 wt % EG600; 21 wt % | Dopamine | 12 | — | — | Additional Lysine with free |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A bioadhesive construct, comprising:
   a support; and
   a coating comprising a multihydroxyphenyl (DHPD) functionalized polymer (DHPp) wherein the functionalized DHPp comprises the formula:

$$CA\text{-}[Z\text{-}PA\text{-}(L)_a\text{-}(DHPD)_b]_n$$

wherein
   CA is a central atom that is carbon;
   each Z, independently, is a C1 to a C6 linear or branched, substituted or unsubstituted alkyl group or a bond;
   each PA, independently, is a substantially poly(ethylene oxide) polyether;
   each L, independently, is a succinamic acid linker wherein an ester group links said succinamic acid linker to said PA and wherein an amide group links said succinamic acid linker to said DHPD;
   each DHPD, independently is a multihydroxy phenyl;
   "a" has a value of a value of 1;
   "b" has a value of 1; and
   "n" has a value of 4.

2. The bioadhesive construct of claim 1, further comprising an oxidant.

3. The bioadhesive construct of claim 1, wherein the oxidant is formulated with the coating.

4. The bioadhesive of claim 2, wherein the oxidant is applied to the coating.

5. The bioadhesive construct of claim 1, wherein the support is a film, a mesh, a membrane, or a prosthetic.

6. The bioadhesive construct of claim 4, wherein the support is a film, a mesh, a membrane, or a prosthetic.

7. The bioahesive construct of claim 1, wherein the construct is hydrated.

8. The bioadhesive construct of claim 4, wherein the construct is hydrated.

* * * * *